(12) United States Patent
Yurkovetskiy et al.

(10) Patent No.: US 8,349,308 B2
(45) Date of Patent: Jan. 8, 2013

(54) MODIFIED POLYMERS FOR DELIVERY OF POLYNUCLEOTIDES, METHOD OF MANUFACTURE, AND METHODS OF USE THEREOF

(75) Inventors: Aleksandr Yurkovetskiy, Littleton, MA (US); Mao Yin, Needham, MA (US); Timothy B. Lowinger, Carlisle, MA (US); Carolina B. Cabral, Somerset, NJ (US); Charles E. Hammond, Billerica, MA (US); Cheri A. Stevenson, Haverhill, MA (US)

(73) Assignee: Mersana Therapeutics, Inc., Cambridge, MA (US)

( * ) Notice: Subject to any disclaimer, the term of this patent is extended or adjusted under 35 U.S.C. 154(b) by 93 days.

(21) Appl. No.: 13/073,815

(22) Filed: Mar. 28, 2011

(65) Prior Publication Data

US 2011/0243880 A1 Oct. 6, 2011

Related U.S. Application Data

(60) Provisional application No. 61/317,907, filed on Mar. 26, 2010.

(51) Int. Cl.
*A61K 31/74* (2006.01)
*A61K 47/48* (2006.01)
*C07H 21/04* (2006.01)
*C12N 15/11* (2006.01)

(52) U.S. Cl. .............. 424/78.17; 525/54.2; 536/24.5; 514/44

(58) Field of Classification Search ................ None
See application file for complete search history.

(56) References Cited

U.S. PATENT DOCUMENTS

| 5,811,510 A | 9/1998 | Papisov |
| 5,863,990 A | 1/1999 | Papisov |
| 5,958,398 A | 9/1999 | Papisov |
| 5,994,109 A | 11/1999 | Woo et al. |
| 6,126,964 A | 10/2000 | Wolff et al. |

(Continued)

FOREIGN PATENT DOCUMENTS

WO WO-2006044986 A1 4/2006

(Continued)

OTHER PUBLICATIONS

Addepalli et al. "Modulation of Thermal Stability can Enhance the Potency of siRNA." *Nuc. Acids Res.* 38.20(2010):7320-7331.
Akinc et al. "Development of Lipidoid-siRNA Formulations for Systemic Delivery to the Liver." *Mol. Ther.* 17.5(2009):872-879.
Akinc et al. "Targeted Delivery of RNAi Therapeutics with Endogenous and Exogenous Ligand-Based Mechanisms." *Mol. Ther.* 18.7(2010):1357-1364.
Bartlett et al. "Impact of Tumor-Specific Targeting and Dosing Schedule on Tumor Growth Inhibition after Intravenous Administration of siRNA-Containing Nanoparticles." *Biotechnol. Bioeng.* 99.4(2008):975-985.

(Continued)

*Primary Examiner* — Richard Schnizer
(74) *Attorney, Agent, or Firm* — Mintz Levin Cohn Ferris Glovsky and Popeo, P.C.; Ivor R. Elrifi; Heidi A. Erlacher

(57) ABSTRACT

A polynucleotide delivery vehicle comprising a modified polymer is provided herein, the modified polymer having the following formula:

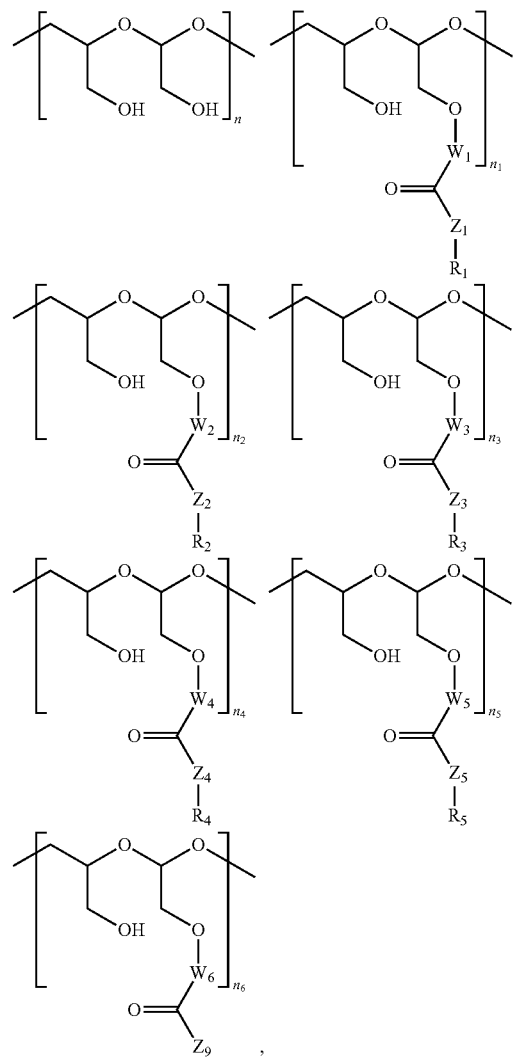

in which $W_1$, $W_2$, $W_3$, $W_4$, $W_5$, $W_6$, $Z_1$, $Z_2$, $Z_3$, $Z_4$, $Z_5$, $Z_9$, $R_1$, $R_2$, $R_3$, $R_4$, $R_5$, $n_1$, $n_2$, $n_3$, $n_4$, $n_5$, and $n_6$ are defined herein. Also disclosed are methods of delivering a polynucleotide to the cytoplasm of a selected tissue type or cell type and methods of reducing expression of a gene in a cell or a subject in need thereof with the modified polymer.

31 Claims, No Drawings

U.S. PATENT DOCUMENTS

| | | | |
|---|---|---|---|
| 6,254,890 B1 | 7/2001 | Hirosue et al. | |
| 6,300,458 B1 | 10/2001 | Vandenberg | |
| 6,383,811 B2 | 5/2002 | Wolff et al. | |
| 6,525,031 B2 | 2/2003 | Manoharan | |
| 6,794,189 B2 | 9/2004 | Wolff et al. | |
| 6,822,086 B1 | 11/2004 | Papisov | |
| 6,878,374 B2 | 4/2005 | Yu et al. | |
| 6,881,576 B2 | 4/2005 | Wolff et al. | |
| 6,897,068 B2 | 5/2005 | Monahan et al. | |
| 6,919,091 B2 | 7/2005 | Trubetskoy et al. | |
| 6,936,729 B2 | 8/2005 | Wolff et al. | |
| 7,018,609 B2 | 3/2006 | Hwang Pun et al. | |
| 7,019,113 B2 | 3/2006 | Rozema et al. | |
| 7,033,607 B2 | 4/2006 | Trubetskoy et al. | |
| 7,048,925 B2 | 5/2006 | Van et al. | |
| 7,070,807 B2 | 7/2006 | Mixson | |
| 7,087,770 B2 | 8/2006 | Wolff et al. | |
| 7,094,605 B2 | 8/2006 | Wakefield et al. | |
| 7,098,030 B2 | 8/2006 | Rozema et al. | |
| 7,098,032 B2 | 8/2006 | Trubetskoy et al. | |
| 7,138,382 B2 | 11/2006 | Wolff et al. | |
| 7,160,924 B2 | 1/2007 | Kinstler et al. | |
| 7,163,677 B2 | 1/2007 | Li et al. | |
| 7,163,695 B2 | 1/2007 | Mixson | |
| 7,208,314 B2 | 4/2007 | Monahan et al. | |
| 7,270,808 B2 | 9/2007 | Cheng et al. | |
| 7,297,786 B2 | 11/2007 | McCray et al. | |
| 7,348,453 B2 | 3/2008 | Rozema et al. | |
| 7,358,223 B2 | 4/2008 | Zhao et al. | |
| 7,361,752 B2 | 4/2008 | Heidenreich et al. | |
| 7,396,919 B1 | 7/2008 | Wolff et al. | |
| 7,427,394 B2 | 9/2008 | Anderson et al. | |
| 7,442,764 B2 | 10/2008 | Rozema et al. | |
| 7,459,547 B2 | 12/2008 | Zamore et al. | |
| 7,470,539 B2 | 12/2008 | Wakefield et al. | |
| 7,476,401 B2 | 1/2009 | Monahan et al. | |
| 7,482,160 B2 | 1/2009 | Monahan et al. | |
| 7,491,538 B2 | 2/2009 | Wolff et al. | |
| 7,491,805 B2 | 2/2009 | Vargeese et al. | |
| 7,507,809 B2 | 3/2009 | Meyers | |
| 7,514,099 B2 | 4/2009 | Chen et al. | |
| 7,524,680 B2 | 4/2009 | Wolff et al. | |
| 7,528,118 B2 | 5/2009 | Soutschek et al. | |
| 7,534,878 B2 | 5/2009 | Liu et al. | |
| 7,700,541 B2 | 4/2010 | Tanaka et al. | |
| 7,700,542 B2 | 4/2010 | Zhao et al. | |
| 7,718,193 B2 | 5/2010 | Stayton et al. | |
| 7,745,651 B2 | 6/2010 | Heyes et al. | |
| 7,772,201 B2 | 8/2010 | Mixson | |
| 7,785,618 B2 | 8/2010 | Elmaleh et al. | |
| 7,790,150 B2 | 9/2010 | Papisov et al. | |
| 7,799,565 B2 | 9/2010 | MacLachlan et al. | |
| 7,807,815 B2 | 10/2010 | MacLachlan et al. | |
| 7,816,337 B2 | 10/2010 | Rozema et al. | |
| 7,838,619 B2 | 11/2010 | Papisov | |
| 7,982,027 B2 | 7/2011 | MacLachlan et al. | |
| 8,008,355 B2 | 8/2011 | Rozema et al. | |
| 8,017,109 B2 | 9/2011 | Wakefield et al. | |
| 8,101,164 B2 * | 1/2012 | Papisov et al. | 424/78.3 |
| 2004/0105840 A1 | 6/2004 | Kinstler et al. | |
| 2004/0166089 A1 | 8/2004 | Yu et al. | |
| 2005/0049387 A1 | 3/2005 | Van et al. | |
| 2005/0064595 A1 | 3/2005 | MacLachlan et al. | |
| 2006/0019911 A1 | 1/2006 | Papisov | |
| 2006/0058513 A1 | 3/2006 | Papisov et al. | |
| 2007/0258993 A1 | 11/2007 | Apostolopoulos et al. | |
| 2008/0132689 A1 | 6/2008 | Rozema et al. | |
| 2008/0152661 A1 | 6/2008 | Rozema et al. | |
| 2008/0241102 A1 | 10/2008 | Hersel et al. | |
| 2008/0269450 A1 | 10/2008 | Wakefield et al. | |
| 2008/0274116 A1 | 11/2008 | Keil et al. | |
| 2008/0281041 A1 | 11/2008 | Rozema et al. | |
| 2008/0281044 A1 | 11/2008 | Monahan et al. | |
| 2008/0281074 A1 | 11/2008 | Rozema | |
| 2009/0053169 A1 | 2/2009 | Castillo et al. | |
| 2009/0074852 A1 | 3/2009 | Kaufmann et al. | |
| 2009/0148396 A1 | 6/2009 | Akullian et al. | |
| 2009/0156459 A1 | 6/2009 | Castillo et al. | |
| 2009/0220615 A1 | 9/2009 | Frechet et al. | |
| 2009/0233359 A1 | 9/2009 | Kwon | |
| 2009/0297609 A1 | 12/2009 | Shoichet et al. | |
| 2009/0304798 A1 | 12/2009 | Davis et al. | |
| 2010/0041152 A1 | 2/2010 | Wheeler et al. | |
| 2010/0062968 A1 | 3/2010 | Pulendran et al. | |
| 2010/0179181 A1 * | 7/2010 | Rolke et al. | 514/283 |
| 2010/0305149 A1 * | 12/2010 | Yurkovetskiy et al. | 514/283 |

FOREIGN PATENT DOCUMENTS

| | | |
|---|---|---|
| WO | WO-2006069782 A2 | 7/2006 |
| WO | WO-2007109584 A1 | 9/2007 |
| WO | WO-2008127532 A1 | 10/2008 |
| WO | WO-2009086558 A1 | 7/2009 |
| WO | WO-2009140421 A2 | 11/2009 |
| WO | WO-2009140423 A2 | 11/2009 |
| WO | WO-2009140427 A2 | 11/2009 |
| WO | WO-2009140429 A2 | 11/2009 |
| WO | WO-2009140432 A2 | 11/2009 |
| WO | WO-2010005847 A1 | 1/2010 |
| WO | WO-2010021720 A1 | 2/2010 |
| WO | WO-2010021770 A1 | 2/2010 |
| WO | WO-2010033240 A2 | 3/2010 |
| WO | WO-2010053596 A1 | 5/2010 |
| WO | WO-2010053597 A2 | 5/2010 |
| WO | WO-2010054266 A2 | 5/2010 |
| WO | WO-2010077678 A2 | 7/2010 |

OTHER PUBLICATIONS

Bartlett et al. "Impact of Tumor-Specific Targeting on the Biodistribution and Efficacy of siRNA Nanoparticles Measured by Multimodality in vivo Imaging." *PNAS.* 104.39(2007):15549-15554.

Biswal et al. "Development of a Targeted siRNA Delivery System Using FOL-PEG-PEI Conjugate." *Mol. Biol. Rep.* 37.6(2010):2919-2926.

Bumcrot et al. "RNAi Therapeutics: A Potential New Class of Pharmaceutical Drugs." *Nat. Chem. Biol.* 2.12(2006):711-719.

Burchard et al. "MicroRNA-like Off-Target Transcript Regulation by siRNAs is Species Specific." *RNA.* 15.2(2009):308-315.

Cardoso et al. "siRNA Delivery by a Transferrin-Associated Lipid-Based Vector: A Non-Viral Strategy to Mediate Gene Silencing." *J. Gene Med.* 9.3(2007):170-183.

Carthew et al. "Origins and Mechanisms of miRNAs and siRNAS." *Cell.* 136.4(2009):642-655.

Chen et al. "Lipophilic siRNAS Mediate Efficient Gene Silencing in Oligondendrocytes with Direct CNS Delivery." *J. Control Release.* 144.2(2010):227-232.

Convertine et al. "Development of a Novel Endosomolytic Diblock Copolymer for siRNA Delivery." *J. Control Release.* 133.3(2009):221-229.

Creusat et al. "Proton Sponge Trick for pH-Sensitive Disassembly of Polyethylenimine-Based siRNA Delivery Systems." *Bioconjug. Chem.* 21.5(2010):994-1002.

Davis et al. "Evidence of RNAi in Humans from Sytemically Administered siRNA Via Targeted Nanoparticles." *Nature.* 464.7291(2010):1067-1070.

Davis. "The First Targeted Delivery of siRNA in Humans Via a Self-Assembling, Cyclodextrin Polymer-Based Nanoparticle: From Concept to Clinic." *Mol. Pharm.* 6.3(2009):659-668.

de Fougerolles et al. "Interfering with Disease: A Progress Report on siRNA-Based Therapeutics." *Nat. Rev. Drug Discov.* 6.6(2007):443-453.

de Martimprey et al. "New Core-Shell Nanoparticles for the Intravenous Delivery of siRNA to Experimental Thyroid Papillary Carcinoma." *Pharm. Res.* 27.3(2010):498-509.

Dharap et al. "Tumor-Specific Targeting of an Anticancer Drug Delivery System by LHRH Peptide." *PNAS.* 102.36(2005):12962-12967.

Gao et al. "Progress in siRNA Delivery Using Multifunctional Nanoparticles." *RNA Therapeutics, Meth. Mol. Biol.* 629(2010):53-67.

Gopalakrishnan et al. "siRNA and DNA Transfer to Cultured Cells." *Macromol. Drug Deliv. Meth. Mol. Biol.* 480(2009):31-52.

Harris et al. "Tissue-Specific Gene Delivery Via Nanoparticle Coating." *Biomaterials.* 31.5(2010):998-1006.

Hashida et al. "Cell-Specific Delivery of Genes with Glycosylated Carriers." *Adv. Drug Deliv. Rev.* 52.3(2001):187-196.

Jiang et al. "DNA/PEI/Alginate Polyplex as an Efficient in Vivo Gene Delivery System." *Biotech. Bioproc. Eng.* 12(2007):684-689.

John et al. "Effective RNAi-Mediated Gene Silencing Without Interruption of the Endogenous MicroRNA Pathway." *Nature.* 449.7163(2007):745-747.

Judge et al. "Design of Noninflammatory Synthetic siRNA Mediating Potent Gene Silencing in Vivo." *Mol. Ther.* 13.3(2006):494-505.

Kretschmer et al. "An Automated Algorithm for Sequence Confirmation of Chemically Modified Oligonucleotides by Tandem Mass Spectrometry." *Anal. Biochem.* 405.2(2010):213-223.

Landesman et al. "In vivo Quantification of Formulated and Chemically Modified Small Interfering RNA by Heating-in-Triton Quantitative Reverse Transcription Polymerase Chain Reaction (HIT qRT-PCR)." *Silence.* 1.1(2010):16.

Lasham et al. "A Rapid and Sensitive Method to Detect siRNA-Mediated mRNA Cleavage in vivo using 5' Race and a Molecular Beacon Probe." *Nuc. Acids Res.* 38.3(2010):e19.

Liao et al. "Knockdown of Apolipoprotein B, an Atherogenic Apolipoprotein, in HepG2 Cells by Lentivirus-Mediated siRNA." *Biochem. Biophys. Res. Commun.* 344.2(2006):478-483.

Malek et al. "In vivo Pharmacokinetics, Tissue Distribution and Underlying Mechanisms of Various PEI(-PEG)/siRNA Complexes." *Toxicol. Appl. Pharmacol.* 236.1(2009):97-108.

Manickam et al. "Effect of Innate Glutathione Leves on Activity of Redox-Responsive Gene Delivery Vectors." *J. Control Release.* 141.1(2010):77-84.

Merkel et al. "Nonviral siRNA Delivery to the Lung: Investigation of PEG-PEI Polyplexes and Their in Vivo Performance." *Mol. Pharm.* 6.4(2009):1246-1260.

Meyer et al. "Synthesis and Biological Evaluation of a Bioresponsibe and Endosomolytic siRNA-Polymer Conjugate." *Mol. Pharm.* 6.3(2009):752-762.

Mudd et al. "Hybrid PET/CT for Noninvasive Pharmacokinetic Evaluation of Dynamic PolyConjugates, a Synthetic siRNA Delivery System." *Bioconjug. Chem.* 21.7(2010):1183-1189.

Nishina et al. "Efficient in Vivo Delivery of siRNA to the liver by Conjugation of Alpha-Tocopherol." *Mol. Ther.* 16.4(2008):734-740.

Ozpolat et al. "Nanomedicine Based Approaches for the Delivery of siRNA in Cancer." *J. Intern. Med.* 267.1(2010):44-53.

Philipp et al. "Hydrophobically Modified Oligoethylenimines as Highly Efficient Transfection Agents for siRNA Delivery." *Bioconjug. Chem.* 20.11(2009):2055-2061.

Rensen et al. "Design and Synthesis of Novel N-Acetylgalactosamine-Terminated Glycolipids for Targting of Lipoproteins to the Hepatic Asialogylcoprotein Receptor." *J. Med. Chem.* 47.23(2004):5798-5808.

Rozema et al. "Dynamic Polyconjugates for Targeted in vivo Delivery of siRNA to Hepatocytes." *PNAS.* 104.32(2007):12982-12987.

Schlee et al. "siRNA and isRNA: Two Edges of One Sword." *Mol. Ther.* 14.4(2006):463-470.

Sliedregt et al. "Design and Synthesis of Novel Amphiphilic Dendritic Galactosides for Selective Targeting of Liposomees to the Hepatic Asiaglycoprotein Receptor." *J. Med. Chem.* 42.4(1999):609-618.

Soutschek et al. "Therapeutic Silencing of an Endogenous Gene by Systemic Administration of Modified siRNAS." *Nature.* 432.7014(2004):173-178.

Sugahara et al. "Tissue-Penetrating Delivery of Compounds and Nanoparticles into Tumors." *Cancer Cell.* 16.6(2009):510-520.

Ta et al. "Thermosensitive Liposomes Modified with Poly(N-isopropylacrylamide-co-propylacrylic Acid) Copolymers for Triggered Release of Doxorubicin." *Biomacromol.* 11.8(2010):1915-1920.

Vaishnaw et al. "A Status Report on RNAi Therapeutics." *Silence.* 1.1(2010):14.

Vornlocher. "Antibody-Directed Cell-Type-Specific Delivery of siRNA." *Trends Mol. Med.* 12.1(2006):1-3.

Watanabe et al. "In vivo siRNA Delivery with Dendritic Poly(L-lysine) for the Treatment of Hypercholestrolemia." *Mol. Biosyst.* 5.11(2009):1306-1310.

Watts et al. "Effect of Chemical Modifications on Modulation of Gene Expression by Duplex Antigene RNAs that are Complementary to Non-Coding Transcripts at Gene Promoters." *Nuc. Acids Res.* 38.15(2010):5242-5259.

Wilson et al. "Orally Delivered Thioketal Nanoparticles Loaded with TNF-alpha-siRNA Target Inflammation and Inhibit Gene Expression in the Intestines." *Nat. Mater.* 9.11(2010):923-928.

Yu et al. "Cross-Species Comparison of in vivo PK/PD Relationships for Second-Generation Antisense Oligonucleotides Targeting Apoliprotein B-100." *Biochem. Pharmacol.* 77.5(2009):910-919.

Zhu et al. "Targeted Delivery of siRNA to Hepatocytes and Hepatic Stellate Cells by Bioconjugation." *Bioconjug. Chem.* 21.11(2010):2119-2127.

Zimmermann et al. "RNAi-Mediated Gene Silencing in Non-Human Primates." *Nature.* 441.7089(2006):111-114.

Zuckerman et al. "siRNA Knockdown of Ribonucleotide Reductase Inhibits Melanoma Cell Line Proliferation Alone or Synergistically with Temozolomide." *J. Invest. Dermatol.* 131.2(2011):453-460.

* cited by examiner

SEQUENCE LISTING

```
<160> NUMBER OF SEQ ID NOS: 2

<210> SEQ ID NO 1
<211> LENGTH: 21
<212> TYPE: RNA
<213> ORGANISM: Artificial Sequence
<220> FEATURE:
<223> OTHER INFORMATION: Chemically synthesized sequence
<220> FEATURE:
<221> NAME/KEY: misc_feature
<222> LOCATION: (1)..(1)
<223> OTHER INFORMATION: wherein n is an Adenine and a phosphate group
      is conjugated to its 5' end
<220> FEATURE:
<221> NAME/KEY: misc_feature
<222> LOCATION: (2)..(2)
<223> OTHER INFORMATION: wherein n is a 2'-methoxy modified Adenine
<220> FEATURE:
<221> NAME/KEY: misc_feature
<222> LOCATION: (20)..(20)
<223> OTHER INFORMATION: wherein n is a 2'-methoxy modified Adenine
<220> FEATURE:
<221> NAME/KEY: misc_feature
<222> LOCATION: (20)..(20)
<223> OTHER INFORMATION: wherein n is linked to the nucleotide at
      position 21 via a phosphorothioate linker

<400> SEQUENCE: 1
nnaguugcca cccacauucn g                                              21

<210> SEQ ID NO 2
<211> LENGTH: 21
<212> TYPE: RNA
<213> ORGANISM: Artificial Sequence
```

```
<220> FEATURE:
<223> OTHER INFORMATION: Chemically synthesized sequence
<220> FEATURE:
<221> NAME/KEY: misc_feature
<222> LOCATION: (1)..(1)
<223> OTHER INFORMATION: wherein n is a Guanine and a -(CH2)6-SH is
      conjugated to its 5' end
<220> FEATURE:
<221> NAME/KEY: misc_feature
<222> LOCATION: (4)..(4)
<223> OTHER INFORMATION: wherein n is a 2'-methoxy modified Uracil
<220> FEATURE:
<221> NAME/KEY: misc_feature
<222> LOCATION: (6)..(6)
<223> OTHER INFORMATION: wherein n is a 2'-methoxy modified Uracil
<220> FEATURE:
<221> NAME/KEY: misc_feature
<222> LOCATION: (10)..(10)
<223> OTHER INFORMATION: wherein n is a 2'-methoxy modified Uracil
<220> FEATURE:
<221> NAME/KEY: misc_feature
<222> LOCATION: (13)..(13)
<223> OTHER INFORMATION: wherein n is a 2'-methoxy modified Cytosine
<220> FEATURE:
<221> NAME/KEY: misc_feature
<222> LOCATION: (16)..(16)
<223> OTHER INFORMATION: wherein n is a 2'-methoxy modified Cytosine
<220> FEATURE:
<221> NAME/KEY: misc_feature
<222> LOCATION: (17)..(19)
<223> OTHER INFORMATION: wherein n is a 2'-methoxy modified Uracil
<220> FEATURE:
<221> NAME/KEY: misc_feature
<222> LOCATION: (20)..(20)
<223> OTHER INFORMATION: wherein n is a 2'-methoxy modified Adenine
<220> FEATURE:
<221> NAME/KEY: misc_feature
<222> LOCATION: (20)..(20)
<223> OTHER INFORMATION: wherein n is linked to the nucleotide at
      position 21 via a phosphorothioate linker

<400> SEQUENCE: 2
naangngggn ggnaannnnn g                                          21
```

MODIFIED POLYMERS FOR DELIVERY OF POLYNUCLEOTIDES, METHOD OF MANUFACTURE, AND METHODS OF USE THEREOF

RELATED APPLICATIONS

This application incorporates by reference and claims the benefit of and priority under 35 USC §119(e) to U.S. Patent Application No. 61/317,907, filed Mar. 26, 2010. The contents of this application are hereby incorporated by reference in their entirety.

INCORPORATION-BY-REFERENCE OF SEQUENCE LISTING

The contents of the text file named "41977-501001US_ST25.txt," which was created on Jun. 8, 2011 and is 2.29 KB in size, are hereby incorporated by reference in their entirety.

FIELD OF THE INVENTION

The present disclosure relates to modified polymers useful to deliver polynucleotide therapeutics such as siRNA to cells.

BACKGROUND

Oligonucleotides have important therapeutic applications in medicine. Oligonucleotides can be used to silence genes responsible for a particular disease, or change expression levels of genes in a manner that might be beneficial to an organism. Gene-silencing prevents formation of a protein product by inhibiting translation, affecting the stability of a particular RNA species, or by affecting the amount of transcription of a particular genetic locus. Importantly, gene-silencing agents are a promising alternative to traditional small, organic compounds that inhibit the function of the protein linked to the disease. siRNA, shRNA (small hairpin RNA), antisense RNA, and micro-RNAs are oligonucleotides that carry out gene silencing as described above.

RNA interference (RNAi) is a process in which RNAs called small-interfering RNAs or siRNAs inhibit expression of a gene that has an identical or nearly identical sequence (i.e. an intracellular RNA to which the inhibitory RNA is capable of hybridizing under physiological conditions). In many cases, inhibition is caused by degradation of the messenger RNA (mRNA) transcribed from the target gene. The mechanism and cellular machinery through which such RNAi-directed target RNA degradation occurs has been investigated using both genetic and biochemical approaches. In the case of dsRNA (represented either by transfected dsRNA, shRNA encoded by an introduced expression vector, or endogenous RNA that may be processed to become an active RNAi moiety), processing occurs in the cytoplasm of a cell; if necessary, the RNAi molecule (or its precursor) is first processed into RNA fragments 21 to 25 nucleotides long. These RNAi molecules can then be loaded into dicer complexes, where they direct cleavage of target RNA molecules.

The ability to specifically affect expression of a target gene by RNAi can be therapeutically beneficial as many diseases arise from the abnormal expression of a particular genetic locus, gene or group of genes. In many cases, therapeutic value may be derived by specifically inhibiting expression of the mutant form of a gene. In specific embodiments, RNAi can be used to inhibit or attenuate the expression of the deleterious gene and therefore alleviate symptoms of a disease or provide a treatment or cure. For example, genes contributing to a cancerous state, to viral replication, or to a dominant genetic disease such as myotonic dystrophy can be inhibited. Alternatively, indirect gene activation of pathways is also possible by, for example, down regulation of a suppressor gene. Inflammatory diseases such as arthritis can also be treated by inhibiting genes such as NF-κB, cyclooxygenase or cytokines. Examples of targeted organs include, for example, the liver, lung, pancreas, spleen, kidney, skin, brain, prostate, and heart.

Antisense methodology generally describes the complementary hybridization of synthetic nucleic acid sequences to mRNA or DNA such that the normal functions, such as protein synthesis, of these intracellular nucleic acids are disrupted. Hybridization is the sequence-specific hydrogen bonding via Watson-Crick base pairs of oligonucleotides to RNA or single-stranded DNA. Such base pairs are said to be complementary to one another. In one mechanism, hybridization arrest, the oligonucleotide inhibitor binds to the target polynucleotide and thus prevents the binding of essential proteins, most often ribosomes, to the polynucleotide by simple steric hindrance. Another means by which antisense oligonucleotides disrupt polynucleotide function is by hybridization to a target mRNA, followed by enzymatic cleavage of the targeted RNA by intracellular RNase H. Disruption of function may also occur through altered intracellular trafficking of a targeted RNA.

Micro-RNAs are a large group of small RNAs produced naturally in organisms, at least some of which regulate the expression of target genes. Micro-RNAs are formed from an approximately 70-nucleotide single-stranded hairpin precursor transcript by Dicer. In many instances, the micro-RNA is transcribed from a portion of the DNA sequence that previously had no known function. As such, these coding regions may in fact be considered genetic loci. Micro-RNAs are not translated into proteins but rather often bind to specific messenger RNAs and may affect translation of the bound RNA.

The intracellular delivery of various therapeutic compounds such as polynucleotides is compromised because the trafficking of many compounds into living cells is highly restricted by the complex membrane systems of the cell. Specific transporters allow the selective entry of nutrients or regulatory molecules, while excluding most exogenous molecules such as polynucleotides and proteins. Various strategies can be used to improve transport of polynucleotides into cells, including lipid carriers, biodegradable polymers, and various conjugate systems. The most well studied approaches for improving the transport of foreign polynucleotides into cells involve the use of viral vectors or cationic lipids and related cytofectins. Viral vectors can be used to transfer genes efficiently into some cell types, but they generally cannot be used to introduce chemically synthesized molecules into cells. An alternative approach is to use delivery formulations incorporating cationic lipids, which interact with polynucleotides through one end and lipids or membrane systems through another. Another approach to delivering biologically active compounds involves the use of conjugates. Conjugates are often selected based on the ability of certain molecules to be selectively transported into specific cells, for example via receptor-mediated endocytosis. By attaching an active compound to molecules that are actively transported across the cellular membranes, the effective transfer of that compound into cells or specific cellular organelles can be realized. In other cases, conjugates may be used to mediate incorporation of an active compound into a delivery vehicle. Alternatively, molecules able to penetrate cellular membranes without active transport mechanisms, for example, various lipophilic molecules, can be used to deliver compounds of interest.

Compositions and methods for improving the efficiency of systemic and local delivery of biologically active molecules, particularly polynucleotide therapeutics such as siRNA are needed. The present disclosure fulfills this need and provides additional advantages described herein.

SUMMARY

In one aspect, the invention features a biodegradable, biocompatible polynucleotide delivery vehicle comprising a modified polymer of Formula (I):

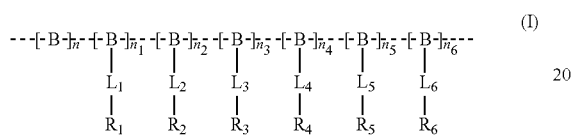

wherein:
  each B, independently, is the same or different polymer unit;
  $L_1$ is a linker between a B unit and $R_1$, wherein $R_1$ is a targeting group for a selected tissue, pathogen, cell, or cellular location;
  $L_2$ is a linker between a B unit and $R_2$, wherein $R_2$ is a charge group;
  $L_3$ is a linker between a B unit and $R_3$, wherein $R_3$ is a charge-modifying group;
  $L_4$ is a linker between a B unit and $R_4$, wherein $R_4$ is a hydrophobic group;
  $L_5$ is a linker between a B unit and $R_5$, wherein $R_5$ is a protective group;
  $L_6$ is a linker between a B unit and $R_6$, wherein $R_6$ is a polynucleotide;
  each of $n$, $n_1$, $n_2$, $n_3$, $n_4$, $n_5$, and $n_6$ is the molar fraction of the corresponding polymer units ranging between 0 and 1 inclusive, $n+n_1+n_2+n_3+n_4+n_5+n_6=1$; provided that neither $n$ nor $n_6$ is 0.

In Formula (I), the dashed lines between the polymer units, e.g. $[B-L_1-R_1]$, $[B-L_2-R_2]$, $[B-L_3-R_3]$, $[B-L_4-R_4]$, $[B-L_5-R_5]$, and $[B-L_6-R_6]$, indicate that the units can be connected to each other in any order. In other words, the appending groups $R_1$, $R_2$, $R_3$, $R_4$, $R_5$, and $R_6$, can be randomly distributed along the polymer backbone.

Particularly, the invention features a modified polyacetal of Formula (VI):

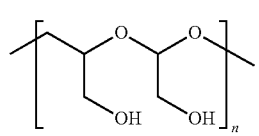

(VI)

wherein:
  each of $W_1$, $W_2$, $W_3$, $W_4$, $W_5$ and $W_6$, independently, is a covalent bond or —C(O)—Y— with —C(O) connected to the polyacetal backbone;

Y is $-[C(R_9R_{10})_a]-$ or $-[C(R_9R_{10})]_a-X_1-[C(R_9R_{10})]_b-$;

$X_1$ is an oxygen atom, a sulfur atom or $-NR_{11}$;

each of $R_9$ and $R_{10}$ independently is hydrogen, $C_{1-6}$ alkyl, $C_{6-10}$ aryl, 5 to 12-membered heteroaryl or $C_{3-8}$ cycloalkyl;

$R_{11}$ is hydrogen, $C_{1-6}$ alkyl, $C_{6-10}$ aryl, 5 to 12-membered heteroaryl, $C_{3-8}$ cycloalkyl or $-C(O)-C_{1-3}$ alkyl;

$Z_9$ is $Z_6$-$T_1$ or $Z_8$;

$T_1$ is $-Z_7-R_6$;

$Z_8$ is a linear or branched polyamino moiety substituted with one or more $-Z_7-R_6$ and optionally substituted with one or more substituents selected from the group consisting of -Q-$R_1$, -Q-$R_3$, -Q-$R_4$, and -Q-$R_5$;

each Q independently is a covalent bond or $-C(O)-$;

each of $Z_1$, $Z_2$, $Z_3$, $Z_4$, $Z_5$, and $Z_6$, independently, is a covalent bond, $-NR_{17}$, or $-NR_{17}R_{18}-$, in which each of $R_{17}$ and $R_{18}$ independently is H, $C_{2-8}$ alkyl, or $-C_{2-10}$ alkyl-N($R_x$)—, $R_x$ being H or an amino acid attached to the nitrogen via the carbonyl group of the amino acid; or $R_{17}$ and $R_{18}$, together with the nitrogen atom to which they are attached form a 4 to 7-membered heterocycloalkyl ring containing 0 or 1 additional heteroatom selected from N, O, and S;

each $Z_7$ independently is $-C(O)-T_2-T_3-$ or $-N(R')-T_2-T_3-$ with $T_3$ connected to $R_6$, in which R' is H or $C_{1-6}$ alkyl, $T_2$ is selected from alkylthioaryl, arylthioalkyl, alkylthioalkyl, arylthioaryl, alkyldithioaryl, aryldithioalkyl, alkyldithioalkyl and aryldithioaryl, and $T_3$ is a covalent bond, $-C(O)N(R'')-C_{1-8}$ alkyl, $-N(R'')C(O)-C_{1-8}$ alkyl, or $C_{1-8}$ alkyl, in which R'' is H or $C_{1-6}$ alkyl;

each of a and b independently is an integer between 1 and 6 inclusive;

each of n, $n_1$, $n_2$, $n_3$, $n_4$, $n_5$, and $n_6$ is the molar fraction of the corresponding polyacetal unit ranging between 0 and 1; $n+n_1+n_2+n_3+n_4+n_5+n_6=1$; provided that neither n nor $n_6$ is 0;

$R_1$ is a targeting group for a selected tissue, pathogen, cell, or cellular location;

$R_2$ is a charge group optionally substituted with one or more substituents selected from the group consisting of -Q-$R_1$, -Q-$R_3$, -Q-$R_4$, and -Q-$R_5$;

$R_3$ is a charge-modifying group;

$R_4$ is a hydrophobic group;

$R_5$ is a protective group;

$R_6$ is a polynucleotide;

the ratio ($m_1$) of the number of $R_1$ to the total number of polyacetal units of the polyacetal is 0 to 0.25;

the ratio ($m_3$) of the number of $R_3$ to the total number of polyacetal units of the polyacetal is 0 to 100;

the ratio ($m_4$) of the number of $R_4$ to the total number of polyacetal units of the polyacetal is 0 to 30;

the ratio ($m_5$) of the number of $R_5$ to the total number of polyacetal units of the polyacetal is 0 to 0.03;

the ratio ($m_6$) of the number of $R_6$ to the total number of polyacetal units of the polyacetal is 0.0004 to 0.10; and the polyacetal backbone has a molecular weight of about 10 kDa to about 250 kDa.

In Formula (VI), the disconnection or gap between the polyacetal units, like the dashed lines between the polymer units of Formula (I), indicates that the units can be connected to each other in any order. In other words, the appending groups, $R_1$, $R_2$, $R_3$, $R_4$, $R_5$, and $R_6$, can be randomly distributed along the polymer backbone.

The polymers of Formulae (I) and (VI) can include one or more of the following features.

$m_1$ is 0.002 to 0.25.

$m_3$ is 0.002 to 100.

$m_4$ is 0.03 to 0.30.

$m_5$ is 0.01 to 0.03.

When $Z_9$ is $Z_6$-$T_1$, (i) $n_1$ is not 0 and each of $n_2$, $n_3$, $n_4$, and $n_5$ is 0;
(ii) neither $n_1$ nor $n_2$ is 0 and each of $n_3$, $n_4$, and $n_5$ is 0;
(iii) none of $n_1$, $n_2$ and $n_3$ is 0 and each of $n_4$ and $n_5$ is 0;
(iv) none of $n_1$, $n_2$ and $n_4$ is 0 and each of $n_3$ and $n_5$ is 0;
(v) none of $n_1$, $n_2$, $n_3$ and $n_4$ is 0 and $n_5$ is 0;
(vi) neither $n_1$ nor $n_4$ is 0 and each of $n_2$, $n_3$ and $n_5$ is 0;
(vii) $n_2$ is not 0 and each of $n_1$, $n_3$, $n_4$, and $n_5$ is 0;
(viii) neither $n_2$ nor $n_3$ is 0 and each of $n_1$, $n_4$ and $n_5$ is 0;
(ix) neither $n_2$ nor $n_4$ is 0 and each of $n_1$, $n_3$ and $n_5$ is 0;
(x) none of $n_2$, $n_3$ and $n_4$ is 0 and each of $n_1$ and $n_5$ is 0;
(xi) none of $n_1$, $n_2$, $n_3$, $n_4$, and $n_5$ is 0; or
(xii) each of $n_1$, $n_2$, $n_3$, $n_4$, and $n_5$ is 0.

When $Z_9$ is $Z_6$-$T_1$, n is between about 0.01 and about 0.9996 inclusive;
$n_1$ is between about 0.002 and about 0.25 inclusive;
$n_2$ is between about 0.02 and about 0.90 inclusive;
$n_3$ is between about 0.02 and about 0.81 inclusive;
$n_4$ is between about 0.03 and about 0.30 inclusive;
$n_5$ is between about 0.01 and about 0.03 inclusive; and
$n_6$ is between about 0.0004 and about 0.10 inclusive.

When $Z_9$ is $Z_8$, each of $n_1$, $n_3$, $n_4$, and $n_5$ is 0.

When $Z_9$ is $Z_8$, $R_2$ is a linear or branched polyamino moiety optionally substituted with one or more substituents selected from the group consisting of -Q-$R_1$, -Q-$R_3$, -Q-$R_4$, and -Q-$R_5$.

When $Z_9$ is $Z_8$, (i) $m_1$ is not 0 and each of $m_3$, $m_4$ and $m_5$ is 0;
(ii) neither $m_1$ nor $m_4$ is 0 and each of $m_3$ and $m_5$ is 0;
(iii) none of $m_1$, $m_4$ and $m_5$ is 0 and $m_3$ is 0;
(iv) neither $m_1$ nor $m_3$ is 0 and each of $m_4$ and $m_5$ is 0;
(v) none of $m_1$, $m_3$ and $m_4$ is 0 and $m_5$ is 0; or
(vi) none of $m_1$, $m_3$, $m_4$ and $m_5$ is 0.

When $Z_9$ is $Z_8$, n is between about 0.70 and about 0.99 inclusive;
$m_1$ is 0.002 to 0.25;
$m_3$ is 0.002 to 100;
$m_4$ is 0.03 to 0.30;
$m_5$ is 0.01 to 0.03; and
$m_6$ is 0.0004 to 0.10.

Each of $Z_1$, $Z_2$, $Z_3$, $Z_4$, $Z_5$, and $Z_6$, independently, can be ethylenediamine, piperazine, bis(piperidine), 1,3-diaminopropane, 1,4-diaminobutane (i.e., putrescine), 1,5-diaminopentane (i.e., cadaverine), decamethylenediamine, hexamethylenediamine, lysine, histidine, arginine, tryptophan, agmatine or ornithine. Preferably, each of $R_1$, $R_2$, $R_3$, $R_4$, $R_5$, and $T_1$ is attached to a N atom of $Z_1$, $Z_2$, $Z_3$, $Z_4$, $Z_5$, and $Z_6$ respectively and the N atom is not that of the amide moiety via which $Z_1$, $Z_2$, $Z_3$, $Z_4$, $Z_5$, or $Z_6$ is attached to the polyacetal backbone. For example, each of $Z_1$, $Z_2$, $Z_3$, $Z_4$, $Z_5$, and $Z_6$ is

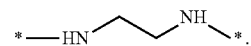

$T_2$ can be —$C_{1-8}$ alkylthio-$C_{6-10}$ aryl, —$C_{6-10}$ arylthio-$C_{1-8}$ alkyl, —$C_{1-8}$ alkylthio-$C_{1-8}$ alkyl, —$C_{6-10}$ arylthio-$C_{6-10}$ aryl, —$C_{1-8}$ alkyldithio-$C_{6-10}$ aryl, —$C_{6-10}$ aryldithio-$C_{1-8}$ alkyl, —$C_{1-8}$ alkyldithio-$C_{1-8}$ alkyl, or —$C_{6-10}$ aryldithio-$C_{6-10}$ aryl.

$Z_7$ can be (1)
$$*-\overset{O}{\underset{\|}{C}}-(C_{2\text{-}6}\text{alkyl})-S-S-(C_{2\text{-}6}\text{alkyl})-*;$$

(2)
$$*-\overset{O}{\underset{\|}{C}}-(\text{Aryl})-S-S-(C_{2\text{-}6}\text{alkyl})-*;$$

(3)
$$*-\overset{O}{\underset{\|}{C}}-\text{Aryl}-S-S-\text{Aryl}-\overset{O}{\underset{\|}{C}}-\underset{H}{N}-(C_{1\text{-}6}\text{alkyl})-*;$$

(4)
$$*-\underset{H}{N}-(C_{2\text{-}6}\text{alkyl})-S-S-(C_{2\text{-}6}\text{alkyl})-*; \text{ or}$$

(5)
$$*-\overset{O}{\underset{\|}{C}}-(C_{2\text{-}6}\text{Alkyl})-S-S-(C_{2\text{-}6}\text{Alkyl})-\overset{O}{\underset{\|}{C}}-\underset{H}{N}-(C_{1\text{-}6}\text{alkyl})-*;$$

wherein —C(O) or —NH is oriented towards the polyacetal backbone.

$Z_7$ can be (1)
[structure: *—C(O)—phenyl—S—S—(CH$_2$)$_6$—*]

(2)
[structure: *—C(O)—CH$_2$CH$_2$—S—S—(CH$_2$)$_6$—*]; or (3)
[structure: *—C(O)—CH$_2$CH$_2$—S—S—CH$_2$CH$_2$—C(O)—NH—(CH$_2$)$_6$—*];

wherein —C(O) is oriented towards the polyacetal backbone.

$Z_8$, when otherwise unsubstituted, can be (1)
$$*-\underset{R_z}{N}-[CH_2CH_2-\underset{H}{N}]_c-H;$$

(2)
$$*-\underset{R_z}{N}-[CH_2CH_2-\underset{H}{N}]_d-[CH_2CH_2-\underset{R_y}{N}]_e-H;$$

(3)
$$*-HN-CH_2CH_2CH_2-\underset{H}{N}-CH_2CH_2CH_2CH_2-NH_2;$$

(4)
$$*-HN-CH_2CH_2CH_2-\underset{NH}{N}=C(NH_2)-NH_2;$$

(5)
$$*-HN-CH_2CH_2CH_2-\underset{H}{N}-CH_2CH_2CH_2CH_2-\underset{H}{N}-CH_2CH_2CH_2-NH_2;$$

(6)
$$*-HN-CH_2CH_2CH_2-[\text{imidazole}];$$

(7)
$$*-[(L)\text{-Lys}]_{d_3};$$

(8)
$$*-[(L)\text{-Arg}]_{d_2};$$

or (9) a dendrimer of any of generations 2-10 selected from poly-L-lysine, poly(propyleneimine) and poly(amidoamine) dendrimers;

wherein:
 $R_y$ is an amino acid attached to the nitrogen via the carbonyl group of the amino acid or a linear or branched polyamino moiety;
 $R_z$ is H or a linear or branched polyamino moiety;
 c is an integer between 2 and 600 inclusive;
 d is an integer between 0 and 600 inclusive;
 e is an integer between 1 and 150 inclusive;
 $d_2$ is an integer between 2 and 20 inclusive; and
 $d_3$ is an integer between 2 and 200 inclusive.

For example, $Z_8$, when otherwise unsubstituted, is (1) a linear polyethylenimine having a molecular weight of about 500 to about 25000 dalton (e.g., about 500 to about 2500 dalton); (2) a branched polyethylenimine having a molecular weight of about 500 to about 25000 dalton (e.g., about 500 to about 1200 dalton);

(3)
$$*-\underset{R_z}{N}-[CH_2CH_2-\underset{H}{N}]_d-[CH_2CH_2-\underset{e}{N}]_e-C(O)-CH(NH_2)-CH_2-\text{C}_6H_4\text{-OH};\text{ or}$$

(4)
$$*-\underset{R_z}{N}-[CH_2CH_2-\underset{H}{N}]_d-[CH_2CH_2-\underset{e}{N}]_e-C(O)-CH(NH_2)-CH_2-\text{imidazole}.$$

Each of $R_y$ and $R_z$, independently, can be a polyamino moiety comprising a monomer unit of —[C$_{2\text{-}6}$ alkyl-NH]—.

$R_1$ can include galactosamine, galactose, N-acetylgalactosamine, folic acid, RGD peptides, LHRH receptor targeting peptides, ErbB2 (HER$_2$) receptor targeting peptides, prostate specific membrane bound antigen (PSMA) targeting peptides, lipoprotein receptor LRP1 targeting ligands, ApoE protein derived peptides and/or transferrin.

$R_2$ can be

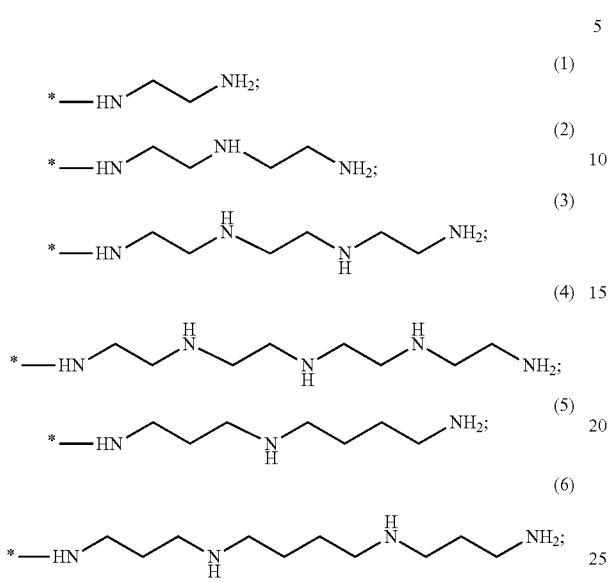

(7) a linear polyethylenimine having a molecular weight of about 500 to about 25000 dalton;
(8) a branched polyethylenimine having a molecular weight of about 500 to about 25000 dalton;

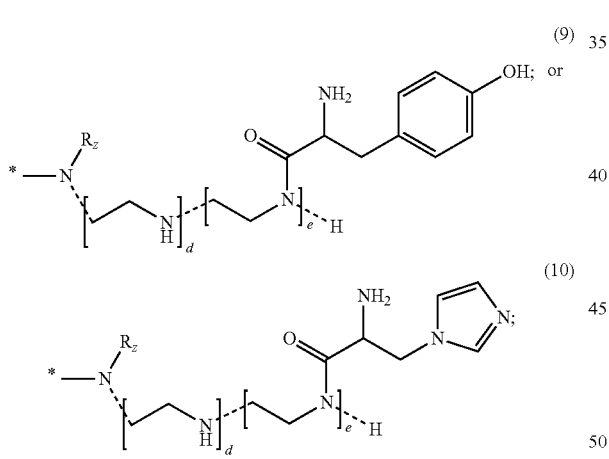

wherein
$R_z$ is H or a linear or branched polyamino moiety;
d is an integer between 0 and 600 inclusive; and
e is an integer between 1 and 150 inclusive.

For example, $R_2$ is

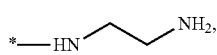

a linear polyethylenimine having a molecular weight of about 500 to about 2500 dalton or a branched polyethylenimine having a molecular weight of about 500 to about 1200 dalton.

$R_3$ can be of Formula (XVI):

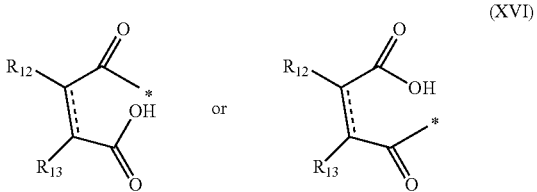

wherein:
$R_{12}$ is hydrogen, $C_{1-5}$ alkyl or $C_{6-10}$ aryl;
$R_{13}$ hydrogen, $C_{1-10}$ alkyl, $C_{6-10}$ aryl, $-(CH_2)_g-CO_2R_{14}$, $-(CH_2)_g-C(O)SR_{14}$, $-(CH_2)_qC(O)S(CH_2)_gCO_2R_{14}$ or $-(CH_2)_qCONHR_{15}$;
$R_{14}$ is hydrogen or $C_{1-5}$ alkyl;
$R_{15}$ is hydrogen, $C_{1-5}$ alkyl, $C_{6-10}$ aryl, aralkyl, alkyldithioaryl, aryldithioalkyl, alkyldithioalkyl, aryldithioaryl, $-(CH_2)_gCHO$ or $R_1$;
g is an integer between 1 and 5 inclusive; q is an integer between 0 and 5 inclusive; and
----- is a single or a double bond.

For example, $R_3$ is

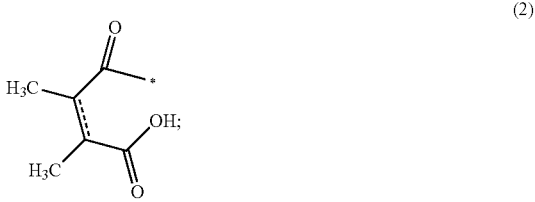

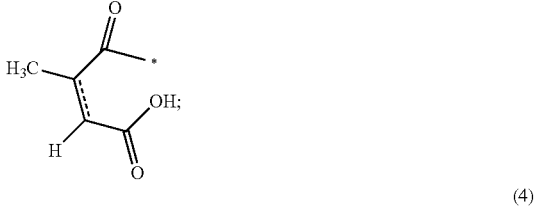

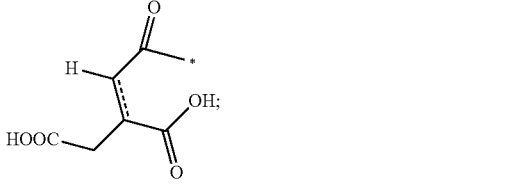

wherein $R_{16}$ is a hydrogen or $C_{1-2}$ alkyl. In particular, $R_3$ is $R_4$ can include unsaturated fatty acids, $C_{6-22}$ alkylamines, cholesterol, cholesterol derivatives or amino containing lipids. For example, $R_4$ is

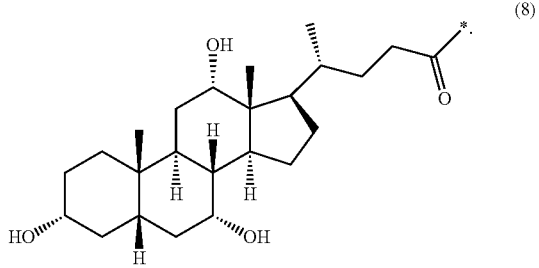

(8)

$R_6$ can be a natural, synthetic, or semi-synthetic polynucleotide, DNA, RNA or an oligonucleotide. For example, $R_6$ a double stranded oligonucleotide having about 12 to about 30 nucleotides or a single stranded oligonucleotide having about 8 to about 64 nucleotides.

The polyacetal backbone can have a molecular weight of about 100 kDa, about 70 kDa, about 60 kDa or about 40 kDa.

In another aspect, the invention features a method for delivering a polynucleotide to the cytoplasm of a selected tissue type or cell type. The method comprises contacting the modified polymer of Formula (I), e.g., the modified polyacetal of Formula (VI), with the selected tissue type (e.g., a liver tissue or a kidney tissue) or cell type (e.g., a blood cell, an endothelial cell, a cancer cell, a pancreatic cell, or a neural cell).

A method of reducing expression of a gene in a cell is also provided herein. The method comprises delivering to the cytoplasm of a cell an effective amount of the modified polymer of Formula (I), e.g., the modified polyacetal of Formula (VI), wherein the modified polymer (e.g., polyacetal) contains a polynucleotide that is complementary to at least a portion of the gene.

In yet another aspect, the invention relates to a method of reducing expression of a gene in a subject. The method includes administering to a subject in need thereof an effective amount of the modified polymer of Formula (I), e.g., the modified polyacetal of Formula (VI), wherein the modified polyacetal contains a polynucleotide is complementary to at least a portion of the gene.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting.

Other features and advantages of the invention will be apparent from the following detailed description and claims.

DETAILED DESCRIPTION

Described herein are modified polymers, in particular modified polymers that can be used to deliver polynucleotides to specific types of cells. The polymer backbone is modified by attaching the polynucleotide groups and optionally groups that function to target the modified polymer to the desired cell type and groups that facilitate delivery into the cell. An advantageous feature of these modified polymers is that a wide variety of polynucleotides can be attached, including therapeutic agents such as siRNA. Varying the type and amount of the other functional groups allows targeting of and delivery into many different cell types. In one embodiment, the modified polymers described herein have sufficient solubility, stealth, biodegradability and targeting to provide an effective amount of polynucleotide to a target location prior to clearance or degradation. Moreover, such properties may disallow production of off-target binding (or even targeted binding in tissues or cells where such binding would be deleterious) which can result in reduced efficacy or even toxicity. Other features and advantages of the modified polymers are described in detail below.

Terminology

Definitions of certain terms used herein are provided prior to setting forth the invention in detail. Compounds are described using standard nomenclature. Unless defined otherwise, all technical and scientific terms used herein have the same meaning as is commonly understood by one of skill in the art to which this disclosure belongs.

The use of the articles "a", "an", and "the" in both the following description and claims are to be construed to cover both the singular and the plural, unless otherwise indicated herein or clearly contradicted by context. The terms "comprising", "having", "including", and "containing" are to be construed as open terms (i.e., meaning "including but not limited to") unless otherwise noted. Additionally whenever "comprising" or another open-ended term is used in an embodiment, it is to be understood that the same embodiment can be more narrowly claimed using the intermediate term "consisting essentially of" or the closed term "consisting of."

Recitation of ranges of values are merely intended to serve as a shorthand method of referring individually to each separate value falling within the range, unless otherwise indicated herein, and each separate value is incorporated into the specification as if it were individually recited herein. A range used herein, unless otherwise specified, includes the two limits of the range. For example, the expressions "x being an integer between 1 and 6" and "x being an integer of 1 to 6" both mean "x being 1, 2, 3, 4, 5, or 6". The term "wt %" refers to percent by weight. All methods described herein can be performed in any suitable order unless otherwise indicated herein or otherwise clearly contradicted by context. The use of any and all examples, or exemplary language (e.g., "such as") provided herein, is intended merely to better illustrate the invention and is not to be construed as a limitation on the scope of the claims unless explicitly otherwise claimed. No language in the specification is to be construed as indicating that any non-claimed element is essential to what is claimed.

An asterisk ("*") is used to indicate a bond that functions as a point of attachment for a substituent or linking group. For example,

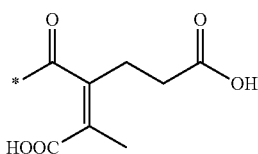 [SMILES: *C(=O)/C(CCC(=O)O)=C(/C)C(=O)O]

is covalently bound to another group via a single bond between the substituted group and the keto group adjacent to the asterisk.

"Alkyl" is intended to include both branched and straight chain (linear) saturated aliphatic hydrocarbon groups, having the specified number of carbon atoms, generally from 1 to about 12 carbon atoms. The term $C_{1-6}$ alkyl is intended to include $C_1$, $C_2$, $C_3$, $C_4$, $C_5$, and $C_6$ alkyl groups. $C_{1-8}$ alkyl is intended to include $C_1$, $C_2$, $C_3$, $C_4$, $C_5$, $C_6$, $C_7$, and $C_8$ alkyl groups. Examples of alkyl include, but are not limited to, methyl, ethyl, n-propyl, isopropyl, n-butyl, s-butyl, t-butyl 3-methylbutyl, t-butyl, n-pentyl, s-pentyl, n-hexyl, n-heptyl, and n-octyl.

In some embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

"Substituted alkyl" means an alkyl moiety having substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. An "arylalkyl" or an "aralkyl" moiety is an alkyl substituted with an aryl (e.g., phenylmethyl (benzyl)). An "alkylaryl" moiety is an aryl substituted with an alkyl (e.g., methylphenyl).

"Aryl" includes groups with aromaticity, including "conjugated," or multicyclic systems with at least one aromatic ring and do not contain any heteroatom in the ring structure. Examples include phenyl, benzyl, 1,2,3,4-tetrahydronaphthalenyl, etc.

"Heteroaryl" groups are aryl groups, as defined above, except having from one to four heteroatoms in the ring structure, and may also be referred to as "aryl heterocycles" or "heteroaromatics." As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, independently selected from nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and S(O)$_o$, where o is an integer of 1 or 2). It is to be noted that total number of S and O atoms in the aromatic heterocycle is not more than 1. Heteroaryl includes groups that are partially aromatic e.g., 4-benzo[d]-imidazolone.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, naphthridine, indole, benzofuran, purine, benzofuran, deazapurine, indolizine.

In the case of multicyclic aromatic rings, only one of the rings needs to be aromatic (e.g., 2,3-dihydroindole), although all of the rings may be aromatic (e.g., quinoline). The second ring can also be fused or bridged.

The aryl or heteroaryl aromatic ring can be substituted at one or more ring positions with such substituents as described above, for example, alkyl, alkenyl, akynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl).

As used herein, the term "cycloalkyl" refers to a saturated or unsaturated nonaromatic hydrocarbon mono- or multi-ring system having 3 to 30 carbon atoms (e.g., $C_3$-$C_{10}$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, and adamantyl. The term "heterocycloalkyl" refers to a saturated or unsaturated nonaromatic 3-8 membered monocyclic, 8-12 membered bicyclic, or 11-14 membered tricyclic ring system having one or more heteroatoms (such as O, N, S, or Se), unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, tetrahyrofuranyl, oxiranyl, azetidinyl, oxetanyl, thietanyl, 1,2,3,6-tetrahydropyridinyl, tetrahydropyranyl, dihydropyranyl, pyranyl, morpholinyl, and the like.

The cycloalkyl, heterocycloalkyl, aryl, or heteroaryl ring can be substituted at one or more ring positions (e.g., the ring-forming carbon or heteroatom such as N) with such substituents as described above, for example, alkyl, alkenyl, akynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl and heteroaryl groups can also be fused or bridged with alicyclic or heterocyclic rings, which are not aromatic so as to form a multicyclic system (e.g., tetralin, methylenedioxyphenyl).

"Amine" or "amino" refers to unsubstituted or substituted —NH$_2$. "Alkylamino" includes groups of compounds wherein nitrogen is bound to at least one alkyl group. Examples of alkylamino groups include benzylamino, methylamino, ethylamino, phenethylamino, etc. "Dialkylamino" includes groups wherein the nitrogen atom is bound to at least two additional alkyl groups. Examples of dialkylamino groups include, but are not limited to, dimethylamino and diethylamino. "Arylamino" and "diarylamino" include groups wherein the nitrogen is bound to at least one or two aryl groups, respectively. "Alkylarylamino", "alkylaminoaryl" or "arylaminoalkyl" refers to an amino group which is bound to at least one alkyl group and at least one aryl group. "Alkaminoalkyl" refers to an alkyl, alkenyl, or alkynyl group bound to a nitrogen atom which is also bound to an alkyl group. "Acylamino" includes groups wherein nitrogen is bound to an acyl group. Examples of acylamino include, but are not limited to, alkylcarbonylamino, arylcarbonylamino, carbamoyl and ureido groups.

"Amide" or "aminocarboxy" means compounds or moieties that contain a nitrogen atom that is bound to the carbon of a carbonyl or a thiocarbonyl group. The term includes "alkaminocarboxy" groups that include alkyl, alkenyl or alkynyl groups bound to an amino group which is bound to the carbon of a carbonyl or thiocarbonyl group. It also includes "arylaminocarboxy" groups that include aryl or heteroaryl moieties bound to an amino group that is bound to the carbon of a carbonyl or thiocarbonyl group. The terms "alkylaminocarboxy", "alkenylaminocarboxy", "alkynylaminocarboxy" and "arylaminocarboxy" include moieties wherein alkyl, alkenyl, alkynyl and aryl moieties, respectively, are bound to a nitrogen atom which is in turn bound to the carbon of a carbonyl group. Amides can be substituted with substituents such as straight chain alkyl, branched alkyl, cycloalkyl, aryl, heteroaryl or heterocycle. Substituents on amide groups may be further substituted.

"Polyamine" or "polyamino" means moieties containing two or more amino (e.g., primary amino, secondary amino, or tertiary amino groups) or amide groups. Examples of polyamino include but are not limited to, ethylenediamine, piperazine, bis(piperidine), 1,3-diaminopropane, 1,4-diaminobutane, decamethylenediamine, hexamethylenediamine, cadaverine, lysine, histidine, arginine, tryptophan, agmatine or ornithine, a linear or branched polymer containing a repeating unit of —[$C_{2-6}$ alkyl-NH]— such as linear or branched polyethylenimine, polyamino acid, and a dendrimer of any of generations 2-10 selected from poly-L-lysine, poly (propyleneimine) and poly(amidoamine) dendrimers. The term "bis(piperidine)" refers to a moiety containing two piperidine rings connected either by a covalent bond or an alkyl linker such as

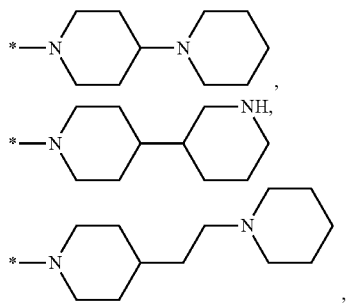

etc.

"Thioalkyl" means an alkyl group as defined herein with the indicated number of carbon atoms attached through a sulfur atom. $C_{1-6}$ alkylthio, is intended to include $C_1$, $C_2$, $C_3$, $C_4$, $C_5$, and $C_6$ alkylthio groups. $C_{1-8}$ alkylthio, is intended to include $C_1$, $C_2$, $C_3$, $C_4$, $C_5$, $C_6$, $C_7$, and $C_8$ alkylthio groups. The thioalkyl groups can be substituted with groups such as alkyl, alkenyl, alkynyl, halogen, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties.

"Thiocarbonyl" or "thiocarboxy" includes compounds and moieties which contain a carbon connected with a double bond to a sulfur atom.

"Thioether" includes moieties which contain a sulfur atom bonded to two carbon atoms or heteroatoms. Examples of thioethers include, but are not limited to alkthioalkyls, alkthioalkenyls and alkthioalkynyls. The term "alkthioalkyls" include moieties with an alkyl, alkenyl or alkynyl group bonded to a sulfur atom which is bonded to an alkyl group. Similarly, the term "alkthioalkenyls" refers to moieties wherein an alkyl, alkenyl or alkynyl group is bonded to a sulfur atom which is covalently bonded to an alkenyl group; and alkthioalkynyls" refers to moieties wherein an alkyl, alkenyl or alkynyl group is bonded to a sulfur atom which is covalently bonded to an alkynyl group.

"Thioaryl" means an aryl group as defined herein with the indicated number of carbon atoms attached through a sulfur atom.

"Alkyldithioaryl", "aryldithioalkyl", "alkyldithioalkyl" or "aryldithioaryl" means moieties which contain thioalkyl groups connected to thioaryl groups through a disulfide bridge.

"Halo" or "halogen" refers to fluoro, chloro, bromo and iodo. The term "perhalogenated" generally refers to a moiety wherein all hydrogen atoms are replaced by halogen atoms.

"Carboxylic acid" refers to a compound comprising a group of formula —$CO_2H$.

"Dicarboxylic acid" refers to a compound comprising two groups of formula —$CO_2H$.

"Acyl" includes moieties that contain the acyl radical (—C (O)—) or a carbonyl group. "Substituted acyl" includes acyl groups where one or more of the hydrogen atoms are replaced by, for example, alkyl groups, alkynyl groups, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Alkanoyl" means an alkyl group as defined above, attached through a keto (—(C=O)—) bridge. Alkanoyl groups have the indicated number of carbon atoms, with the carbon of the keto group being included in the numbered carbon atoms. For example a $C_2$ alkanoyl group is an acetyl group having the formula $CH_3(C=O)$—.

Alkyl, alkenyl, alkynyl, cycloalkyl, heterocycloalkyl, amino, aryl, heteroaryl, thioalkyl and other organic moieties mentioned above include both substituted and unsubstituted moieties. Suitable substituents are those described herein.

"Biocompatible" is intended to describe compounds that exert minimal destructive or host response effects while in contact with body fluids or living cells or tissues. Thus a biocompatible group, as used herein, refers to an aliphatic, alicyclic, heteroaliphatic, heteroalicyclic, aryl or heteroaryl moiety, which falls within the definition of the term biocompatible, as defined above and herein. The term "Biocompatibility" as used herein, is also taken to mean minimal interactions with recognition proteins, e.g., naturally occurring antibodies, cell proteins, cells and other components of biological systems, unless such interactions are specifically desirable. Thus, substances and functional groups specifically intended to cause the above effects, e.g., drugs and prodrugs, are considered to be biocompatible. Preferably (with exception of compounds intended to be cytotoxic, such as e.g. antineoplastic agents), compounds are "biocompatible" if their addition to normal cells in vitro, at concentrations similar to the intended systemic in vivo concentrations, results in less than or equal to 1% cell death during the time equivalent to the half-life of the compound in vivo (e.g., the period of time required for 50% of the compound administered in vivo to be eliminated/cleared), and their administration in vivo induces minimal and medically acceptable inflammation, foreign body reaction, immunotoxicity, chemical toxicity or other such adverse effects. In the above sentence, the term "normal cells" refers to cells that are not intended to be destroyed or otherwise significantly affected by the compound being tested.

"Biodegradable" polymers are polymers that are susceptible to biological processing in vivo. As used herein, "biodegradable" compounds are those that, when taken up by cells, can be broken down by the lysosomal or other chemical machinery or by hydrolysis into components that the cells can either reuse or dispose of without significant toxic effect on the cells. The degradation fragments preferably induce no or little organ or cell overload or pathological processes caused by such overload or other adverse effects in vivo. Examples of biodegradation processes include enzymatic and non-enzymatic hydrolysis, oxidation and reduction. Suitable conditions for non-enzymatic hydrolysis of the polymer backbones of various conjugates, for example, include exposure of the biodegradable conjugates to water at a temperature and a pH of lysosomal intracellular compartment. Biodegradation of some conjugate backbones, e.g. polyacetal conjugates of the present invention, can also be enhanced extracellularly, e.g. in low pH regions of the animal body, e.g. an inflamed area, in the close vicinity of activated macrophages or other cells releasing degradation facilitating factors. In some embodiments, the effective size of the polymer molecule at pH ~7.5 does not detectably change over 1 to 7 days, and remains within 50% of the original polymer size for at least several weeks. At pH ~5, on the other hand, the polymer preferably detectably degrades over 1 to 5 days, and is completely transformed into low molecular weight fragments within a two-week to several-month time frame. Polymer integrity in such tests can be measured, for example, by size exclusion HPLC. Although faster degradation may be in some cases preferable, in general it may be more desirable that the polymer degrades in cells with the rate that does not exceed the rate of metabolism or excretion of polymer fragments by the cells. In preferred embodiments, the polymers and polymer biodegradation byproducts are biocompatible.

"Hydrophilic" as it relates to substituents on the polymer monomeric units does not essentially differ from the common meaning of this term in the art, and denotes chemical moieties which contain ionizable, polar, or polarizable atoms, or which otherwise may be solvated by water molecules. Thus a hydrophilic group, as used herein, refers to an aliphatic, alicyclic, heteroaliphatic, heteroalicyclic, aryl or heteroaryl moiety, which falls within the definition of the term hydrophilic, as defined above. Examples of particular hydrophilic organic moieties which are suitable include, without limitation, aliphatic or heteroaliphatic groups comprising a chain of atoms in a range of between about one and twelve atoms, hydroxyl, hydroxyalkyl, amine, carboxyl, amide, carboxylic ester, thioester, aldehyde, nitro ($-NO_2$), nitryl ($-CN$), isonitryl ($-NC$), nitroso ($-NO$), hydroxylamine, mercaptoalkyl, heterocycle, carbamates, carboxylic acids and their salts, sulfonic acids and their salts, sulfonic acid esters, phosphoric acids and their salts, phosphate esters, polyglycol ethers, polyamines, polycarboxylates, polyesters and polythioesters. In preferred embodiments of the present invention, at least one of the polymer monomeric units include a carboxyl group (COOH), an aldehyde group (CHO), a methylol ($CH_2OH$) or a glycol (for example, $CHOH-CH_2OH$ or $CH-(CH_2OH)_2$.

"Hydrophilic" as it relates to the polymers generally does not differ from usage of this term in the art, and denotes polymers comprising hydrophilic functional groups as defined above. In some embodiments, hydrophilic polymer is a water-soluble polymer. Hydrophilicity of the polymer can be directly measured through determination of hydration energy, or determined through investigation between two liquid phases, or by chromatography on solid phases with known hydrophobicity, such as, for example, $C_4$ or $C_{18}$.

"Physiological conditions" as used herein, relates to the range of chemical (e.g., pH, ionic strength) and biochemical (e.g., enzyme concentrations) conditions likely to be encountered in the extracellular fluids of living tissues. For most normal tissues, the physiological pH ranges from about 7.0 to 7.4. Circulating blood plasma and normal interstitial liquid represent typical examples of normal physiological conditions.

"Polynucleotide" means a polymer containing at least two nucleotides. "Nucleotides" are the monomeric units of nucleic acid polymers. Polynucleotides with less than 120 monomeric units are often called oligonucleotides.

"PHF" refers to the polymer poly(1-hydroxymethylethylene hydroxymethyl-formal) available under the trademark FLEXIMER®.

As used herein, the terms "polymer unit", "monomeric unit", "monomer", "monomer unit", "unit" all refer to a repeatable structural unit in a polymer.

Unless otherwise specified, dashed lines or disconnections between polymer units in the formulae included herewith, such as those in Formulae (I) and (VI), indicate that the units are arranged in a random order. For example, the dashed lines in formula of

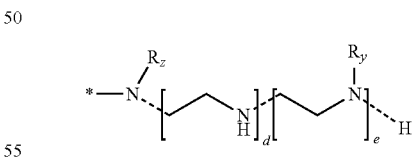

mean that the $-[CH_2CH_2NH]-$ unit and the $-[CH_2CH_2NR_y]-$ unit are randomly arranged.

"Gene" or "target gene" means a polynucleotide that encodes an RNA, for example, nucleic acid sequences including, but not limited to, structural genes encoding a polypeptide. The target gene can be a gene derived from a cell, an endogenous gene, a transgene, or exogenous genes such as genes of a pathogen, for example a virus, which is present in the cell after infection thereof. The cell containing the target gene can be derived from or contained in an organism, for example a plant, animal, protozoan, virus, bacterium, or fungus. Moreover, the target gene may be expressed in specific tissues or in a more widespread or ubiquitous manner (i.e. many or all tissues of an organism), and may comprise either a wild type or mutant allele of a specific gene.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

Modified Polymer Backbone

As stated above, the modified biodegradable, biocompatible polymers can be used as delivery vehicles for polynucleotides, for example polynucleotide therapeutics such as oligonucleotides and siRNA. The polymer backbone provides a scaffold onto which appended functional groups are attached via chemical linkers to a portion of the polymer units.

In one embodiment, the polymer backbone is a hydrophilic biodegradable, biocompatible polymer selected from carbohydrates, glycopolysaccharides, glycolipids, glycoconjugates, polyacetals, polyketals, and derivatives thereof. In other embodiments, the polymer backbone is a naturally occurring linear and branched biodegradable biocompatible homopolysaccharide selected from cellulose, amylose, dextran, levan, fucoidan, carraginan, inulin, pectin, amylopectin, glycogen and lixenan. In yet other embodiments, the polymer backbone is a naturally occurring linear and branched biodegradable biocompatible heteropolysaccharide selected from agarose, hyluronan, chondroitinsulfate, dermatansulfate, keratansulfate, alginic acid and heparin.

In yet another embodiment, the polymer backbone is a hydrophilic polymer selected from polyacrylates, polyvinyl polymers, polyesters, polyorthoesters, polyamides, polypeptides, and derivatives thereof.

In other embodiments, the polymer backbone comprises polysaccharides activated by selective oxidation of cyclic vicinal diols of 1,2-, 1,4-, 1,6-, and 2,6-pyranosides, and 1,2-, 1,5-, 1,6-furanosides, or by oxidation of lateral 6-hydroxy and 5,6-diol containing polysaccharides prior to conjugation with one or more modifiers.

In one embodiment, the polymer backbone comprise activated hydrophilic biodegradable biocompatible polymers comprising from 0.1% to 100% polyacetal moieties represented by the following chemical structure:

wherein;
$R_7$ and $R_8$ are independently hydrogen, hydroxyl, hydroxy alkyl (e.g., —CH(OH), —CH(OH)—CH(OH) or -carbonyl; and
o is an integer between 20 and 2000 inclusive.

In one embodiment, the polymer can be obtained from partially oxidized dextran (β1→6)-D-glucose). In this embodiment, the polymer comprises a random mixture of the unmodified dextran (A), partially oxidized dextran acetal units (B) and exhaustively dextran acetal units (C) of the following structures:

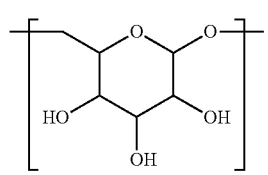
(A)

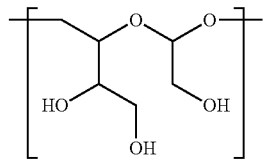
(B)

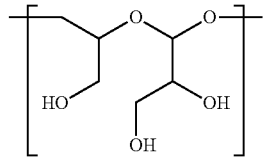
(B)

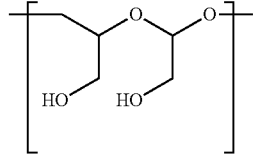
(C)

In another embodiment, the polymer backbone comprises unmodified acetal units, i.e., polyacetal segments. In some embodiments, the polyacetals can be derived from exhaustively oxidized dextran. These polymers have been described in U.S. Pat. No. 5,811,510, which is hereby incorporated by reference for its description of polyacetals at column 2, line 65 to column 8, line 55 and their synthesis at column 10, line 45 to column 11, line 14. In one embodiment, the unmodified polyacetal polymer is a poly(hydroxymethylethylene hydroxymethyl formal) polymer (PHF).

In addition to poly(hydroxymethylethylene hydroxymethyl formal) polymers, the backbone of the modified polymer can also comprise co-polymers of poly(hydroxymethylethylene hydroxymethyl formal) blocks and other acetal or non-acetal monomers or polymers. For example, polyethylene glycol polymers are useful as a stealth agent in the polymer backbone because they can decrease interactions between polymer side chains of the appended functional groups. Such groups can also be useful in limiting interactions such as between serum factors and the modified polymer. Other stealth agent monomers for inclusion in the polymer backbone include, for example, ethyleneimine, methacrylic acid, acrylamide, glutamic acid, and combinations thereof.

The acetal units are present in the modified polymer in an amount effective to promote biocompatibility. The unmodified acetal units can be described as a "stealth agent" that provides biocompatibility and solubility to the modified polymers. In addition, conjugation to a polyacetal polymer can modify the susceptibility to metabolism and degradation of the moieties attached to it, and influence biodistribution, clearance and degradation. The unmodified acetal units are monomers of Formula (II):

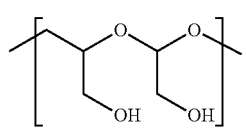
(II)

The molar fraction, n, of unmodified polyacetal units is the molar fraction available to promote biocompatibility, solubility and increase half-life, based on the total number of polymer units in the modified polymer. The molar fraction n may be the minimal fraction of unmodified monomer acetal units needed to provide biocompatibility, solubility, stability, or a particular half-life, or can be some larger fraction. The most desirable degree of cytotoxicity is substantially none, i.e., the modified polymer is substantially inert to the subject. However, as is understood by those of ordinary skill in the art, some degree of cytotoxicity can be tolerated depending on the severity of disease or symptom being treated, the efficacy of the treatment, the type and degree of immune response, and like considerations.

In one embodiment, in the modified polymer of Formula (I), one or more of the polymer units containing the groups $R_1$-$R_6$ are polyacetal units. Specifically, the modified segment of the polymer of Formula (I) comprises units of Formula (III):

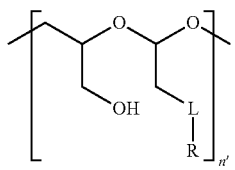

(III)

wherein L-R is one or more of $L_1$-$R_1$, $L_2$-$R_2$, $L_3$-$R_3$, $L_4$-$R_4$, $L_5$-$R_5$ and $L_6$-$R_6$, where each L is a linker and each R is a functional group, and n' represents one or more of $n_1$, $n_2$, $n_3$, $n_4$, $n_5$, and $n_6$, in which $n_1$ represents the molar fraction of polymer units modified with $L_1$-$R_1$, $n_2$ represents the molar fraction of polymer units modified with $L_2$-$R_2$ and so forth. Each L and each R are independently chosen and the molar fraction of each L-R combination varies from 0 to 1, with the limitation that the sum of the molar fractions of modified and unmodified polymer units is 1.

As shown in Formula (III) and the other formulae described herein, each polyacetal unit has a single hydroxyl group attached to the glycerol moiety of the unit and a single L-R group attached to the glycolaldehyde moiety of the unit. This is for convenience only and it should be construed that the polymer having units of Formula (III) and other formulae described herein (e.g., Formula (IV) below) can contain a random distribution of units having a single L-R group attached to the glycolaldehyde moiety of the units and those having a single L-R group attached to the glycerol moiety of the units as well as units having two L-R groups with one attached to the glycolaldehyde moiety and the other attached to the glycerol moiety of the units. Each L-R independently is selected from $L_1$-$R_1$, $L_2$-$R_2$, $L_3$-$R_3$, $L_4$-$R_4$, $L_5$-$R_5$, and $L_6$-$R_6$.

In one embodiment the invention describes modified polymers of Formula (IV):

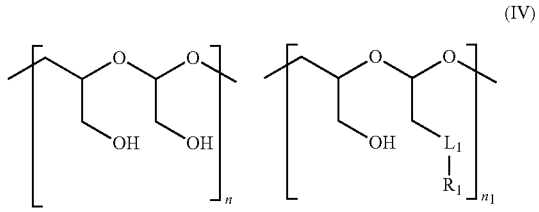

(IV)

-continued

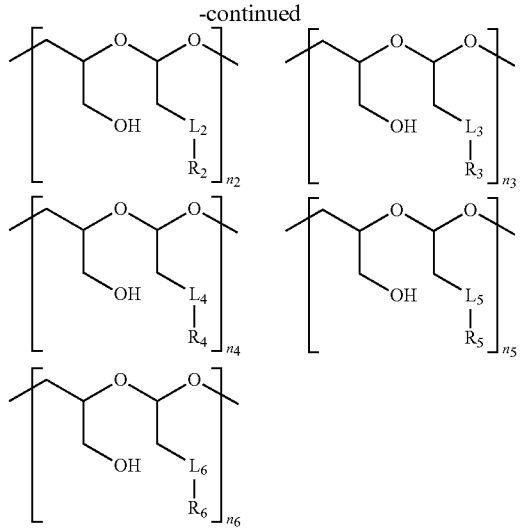

wherein:
$L_1$ is a linker between an acetal unit and $R_1$, wherein $R_1$ is a targeting group for a selected tissue, pathogen, cell, or cellular location;
$L_2$ is a linker between an acetal unit and $R_2$, wherein $R_2$ is a charge group;
$L_3$ is a linker between an acetal unit and $R_3$, wherein $R_3$ is a charge-modifying group;
$L_4$ is a linker between an acetal unit and $R_4$, wherein $R_4$ is a hydrophobic group;
$L_5$ is a linker between an acetal unit and $R_5$, wherein $R_5$ is a protective group;
$L_6$ is a linker between an acetal unit and $R_6$, wherein $R_6$ is a polynucleotide;
each of n, $n_1$, $n_2$, $n_3$, $n_4$, $n_5$, and $n_6$ is the molar fraction of the corresponding polymer units ranging between 0 and 1, and $n+n_1+n_2+n_3+n_4+n_5+n_6=1$; provided that neither n nor $n_6$ is 0

In the modified polymer of Formula (IV) the subunits may be distributed along the polymer backbone in any order (i.e. ordered, random or statistical distribution) and not all subunits are required.

The polymer backbone used for the modified polymers of Formula (IV) can have a molecular weight of about 10 kDa to about 250 kDa, or about 5 kDa, about 10 kDa, about 20 kDa, about 30 kDa, about 40 kDa, about 60 kDa, about 70 kDa, about 100 kDa or about 250 kDa. In another embodiment, the polymer backbone has a molecular weight of about 70 kDa. In yet another embodiment, the polymer backbone has a molecular weight of about 35 kDa.

The modified polymers provided herein are water soluble, having a water solubility of at least 0.1 mg/ml, at least 1.0 mg/ml, at least 10 mg/ml or at least 100 mg/ml.

The modified polymers provided herein increase the in vivo half life of the attached therapeutic agent, such as an attached polynucleotide. For example, some modified polymers provided herein increase the in vivo half life of the attached therapeutic agent 10-fold, 100-fold, or 1000-fold over the in vivo half life of the therapeutic agent not bound to the modified polymer.

In certain embodiments provided herein the therapeutic agent's biodistribution is altered when the therapeutic agent is administered attached to the modified polymer relative to its biodistribution when administered in the free form. For example when the target tissue is a tumor, the tumor/liver ratio for therapeutic agent administered attached to the modified polymer may increase at least 5-fold, at least 10-fold, at least 50-fold, or at least 100-fold over the tumor/liver ratio of therapeutic agent administered in the free form.

Functional Groups

The appended functional groups on the polymer backbone include the polynucleotide, e.g., oligonucleotide or siRNA, as well as groups that provide functionality to the polymer, including targeting groups, charge modifying groups, hydrophobic groups, cationic groups, groups that facilitate uptake into cells, groups that facilitate release from endosomes, and groups that slow polynucleotide degradation, for example. Functional groups can be defined chemically, e.g. cationic, hydrophobic; functionally e.g. targeting, charge modifying; or a combination thereof.

Interaction Modifiers

Functional groups other than the polynucleotide can be referred to collectively as interaction modifiers. An interaction modifier changes the way a molecule interacts with itself or with other molecules relative to the same molecule containing no interaction modifier. The result of this modification is that self-interactions or interactions with other molecules are either increased or decreased. It is to be understood that in the following discussion, the interaction modifiers are classified by either theorized function (e.g., "targeting group"), by description (e.g., "cationic group"), or a combination thereof. It is to be understood, however, that such classifications are for convenience only, in that a single group may fit within one or more categories, e.g., a cationic group in some circumstances may also be shown to function as a targeting group. Classification of a chemical moiety as one type of group therefore does not imply that the moiety has no other function or characteristic.

Linkers $L_1$-$L_6$

Appended groups are attached to the scaffold directly or via linkers. A linker is an attachment that is covalently bonded to the polymer backbone and to the interaction modifier or polynucleotide. In addition to providing attachment for an appended group, a linker can function to provide a means to increase the distance between the polymer backbone and an appended group, provide better presentation or orientation of the appended group, or shield an appended group from other appended groups, the polymeric backbone itself, or an agent in the environment of the modified polymer, among others. Linkers can be neutral or charged, hydrophilic or hydrophobic, and optionally include one or more labile bonds.

Exemplary linkers include $C_1$-$C_{12}$ alkyl, $C_1$-$C_{12}$ alkenyl, $C_1$-$C_{12}$ alkynyl, $C_6$-$C_{12}$ arylalkyl, $C_6$-$C_{12}$ arylalkenyl, $C_6$-$C_{12}$ arylalkynyl, ester, ether, ketone, alcohol, polyol, amide, amine, polyglycol, polyether, polyamine, thiol, thio ether, thioester, phosphorous containing linkers, and heterocyclic linkers.

In one embodiment, the linker comprises a labile bond. A labile bond is a covalent bond capable of being selectively broken, that is, the labile bond can be broken in the presence of other covalent bonds without the breakage of the other covalent bonds. A labile bond can be sensitive to pH, oxidative or reductive conditions or agents, temperature, salt concentration, the presence of an enzyme (such as esterases, including nucleases, and proteases), or the presence of an added agent. For example, a disulfide bond is capable of being broken in the presence of thiols without cleavage of any other bonds, such as carbon-carbon, carbon-oxygen, carbon-sulfur, carbon-nitrogen bonds, which can also be present in the molecule. Labile also means cleavable. A labile linker is thus a linker that contains a labile bond and provides a link or spacer between two other groups, such as between the polymer scaffold and an appended group. Breaking of the labile bond in a labile linker provides for release of an appended group attached to the polymer scaffold via the labile linker. In one embodiment, the linker is cleavable by an enzymatic cleavage reaction. In this embodiment, the linker is, for example, a nucleic acid or peptide linker. For example, the linker may contain a protease-reactive or protease-specific sequence. Examples include recognition motifs of exo- and endo-peptidases, extracellular metalloproteases, lysosomal proteases such as the cathepsins (cathepsin B), HIV proteases, as well as secretases, transferases, hydrolases, isomerases, ligases, oxidoreductases, esterases, glycosidases, phospholipases, endonucleases, ribonucleases and β-lactamases.

In one embodiment, the labile linker is a pH-labile linker. "pH-labile" refers to the selective breakage of a covalent bond under acidic conditions (pH<7) or basic conditions (pH>7). That is, the pH-labile bond is broken under acidic or basic conditions in the presence of other covalent bonds without their breakage. Substituted maleic anhydrides can be used to provide pH-labile linkages. The covalent bond formed by reaction between an amine on a compound of interest and the anhydride is readily cleaved at acidic pH. Thus, maleic anhydride derivatives can be reversibly attached to amine-containing compounds. In another embodiment, the labile bond is cleaved under oxidative or reductive conditions. For example, a disulfide constructed from two alkyl thiols is capable of being broken by reduction in the presence of thiols or reducing agents, without cleavage of carbon-carbon bonds. In this example, the carbon-carbon bonds are non-labile to the reducing conditions. In another embodiment, the labile bond is cleaved under physiological conditions or by an enzyme. For example, an ester bond can be cleaved in the pH range of about 4 to about 8 or it can be cleaved by an esterase enzyme.

In one embodiment, the linker comprises a reactive group capable of forming either an ionic or a covalent bond with another compound, such as an appended group R. Examples of reactive groups include nucleophiles and electrophiles. Reactive groups that form covalent bonds include isothiocyanate, isocyanate, acyl azide, acid halide, O-acyl urea, N-hydroxysuccinimide esters, succinimide esters, thioesters, amide, urea, sulfonyl chloride, aldehyde, ketone, ether, epoxide, carbonate, alkyl halide, imidoester, carboxylate, alkylphosphate, arylhalides (e.g., difluoro-dinitrobenzene), and anhydrides.

In one embodiment, the invention describes modified polymers of Formula (VI):

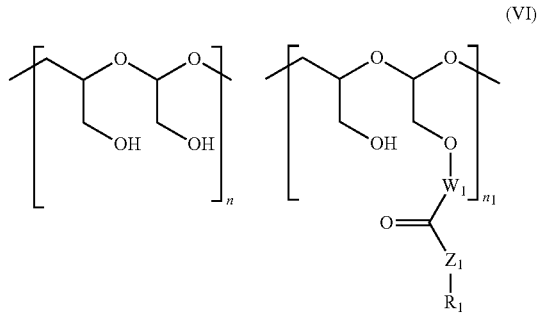

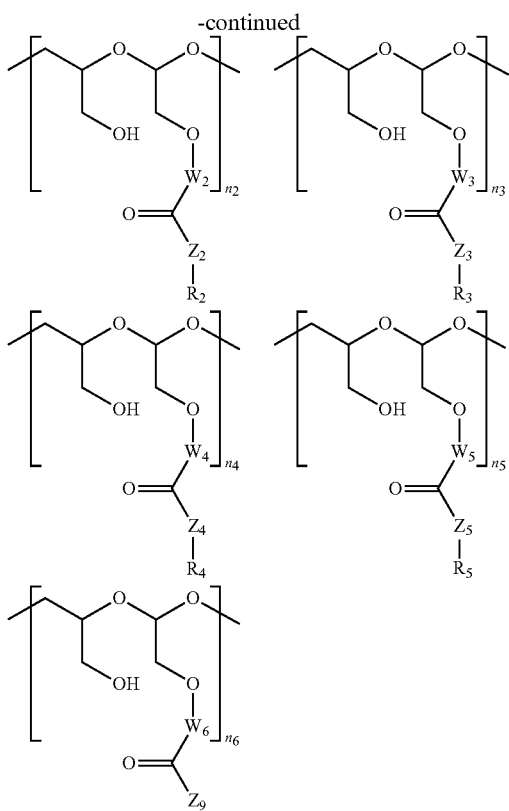

wherein:
each of $W_1$, $W_2$, $W_3$, $W_4$, $W_5$ and $W_6$, independently, is a covalent bond or —C(O)—Y— with —C(O) connected to the polyacetal backbone;
Y is —[C($R_9R_{10}$)]$_a$— or —[C($R_9R_{10}$)]$_a$—$X_1$—[C($R_9R_{10}$)]$_b$—;
$X_1$ is an oxygen atom, a sulfur atom or —$NR_{11}$;
each of $R_9$ and $R_{10}$ independently is hydrogen, $C_{1-6}$ alkyl, $C_{6-10}$ aryl, 5 to 12-membered heteroaryl or $C_{3-8}$ cycloalkyl;
$R_{11}$ is hydrogen, $C_{1-6}$ alkyl, $C_{6-10}$ aryl, 5 to 12-membered heteroaryl, $C_{3-8}$ cycloalkyl or —C(O)—$C_{1-3}$ alkyl;
$Z_9$ is $Z_6$-$T_1$ or $Z_8$;
$T_1$ is —$Z_7$—$R_6$;
$Z_8$ is a linear or branched polyamino moiety substituted with one or more —$Z_7$—$R_6$ and optionally substituted with one or more substituents selected from the group consisting of -Q-$R_1$, -Q-$R_3$, -Q-$R_4$, and -Q-$R_5$;
each Q independently is a covalent bond or —C(O)—;
each of $Z_1$, $Z_2$, $Z_3$, $Z_4$, $Z_5$, and $Z_6$, independently, is a covalent bond, —$NR_{17}$, or —$NR_{17}R_{18}$—, in which each of $R_{17}$ and $R_{18}$ independently is H, $C_{2-8}$ alkyl, or —$C_{2-10}$ alkyl-N($R_x$)—, $R_x$ being H or an amino acid attached to the nitrogen via the carbonyl group of the amino acid; or $R_{17}$ and $R_{18}$, together with the nitrogen atom to which they are attached form a 4 to 7-membered heterocycloalkyl ring containing 0 or 1 additional heteroatom selected from N, O, and S;
each $Z_7$ independently is —C(O)-$T_2$-$T_3$- or —N(R')-$T_2$-$T_3$- with $T_3$ connected to $R_6$, in which R' is H or $C_{1-6}$ alkyl, $T_2$ is selected from alkylthioaryl, arylthioalkyl, alkylthioaryl, arylthioaryl, alkyldithioaryl, aryldithioalkyl, alkyldithioaryl, and aryldithioaryl, and $T_3$ is a covalent bond, —C(O)N(R")—$C_{1-8}$ alkyl, —N(R")C(O)—$C_{1-8}$ alkyl, or $C_{1-8}$ alkyl, in which R" is H or $C_{1-6}$ alkyl;

each of a and b independently is an integer between 1 and 6 inclusive;
each of n, $n_1$, $n_2$, $n_3$, $n_4$, $n_5$, and $n_6$ is the molar fraction of the corresponding polyacetal unit ranging between 0 and 1; n+$n_1$+$n_2$+$n_3$+$n_4$+$n_5$+$n_6$=1; provided that neither n nor $n_6$ is 0;
$R_1$ is a targeting group for a selected tissue, pathogen, cell, or cellular location;
$R_2$ is a charge group optionally substituted with one or more substituents selected from the group consisting of -Q-$R_1$, -Q-$R_3$, -Q-$R_4$, and -Q-$R_5$;
$R_3$ is a charge-modifying group;
$R_4$ is a hydrophobic group;
$R_5$ is a protective group;
$R_6$ is a polynucleotide;
the ratio ($m_1$) of the number of $R_1$ to the total number of polyacetal units of the polyacetal is 0 to 0.25;
the ratio ($m_3$) of the number of $R_3$ to the total number of polyacetal units of the polyacetal is 0 to 100;
the ratio ($m_4$) of the number of $R_4$ to the total number of polyacetal units of the polyacetal is 0 to 30;
the ratio ($m_5$) of the number of $R_5$ to the total number of polyacetal units of the polyacetal is 0 to 0.03;
the ratio ($m_6$) of the number of $R_6$ to the total number of polyacetal units of the polyacetal is 0.0004 to 0.10; and
the polyacetal backbone has a molecular weight of about 10 kDa to about 250 kDa.
For example, Y is —$(CH_2)_2$— or —$(CH_2)_3$—.
For example, $T_2$ is —$C_{1-8}$ alkylthio-$C_{6-10}$ aryl, —$C_{6-10}$ arylthio-$C_{1-8}$ alkyl, —$C_{1-8}$ alkylthio-$C_{1-8}$alkyl, —$C_{6-10}$ arylthio-$C_{6-10}$ aryl, —$C_{1-8}$ alkyldithio-$C_{6-10}$ aryl, —$C_{6-10}$ aryldithio-$C_{1-8}$alkyl, —$C_{1-8}$alkyldithio-$C_{1-8}$alkyl, or —$C_{6-10}$ aryldithio-$C_{6-10}$ aryl.
For example, $m_1$ is 0.002 to 0.25.
For example, $m_3$ is 0.002 to 100.
For example, $m_4$ is 0.03 to 0.30.
For example, $m_5$ is 0.01 to 0.03.
For example, when $Z_9$ is $Z_6$-$T_1$,
(i) $n_1$ is not 0 and each of $n_2$, $n_3$, $n_4$, and $n_5$ is 0;
(ii) neither $n_1$ nor $n_2$ is 0 and each of $n_3$, $n_4$, and $n_5$ is 0;
(iii) none of $n_1$, $n_2$ and $n_3$ is 0 and each of $n_4$ and $n_5$ is 0;
(iv) none of $n_1$, $n_2$ and $n_4$ is 0 and each of $n_3$ and $n_5$ is 0;
(v) none of $n_1$, $n_2$, $n_3$ and $n_4$ is 0 and $n_5$ is 0;
(vi) neither $n_1$ nor $n_4$ is 0 and each of $n_2$, $n_3$ and $n_5$ is 0;
(vii) $n_2$ is not 0 and each of $n_1$, $n_3$, $n_4$, and $n_5$ is 0;
(viii) neither $n_2$ nor $n_3$ is 0 and each of $n_1$, $n_4$ and $n_5$ is 0;
(ix) neither $n_2$ nor $n_4$ is 0 and each of $n_1$, $n_3$ and $n_5$ is 0;
(x) none of $n_2$, $n_3$ and $n_4$ is 0 and each of $n_1$ and $n_5$ is 0;
(xi) none of $n_1$, $n_2$, $n_3$, $n_4$, and $n_5$ is 0; or
(xii) each of $n_1$, $n_2$, $n_3$, $n_4$, and $n_5$ is 0.
For example, when $Z_9$ is $Z_6$-$T_1$:
(i) $n_2$ is not 0 and each of $n_1$, $n_3$, $n_4$, and $n_5$ is 0;
(ii) none of $n_1$, $n_2$ and $n_4$ is 0 and each of $n_3$ and $n_5$ is 0; or
(iii) none of $n_1$, $n_2$, $n_3$ and $n_4$ is 0 and $n_5$ is 0.
For example, when $Z_9$ is $Z_6$-$T_1$,
n is a between about 0.01 and about 0.9996 inclusive (e.g., between about 0.10 and about 0.80 inclusive; between about 0.30 and 0.45 inclusive; between about 0.30 and 0.40 inclusive; between about 0.45 and 0.97 inclusive; between about 0.51 and 0.95 inclusive; between about 0.65 and 0.998 inclusive; between about 0.72 and 0.998 inclusive; between about 0.92 and 0.9996 inclusive or between about 0.998 and 0.9994 inclusive);
$n_1$ is between about 0.002 and about 0.25 inclusive;
$n_2$ is between about 0.02 and about 0.90 inclusive (e.g., between about 0.02 and about 0.81 inclusive; between about 0.16 and about 0.49 inclusive; between about 0.16 and about 0.90 inclusive or between about 0.55 and about 0.70 inclusive);

$n_3$ is between about 0.02 and about 0.81 inclusive (e.g., between about 0.16 and about 0.49 inclusive);

$n_4$ is between about 0.03 and about 0.30 inclusive (e.g., between about 0.05 and about 0.15 inclusive);

$n_5$ is between about 0.01 and about 0.03 inclusive (e.g., about 0.02); and $n_6$ is between about 0.0004 and about 0.10 inclusive (e.g., between about 0.0006 and about 0.002 inclusive).

For example, when $Z_9$ is $Z_8$, each of $n_1$, $n_3$, $n_4$, and $n_5$ is 0, and $R_2$ is a linear or branched polyamino moiety optionally substituted with one or more substituents selected from the group consisting of -Q-$R_f$, -Q-$R_3$, -Q-$R_4$, and -Q-$R_5$.

For example, each of -Q-$R_f$, -Q-$R_3$, -Q-$R_4$, and -Q-$R_5$ is attached to a N atom of $R_2$.

For example, each of —$Z_7$—$R_6$, -Q-$R_1$, -Q-$R_3$, -Q-$R_4$, and -Q-$R_5$ is attached to a N atom of $Z_8$.

For example, when $Z_9$ is $Z_8$, (i) $m_1$ is not 0 and each of $m_3$, $m_4$ and $m_5$ is 0;

(ii) neither $m_1$ nor $m_4$ is 0 and each of $m_3$ and $m_5$ is 0;

(iii) none of $m_1$, $m_4$ and $m_5$ is 0 and $m_3$ is 0;

(iv) neither $m_1$ nor $m_3$ is 0 and each of $m_4$ and $m_5$ is 0;

(v) none of $m_1$, $m_3$ and $m_4$ is 0 and $m_5$ is 0; or (vi) none of $m_1$, $m_3$, $m_4$ and $m_5$ is 0.

For example, when $Z_9$ is $Z_8$, n is between about 0.70 and about 0.99 inclusive (e.g., between about 0.80 and about 0.99 inclusive or between about 0.92 and about 0.98 inclusive); $n_2+n_6$ is between about 0.10 and about 0.30 inclusive (e.g., between about 0.10 and about 0.20 inclusive or between about 0.02 and about 0.08 inclusive); each of $n_1$, $n_3$, $n_4$, and $n_5$ is 0;

$m_1$ is 0.002 to 0.25;

$m_3$ is 0.002 to 100;

$m_4$ is 0.03 to 0.30;

$m_5$ is 0.01 to 0.03; and $m_6$ is 0.0004 to 0.10.

For example, each of $Z_1$, $Z_2$, $Z_3$, $Z_4$, $Z_5$, and $Z_6$, independently, can be ethylenediamine, piperazine, bis(piperidine), 1,3-diaminopropane, 1,4-diaminobutane (i.e., putrescine), decamethylenediamine, hexamethylenediamine, cadaverine, lysine, histidine, arginine, tryptophan, agmatine or ornithine.

For example, each of $R_1$, $R_2$, $R_3$, $R_4$, $R_5$, and $T_1$ is attached to a N atom of $Z_1$, $Z_2$, $Z_3$, $Z_4$, $Z_5$, and $Z_6$ respectively and the N atom is not that of the amide moiety via which $Z_1$, $Z_2$, $Z_3$, $Z_4$, $Z_5$, or $Z_6$ is attached to the polyacetal backbone For example, each of $Z_1$, $Z_2$, $Z_3$, $Z_4$, $Z_5$, and $Z_6$ is

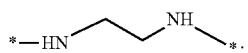

For example, when each of $Z_1$, $Z_2$, $Z_3$, $Z_4$, $Z_5$, and $Z_6$, independently, is ethylenediamine the modified acetal units are represented by Formula (VII) or (VIII):

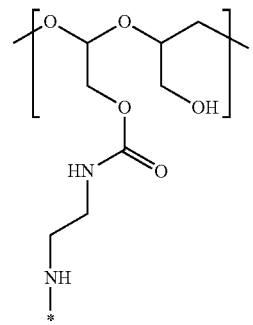
(VII)

and

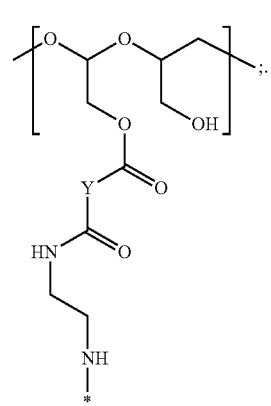
(VIII)

In Formula (VII) the ethylenediamine moiety is directly linked to the hydroxyl group of the acetal unit via a carbamate bond through a nitrogen atom of the ethylenediamine moiety; and in Formula (VIII) the ethylenediamine moiety is linked indirectly to the hydroxyl group of the acetal unit via a dicarboxylic acid compound in which one carboxylic group is linked to the nitrogen atom of the ethylenediamine moiety via an amide bond and the other carboxylic group is linked to the hydroxyl group of the acetal unit via an ester bond.

For example, $Z_7$ is

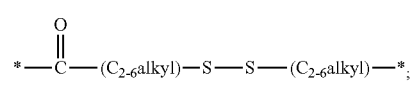
(1)

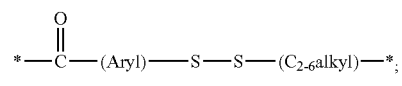
(2)

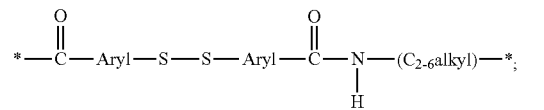
(3)

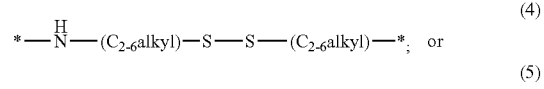
(4)

or

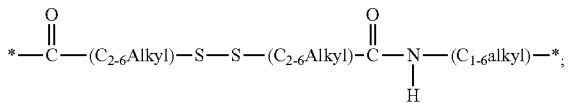
(5)

wherein —C(O) or —NH is oriented towards the polyacetal backbone.

For example, $Z_7$ is

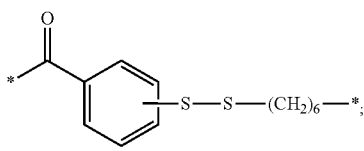 (1)

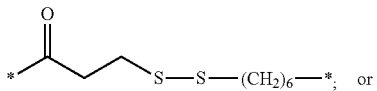 (2)

or

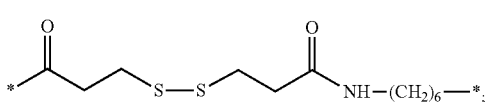 (3)

wherein —C(O) is oriented towards the polyacetal backbone.

For example, $Z_8$, when otherwise unsubstituted, is

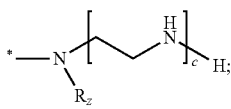 (1)

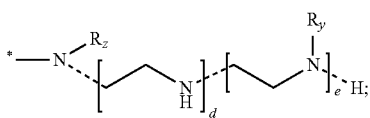 (2)

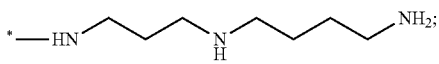 (3)

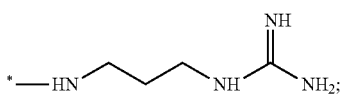 (4)

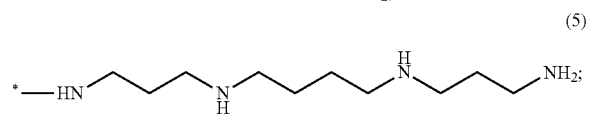 (5)

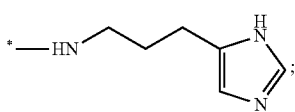 (6)

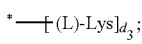 (7)

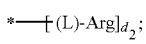 (8)

or
(9) a dendrimer of any of generations 2-10 selected from poly-L-lysine, poly(propyleneimine) and poly(amidoamine) dendrimers;
wherein:
$R_y$ is an amino acid attached to the nitrogen via the carbonyl group of the amino acid or a linear or branched polyamino moiety;
$R_z$ is H or a linear or branched polyamino moiety;
c is an integer between 2 and 600 inclusive;
d is an integer between 0 and 600 inclusive;
e is an integer between 1 and 150 inclusive;
$d_2$ is an integer between 2 and 20 inclusive; and
$d_3$ is an integer between 2 and 200 inclusive.

For example, $Z_8$, when otherwise unsubstituted, is (1) a linear polyethylenimine having a molecular weight of about 500 to about 25000 dalton (e.g., about 500 to about 5000 dalton; or about 500 to about 2500 dalton); (2) a branched polyethylenimine having a molecular weight of about 500 to about 25000 dalton (e.g., about 500 to about 1500 dalton, or about 500 to about 1200 dalton, or about 500 to about 800 dalton);

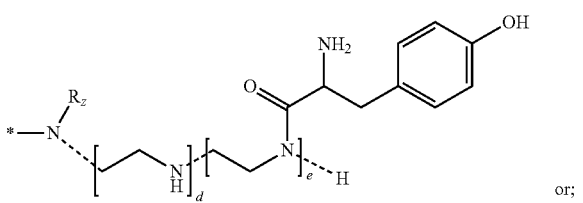 (3)

or;

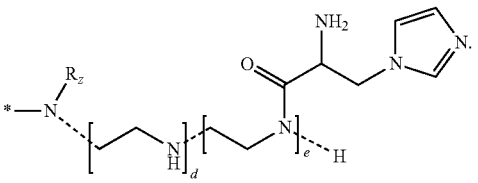 (4)

For example, each of $R_y$ and $R_z$, independently, is a polyamino moiety comprising a monomer unit of —[$C_{2-6}$ alkyl-NH]—.

For example, $Z_8$ is diethylenetriamine, triethylenetetramine, tetraethylenepentamine, pentaethylenehexamine, linear polyethylenimine, branched polyethylenimine, spermine, spermidine, norspermidine, polylysine, polyarginine or amino containing dendrimers.

For example, when unsubstituted $Z_8$ is a linear or branched polyethylenimine, the modified acetal units are represented by Formula (IX) or (X):

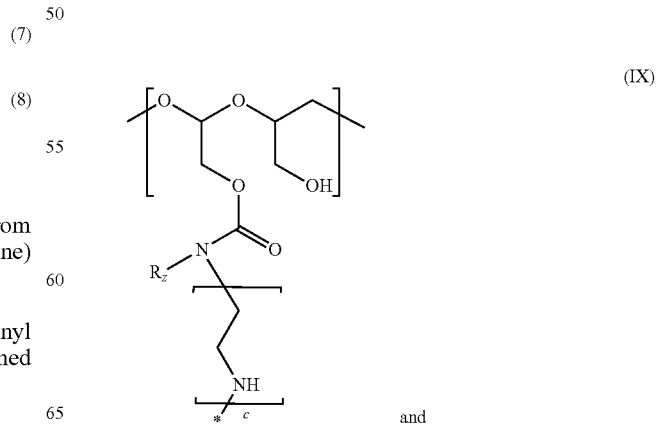 (IX)

and

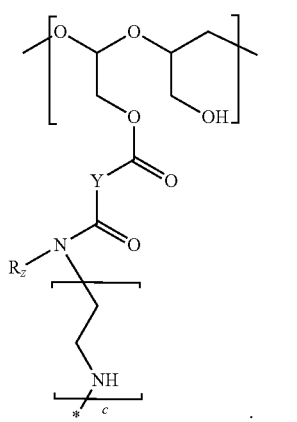 (X)

In Formula (IX), the linear or branched polyethylenimine moiety is directly linked to the hydroxyl group of the acetal unit via a carbamate bond through a nitrogen atom of the ethylenediamine, linear or branched polyethylenimine moiety, while in Formula (X), the linear or branched polyethylenimine moiety is linked indirectly to the hydroxyl group of the acetal unit via a dicarboxylic acid compound in which one carboxylic group is linked to the nitrogen atom of the linear or branched polyethylenimine moiety via an amide bond and the other carboxylic group is linked to the hydroxyl group of the acetal unit via an ester bond; and $R_z$ and c are as defined herein.

Targeting Groups $R_1$

Targeting groups $R_1$ direct the modified polymers to specific tissues, cells, or locations in a cell. In one embodiment, the ratio of modified polymer containing the targeting group that reaches the target to modified polymer without any targeting group is greater than one. In other embodiments, the targeting group provides a target tissue ratio for modified polymer containing the targeting group that is at least 2-fold, at least 5-fold, at least 10-fold, at least 50-fold, or at least 100-fold greater than the target tissue ratio of modified polymer that does not contain the targeting group. In other embodiments, the targeting group provides a target tissue/liver ratio for modified polymer containing the targeting group that is at least 2-fold, at least 5-fold, at least 10-fold, at least 50-fold, or at least 100-fold greater than the target tissue/liver ratio of modified polymer that does not contain the targeting group or vice versa.

The targeting group can direct the modified polymer in culture or in a whole organism, or both. In each case, the targeting group has a ligand that is present on the cell surface of the targeted cell(s) to which it binds with an effective specificity, affinity and avidity. In some embodiments, the targeting group targets the modified polymer to tissues other than the liver. In other embodiments the targeting group targets the modified polymer to a specific tissue such as the liver, kidney, lung or pancreas. The targeting group can target the modified polymer to a target cell such as a cancer cell, such as a receptor expressed on a cell such as a cancer cell, a matrix tissue, or a protein associated with cancer such as tumor antigen. Alternatively, cells comprising the tumor vasculature may be targeted. Targeting groups can direct the polymer to specific types of cells such as specific targeting to hepatocytes in the liver as opposed to Kupffer cells. In other cases, targeting groups can direct the polymer to cells of the reticular endothelial or lymphatic system, or to professional phagocytic cells such as macrophages or eosinophils. (In such cases the polymer itself might also be an effective delivery system, without the need for specific targeting).

In still other embodiments, the targeting group can target the modified polymer to a location within the cell, such as the nucleus, the cytoplasm, or the endosome, for example. In specific embodiments, the targeting group can enhance cellular binding to receptors, or cytoplasmic transport to the nucleus and nuclear entry or release from endosomes or other intracellular vesicles.

The targeting group can be a protein, peptide, lipid, steroid, sugar, carbohydrate, polynucleotide, antibody, or synthetic compound. Exemplary targeting groups include groups with affinity to cell surface molecules, as well as cell receptor ligands (naturally occurring or synthetic), antibodies, antibody fragments, and antibody mimics with affinity to cell surface molecules.

In one embodiment, the targeting group comprises a cell receptor ligand. A variety of ligands have been used to target drugs and genes to cells and to specific cellular receptors. Cell receptor ligands include, for example, carbohydrates, glycans, saccharides (including, but not limited to: galactose, galactose derivatives, mannose, and mannose derivatives), vitamins, folate, biotin, aptamers, and peptides (including, but not limited to: RGD-containing peptides, insulin, EGF, and transferrin). Examples of targeting groups include those that target the asialoglycoprotein receptor by using asialoglycoproteins or galactose residues. For example, liver hepatocytes contain ASGP Receptors. Therefore, galactose-containing targeting groups may be used to target hepatocytes. Galactose containing targeting groups include, but are not limited to: galactose, N-acetylgalactosamine, oligosaccharides, and saccharide clusters (such as: Tyr-Glu-Glu-(aminohexyl GalNAc)$_3$, lysine-based galactose clusters, and cholane-based galactose clusters). Further suitable conjugates can include oligosaccharides that can bind to carbohydrate recognition domains (CRD) found on the asialoglycoprotein-receptor (ASGP-R). Example conjugate moieties containing oligosaccharides and/or carbohydrate complexes are provided in U.S. Pat. No. 6,525,031, incorporated herein by reference.

In other embodiments, G protein coupled receptors (GPCRs) are targeted using specific ligands. GPCRs are membrane-spanning receptors expressed on the cell surface, and are often expressed in a tissue specific or restricted manner. A wide variety of GPCR ligands are known, and comprise a large number of both naturally occurring and synthetic molecules. GPCR ligands bind specifically to their cognate receptors with high affinity and upon binding, may activate (agonize) or inactivate (antagonize) signaling of the bound receptor. In other cases, a ligand may not mediate and activating or inactivating signal per se, but by binding a specific GPCR, compete with and/or displace other ligands, naturally occurring or otherwise. In each case, however, association between a GPCR and a cognate ligand, regardless of ligand's origin or intrinsic effect in the signaling activity of the GPCR, represents a highly specific binding event that may be utilized in targeting designated organs or tissues. As such, targeting is achieved by attachment of a GPCR-specific ligand to an agent for which delivery is desired in this manner, the agent is delivered to cells that express the corresponding cognate GPCR.

Antibodies represent another class of molecules that are useful for targeting. The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies may exist in a variety of forms including, for example, polyclonal antibodies, monoclonal antibodies, intracellular antibodies ("intrabodies"), Fv, Fab and F(ab)$_2$, as well as single chain antibodies (scFv), camelid antibodies and humanized antibodies In one embodiment, the antibody binds a receptor on a cell such as a tumor cell. Monoclonal antibodies (Mab's) that bind specifically to tumor-associated antigens have been employed in an attempt to target toxin, radionucleotide, and chemotherapeutic conjugates to tumors. To date, a variety of monoclonal antibodies have been developed that induce cytolytic activity against tumor cells. Additional antibodies or ligands have been discovered that interact specifically with antigens present on tumor cells. For example, a humanized version of the monoclonal antibody MuMAb4D5, directed to the extracellular domain of P185, growth factor receptor (HER2), is used to treat human breast cancer. In another embodiment, the cell is a B lymphocyte, the antibody can be against the cell receptor CD19, CD20, CD21, CD23, CD39, CD40 or a ligand to these receptors.

Antibodies may be directed against cell-specific antigens, receptors expressed on specific cell types, or against antigens that are specifically expressed by pathogen-infected cells. In the latter case, such antigens would also include those encoded or expressed by the infectious agent.

In another embodiment, the targeting group is an aptamer. Aptamers are nucleic acid or peptide molecules that bind to a specific target molecule. Aptamers can be determined by selecting them from a large random sequence pool. Nucleic acid aptamers are nucleic acid species that have been engineered through repeated rounds of in vitro selection or equivalently, SELEX (systematic evolution of ligands by exponential enrichment) to bind to various molecular targets such as small molecules, proteins, nucleic acids, and even cells, tissues and organisms. Nucleic acid aptamers having specific binding affinity to molecules through interactions including Watson-Crick base pairing and non-Watson-Crick base pairing. Peptide aptamers are proteins that are designed to interfere with other protein interactions inside cells. They consist of a variable peptide loop attached at both ends to a protein scaffold. This double structural constraint greatly increases the binding affinity of the peptide aptamer to levels comparable to an antibody's (nanomolar range). Peptide aptamer selection can be made using different systems, such as the yeast two-hybrid system.

In one embodiment, the targeting group is a transduction domain such as a viral transduction domain. As used herein, transduction domains transport themselves and attached molecules across membranes. Examples of these transduction signals are derived from viral coat proteins such as Tat from HIV and VP22 from herpes simplex virus, and a transcriptional factor from Drosophila, ANTP. In addition, reports of synthetic peptides possessing no homology other than net overall cationic charge have also been shown to possess transduction activity.

Other targeting groups can be used to increase the delivery of the polynucleotide to certain parts of the cell. For example, targeting groups can be used to disrupt endosomes and a nuclear localizing signal (NLS) can be used to target the nucleus. A variety of ligands have been used to target drugs and genes to cells and to specific cellular receptors. The ligand can seek a target within the cell membrane, on the cell membrane or near a cell. Binding of ligands to receptors typically initiates endocytosis. Ligands that bind to receptors that are not endocytosed could also be used for polynucleotide delivery. For example peptides containing the RGD peptide sequence that bind the integrin receptor could be used. In addition viral proteins could be used to bind the complex to cells. Lipids and steroids could be used to directly insert a complex into cellular membranes. The polymers can also contain cleavable groups within themselves. When attached to the targeting group, cleavage leads to reduced interaction between the complex and the receptor for the targeting group. Cleavable groups include but are not restricted to disulfide bonds, diols, diazo bonds, ester bonds, sulfone bonds, acetals, ketals, enol ethers, enol esters, enamines and imines, acyl hydrazones, and Schiff bases.

Nuclear localizing targeting groups enhance the targeting of the gene into proximity of the nucleus and/or its entry into the nucleus. Such nuclear transport signals can be a protein or a peptide such as the SV40 large T antigen NLS or the nucleoplasmin NLS. These nuclear localizing signals interact with a variety of nuclear transport factors such as the NLS receptor (karyopherin alpha), which then interacts with karyopherin beta. The nuclear transport proteins themselves could also function as NLS's since they are targeted to the nuclear pore and nucleus.

Targeting groups that enhance release from intracellular compartments (releasing targeting groups) can cause polynucleotide release from intracellular compartments such as endosomes (early and late), lysosomes, phagosomes, vesicles, endoplasmic reticulum, golgi apparatus, trans golgi network (TGN), and sarcoplasmic reticulum. Release includes movement out of an intracellular compartment into the cytoplasm or into an organelle such as the nucleus. Releasing signals include chemicals such as chloroquine, bafilomycin or Brefeldin A1 and the ER-retaining signal, viral components such as influenza virus hemaglutinin subunit HA-2 peptides and other types of amphipathic peptides. Cellular receptor signals are signals that enhance the association of the modified polymer with a cell. This can be accomplished by either increasing the binding of the modified polymer to the cell surface and/or its association with an intracellular compartment, for example: ligands that enhance endocytosis by enhancing binding to the cell surface. This includes agents that target to the asialoglycoprotein receptor by using asialoglycoproteins or galactose residues. Other proteins such as insulin, EGF, or transferrin can be used for targeting. Chemical groups that react with sulfhydryl or disulfide groups on cells can also be used to target many types of cells. Folate and other vitamins can also be used for targeting. In addition viral proteins could be used to bind cells.

Reporter or marker molecules are compounds that can be easily detected. Typically they are fluorescent compounds such as fluorescein, rhodamine, Texas red, cy 5, cy 3 or dansyl compounds. They can be molecules that can be detected by UV or visible spectroscopy, by antibody interactions, or by electron spin resonance. Biotin is another reporter molecule that can be detected by labeled avidin. Biotin could also be used to attach targeting groups.

In one embodiment more than one type of targeting group $R_1$ is used in one modified polymer. In this embodiment each type of targeting group $R_1$ is individually attached to the polymer backbone via a linker group $L_1$ of the same or different composition. In one embodiment each of the targeting groups $R_1$ is directly linked to the polymer backbone via a carbamate bond. In another embodiment each of the targeting groups $R_1$ is attached to the polymer backbone via a linker group $L_1$.

In another embodiment each of the targeting groups $R_1$ comprise saccharides such as, for example, galactose, galactose derivatives, galactosamine, N-acetylgalactosamine, mannose, mannose derivatives, -Glu-Glu-(aminohexyl Gal-NAc)$_3$, lysine-based galactose clusters, and cholane-based galactose clusters, and the like; vitamins, such as, for example, biotin, folic acid, Vitamin B$_{12}$, Vitamin E, Vitamin A, and the like; peptides or peptide mimics, such as, for example, integrin targeting peptides (RGD peptides), LHRH receptor targeting peptides, ErbB2 (HER2) receptor targeting peptides, prostate specific membrane bound antigen (PSMA) targeting peptides, lipoprotein receptor LRP1 targeting, ApoE protein derived peptides, ApoA protein peptides, somatostatin receptor targeting peptides, chlorotoxin derived peptides, bombesin, and the like; proteins, such as, for example, insulin, transferrin, fibrinogen-gamma fragment, thrombospondin, claudin, apolipoprotein E, and the like; antibodies or antibody derived Fab, Fab2, scFv or camel antibody heavy-chain fragments specific to the cell surface markers, such as, for example, CD19, CD22, CD25, CD30, CD31, CD33, CD54, CD56, CD62E, CD62P, CD62L, CD70, CD138, CD141, CD326, EGFR, ErbB2, ErbB3, IGF1R, VEGFR1, EphA2, 5T4, TRPV1, CFTR, gpNMB, CA9, Cripto, ACE, APP, adrenergic receptor-beta2, Claudine 3, Mesothelin, IL-2 receptor, IL-4 receptor, IL-13 receptor, integrins (including $\alpha v\beta 3$, $\alpha v\beta 5$, $\alpha v\beta 6$, $\alpha 1\beta 4$, $\alpha 4\beta 1$, $\alpha 5\beta 1$, $\alpha 6\beta 4$ intergins), and the like; aptamers specific to the cell surface markers such as, for example, CD19, CD22, CD25, CD30, CD31, CD33, CD54, CD56, CD62E, CD62P, CD62L, CD70, CD138, CD141, CD326, EGFR, ErbB2, ErbB3, IGF1R, VEGFR1, EphA2, 5T4, TRPV1, CFTR, gpNMB, CA9, Cripto, ACE, APP, adrenergic receptor-beta2, Claudine 3, Mesothelin, IL-2 receptor, IL-4 receptor, IL-13 receptor, integrins (including $\alpha v\beta 3$, $\alpha v\beta 5$, $\alpha v\beta 6$, $\alpha 1\beta 4$, $\alpha 4\beta 1$, $\alpha 5\beta 1$, $\alpha 6\beta 4$ intergins), and the like.

In yet another embodiment each of the of the targeting groups $R_1$ comprise galactosamine, N-acetylgalactosamine, folic acid, RGD peptides, LHRH receptor targeting peptides, ErbB2 (HER2) receptor targeting peptides, prostate specific membrane bound antigen (PSMA) targeting peptides, lipoprotein receptor LRP1 targeting, ApoE protein derived peptides or transferrin.

In some embodiments, the targeting group $R_1$ is:

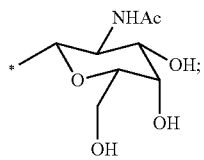
(1)

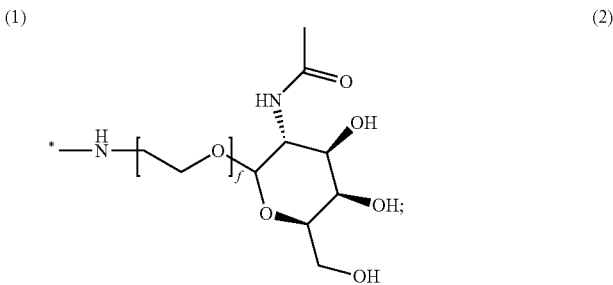
(2)

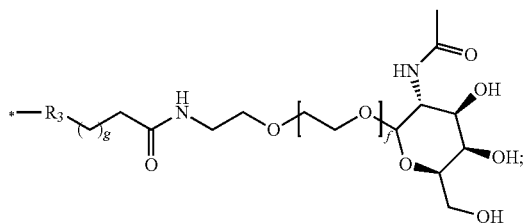
(3)

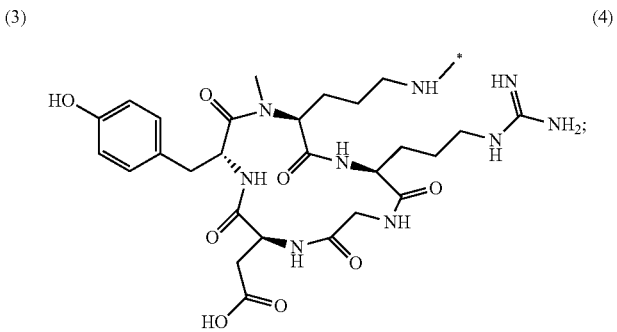
(4)

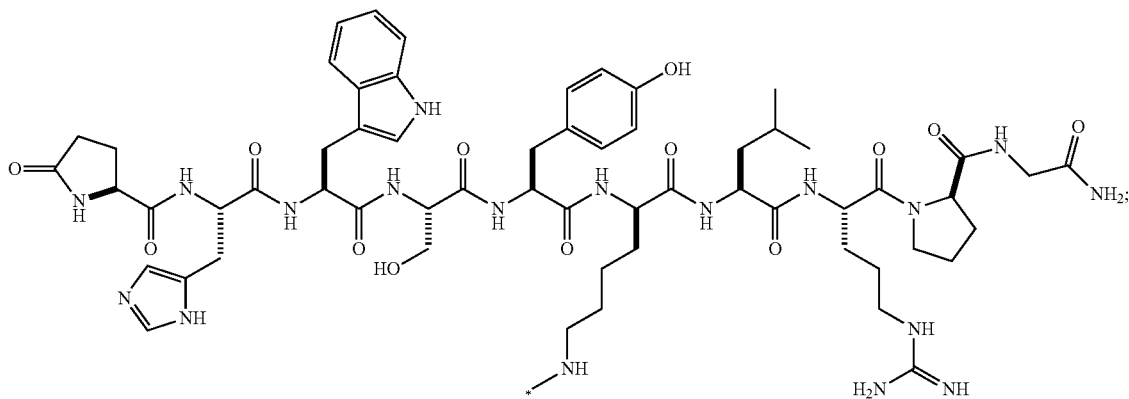

(5)

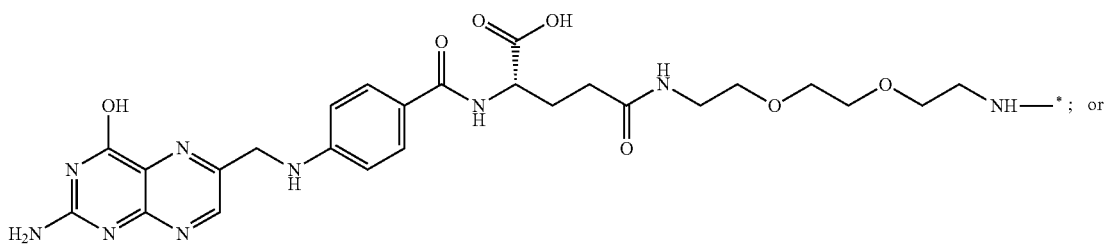

(6)

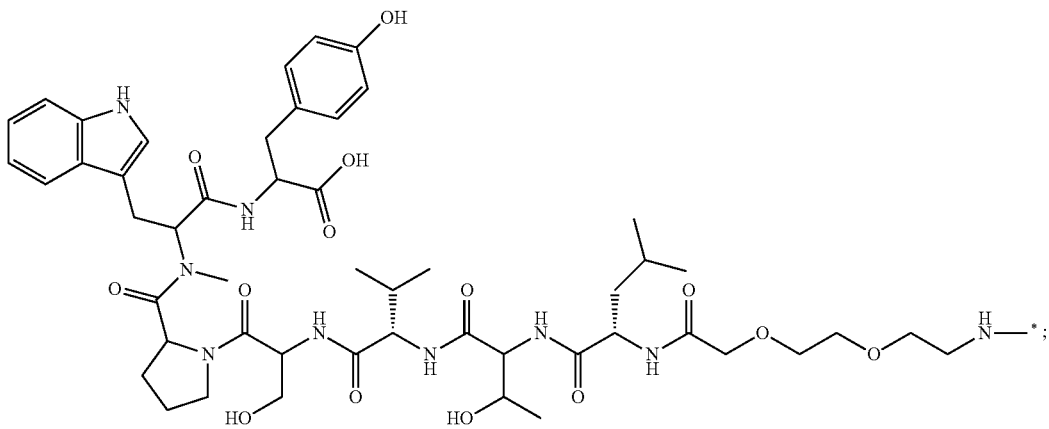

(7)

wherein:

f is an integer between 2 and 24 inclusive;
g is an integer between 1 and 5 inclusive; and
$R_3$ is a charge modifying group;

In one embodiment, f is selected as an integer between 2 and 12 inclusive. In another embodiment, f is selected as an integer between 2 and 6 inclusive. In yet another embodiment, f is 2 or 3.

Targeting group $R_1$ can be attached to $Z_1$ directly or via a multivalent linker group. In one embodiment where the targeting group $R_1$ connects to $Z_1$ via a multivalent linker, $R_1$ and the multivalent linker together can be considered as targeting group $R_1'$ which is represented by Formula (XI):

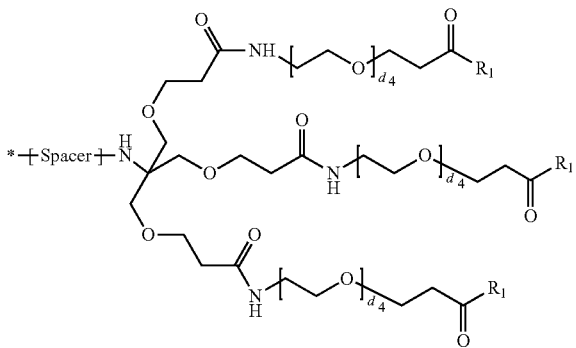

(XI)

wherein:

$d_4$ is an integer between 0 and 120 inclusive; and

Spacer is —$SR_{19}$—C(O)—, C(O)—$C_{1-6}$ alkyl-S—$SR_{19}$—C(O)—, —$C_{1-6}$ alkyl-S—$SR_{19}$—C(O)—, or N(H)$R_{19}$—C(O)— with the leftmost atom of the Spacer connected to $Z_1$, in which $R_{19}$ is a $C_{1-20}$ alkyl linker optionally having one or more of the carbon atoms replaced with O, S, NH, C(O), or C(=NH), or $R_{19}$ is a carbonyl activated PEG moiety wherein the PEG has a molecular weight from about 500 kDa to about 5000 kDa.

For example, $R_1$ of Formula (XI) is:

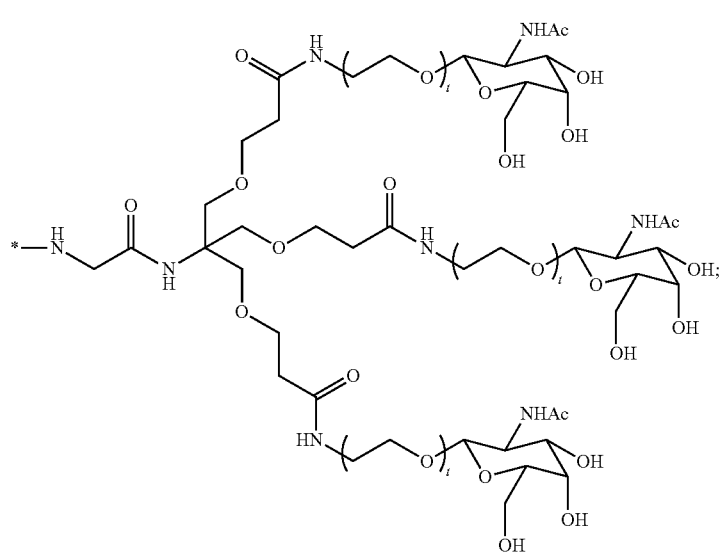

(1)

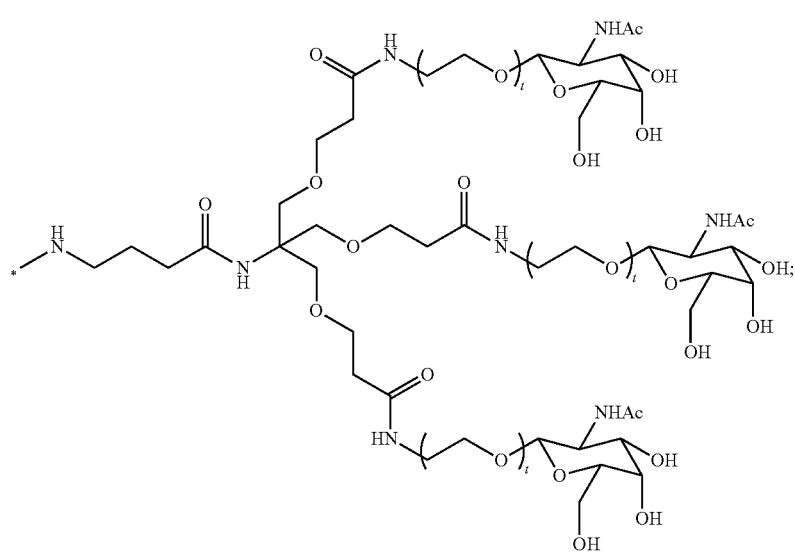

(2)

-continued
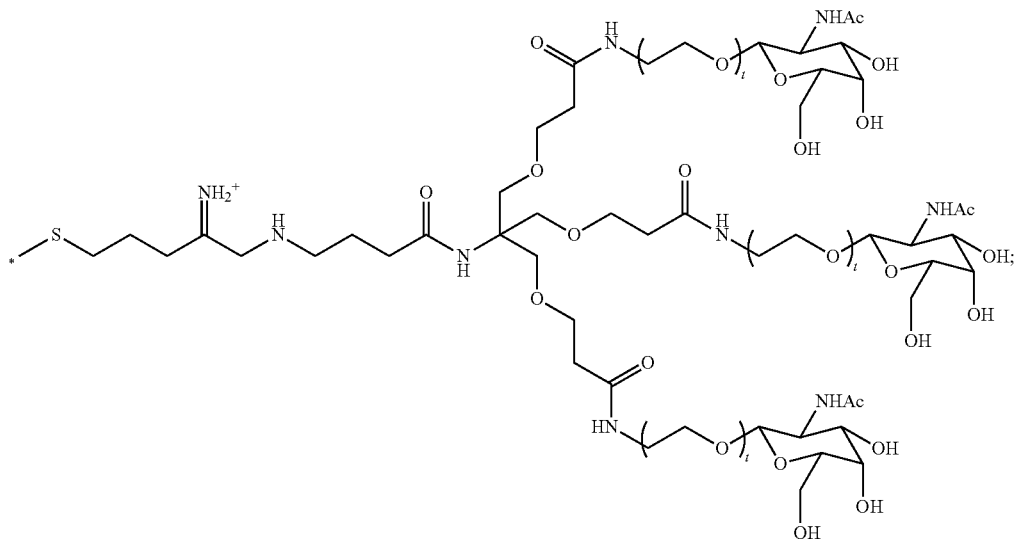
(3)
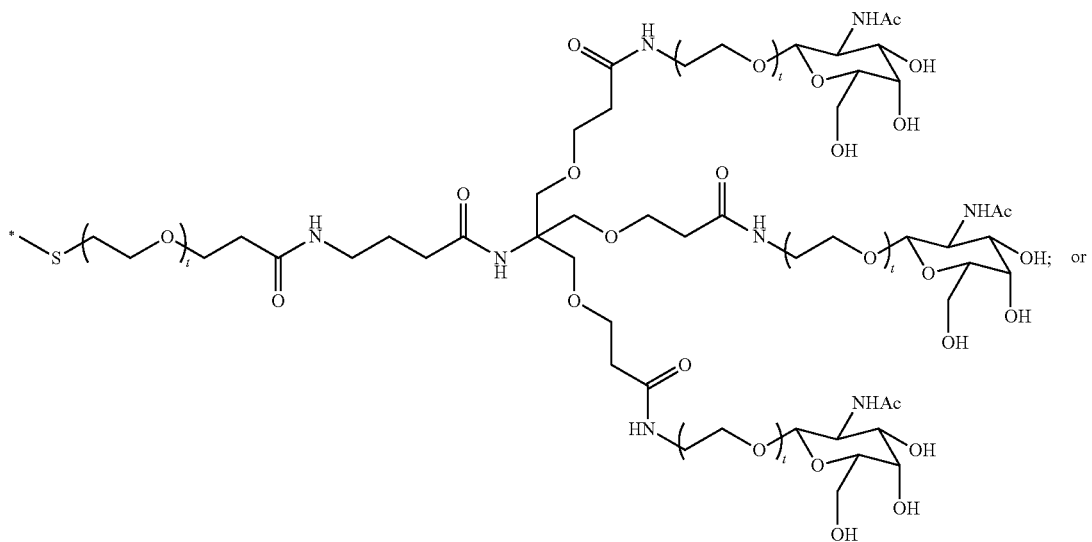
(4)
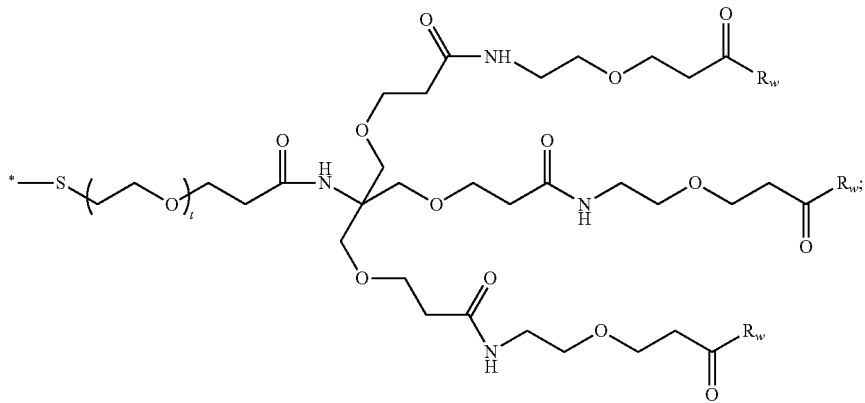
(5)

(6)
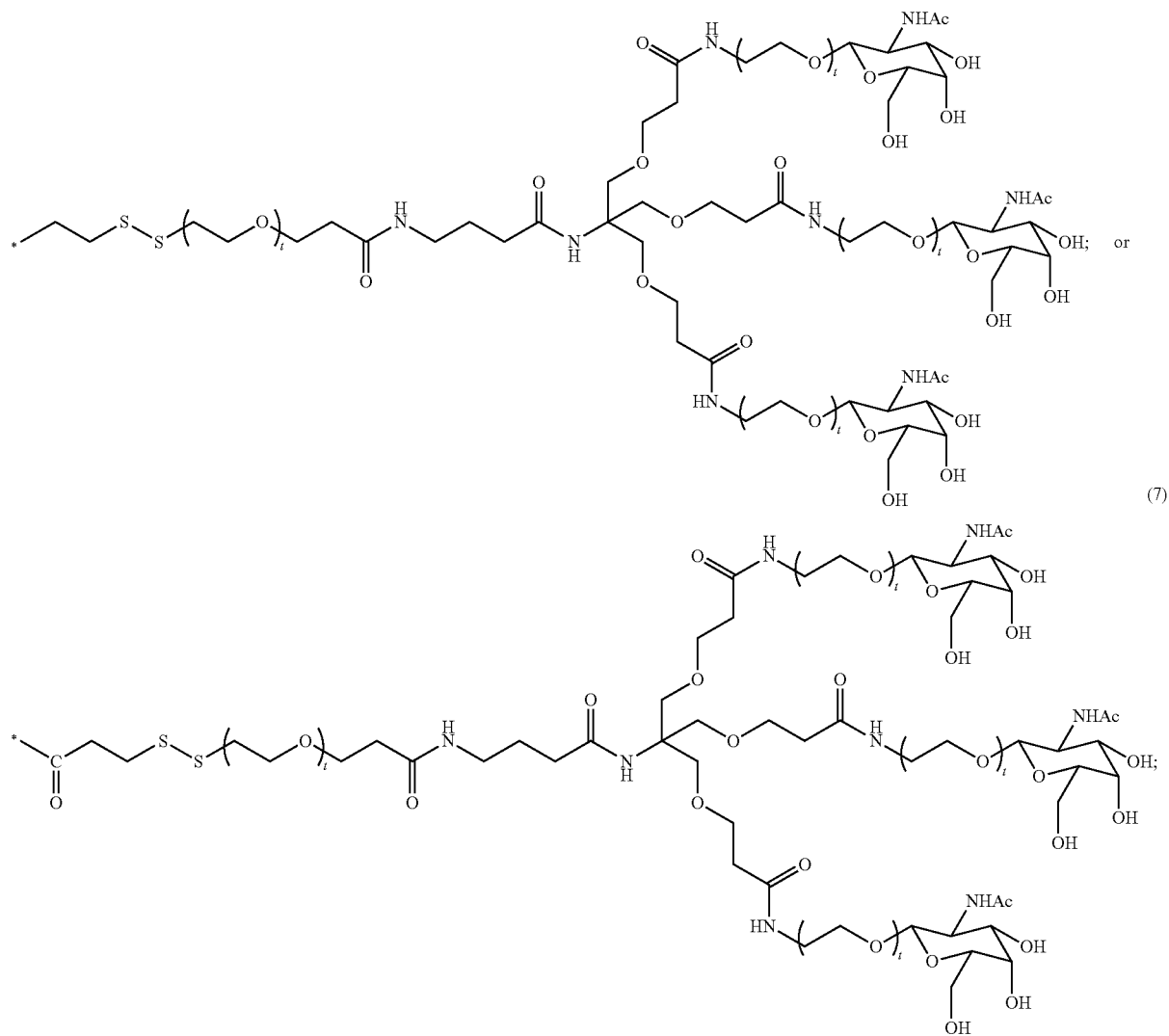
(7)
wherein:
each t, independently, is an integer between 3 and 12 inclusive; and
$R_w$ is:
(1)
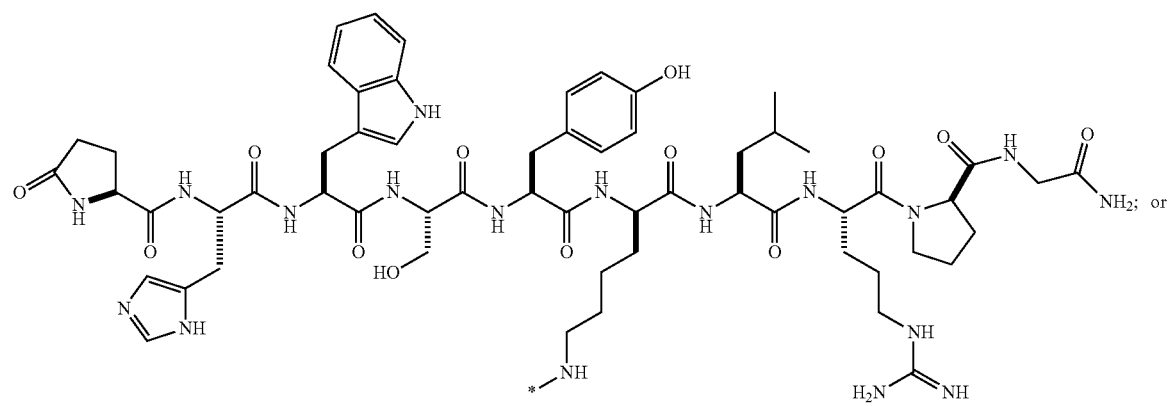

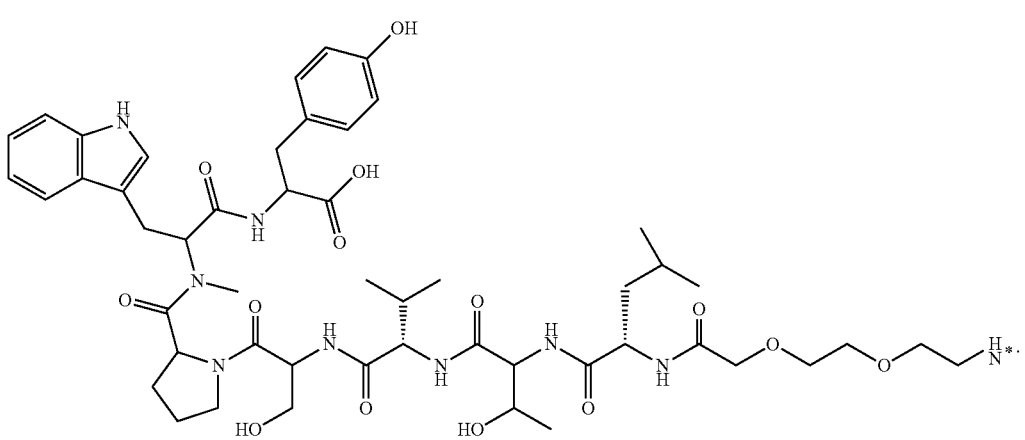

(2)

The type of targeting group and the amount of the targeting group in the modified polymer is selected so as to provide a larger quantity of the modified polymer to the desired target than would be provided in the absence of targeting group. In any of the embodiments herein, $n_1$ can be 0, i.e. no targeting group is incorporated, or $n_1$ can be between about 0.002 and about 0.25 inclusive based on the molar fraction of targeting groups in the modified polymer.

Charged Groups $R_2$: Cationic Group, Anionic Groups, and Ampholytic Groups

Cationic and/or anionic groups $R_2$ can be appended to the polymer backbone to introduce additional charge, or to neutralize charge already present in the modified polymer. These groups can thus be used to form a polymer with a desired net charge or zeta potential.

Exemplary cationic groups comprise lysine, ethylenediamine, diethylenetriamine, triethylenetetramine, tetraethylenepentamine, pentaethylenehexamine, 1,3-diaminopropane, hexamethylenediamine, tetraethylmethylenediamine, linear polyethylenimine, branched polyethylenimine, spermine, spermidine, norspermidine, putrescine, cadaverine, agmatine, arginine, ornithine or 1-(3-aminopropyl)imidazole.

Exemplary anionic groups include aspartate, glutamate, citrate, and malate.

Exemplary ampholytes include amino acids, other than anionic or cationic amino acids, such as glycine, N-methylglycine (sarcosine), trimethylglycine hydroxide inner salt (betaine), alanine, β-alanine, valine, leucine, nor-leucine, isoleucine, serine, threonine, and methionine; dipeptides such as glycylglycine; pharmaceutically acceptable sulfonic acids or derivatives thereof such as taurine; creatinine; and ethylenediaminetetraacetic acid (EDTA).

Cationic and ionic groups can also be appended for other purposes. For example, polycations are multifunctional appended groups that can complex with polynucleotides to protect the polynucleotides against nuclease degradation, to provide attachment of the polynucleotides to the target cell surface. Exemplary polycations include polylysine and polyarginine.

A specific polyanion is polyacrylic acid, which can effect pH-dependent membrane disruption.

A polyampholyte is copolyelectrolyte containing both polycations and polyanions in the same polymer. A specific polyampholyte is a linear oligomer comprising polyethylenimine (PEI) with polymethacrylic acid (PEI-pMAA) and polyglutamic acid (PEI-pGlu). Without being bound by theory, it is believed that the pMAA is situated as an outer shell and functions by inhibiting interactions of the complexes with serum proteins. Polyampholytes have been previously described in U.S. Pat. No. 7,098,030, which is hereby incorporated by reference at Col. 3-14, for its teachings regarding polyampholytes.

In one embodiment more than one type of charged group $R_2$ can be used in one modified polymer. In this embodiment each type of charged group $R_2$ is individually attached to the polymer backbone via a linker group $L_2$ of the same or different composition. The type and amount of each of the cationic groups, anionic groups, and ampholytic groups in the modified polymer is selected so as to provide the desired functionality to the polymer, which will depend on the type and purpose of the group.

In one embodiment, $R_2$ is an amine containing moiety, such as, for example, ethylenediamine, diethylenetriamine, triethylenetetramine, tetraethylenepentamine, pentaethylenehexamine, piperazine, bis(piperidine), 1,3-diaminopropane, 1,4-diaminobutane, tetraethylmethylenediamine, pentaethylenediamine, hexamethylenediamine, linear polyethylenimine, branched polyethylenimine, spermine, spermidine, norspermidine, cadaverine, lysine, histidine, arginine, tryptophan, agmatine, ornithine and 1-(3-aminopropyl)imidazole.

In one embodiment, $R_2$ at each occurrence, independently, is

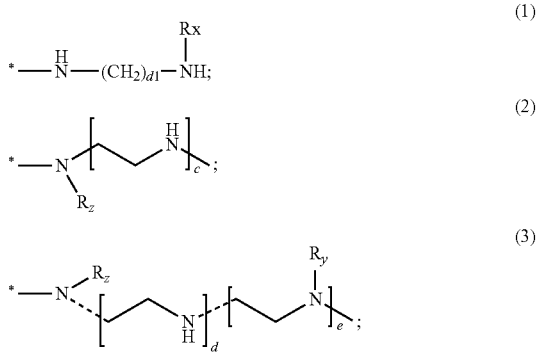

-continued

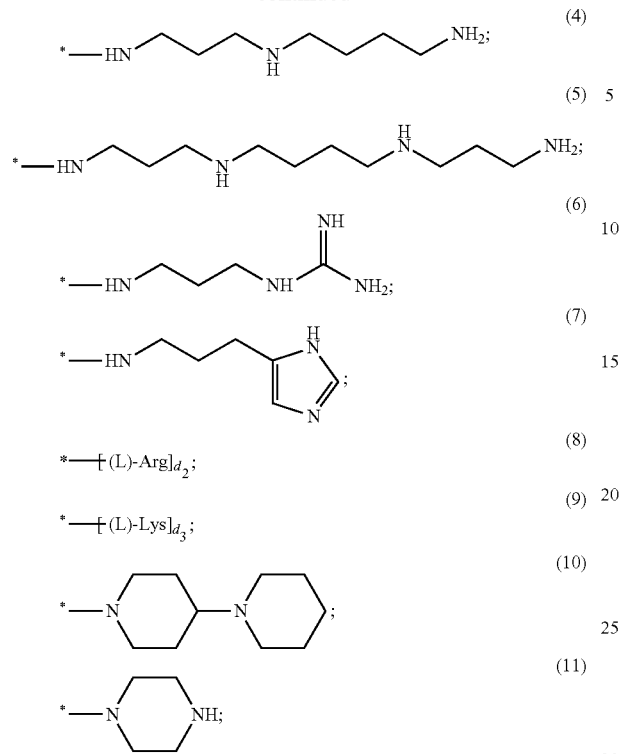

or
(12) a dendrimer of any of generations 2-10, selected from poly-L-lysine, poly(propylene imine) and poly(amido amine) dendrimers;

wherein $R_x$, $R_y$, $R_z$, c, d, e, $d_1$, $d_2$ and $d_3$ are as defined herein.

In some embodiments, $R_2$ at each occurrence, independently, is:

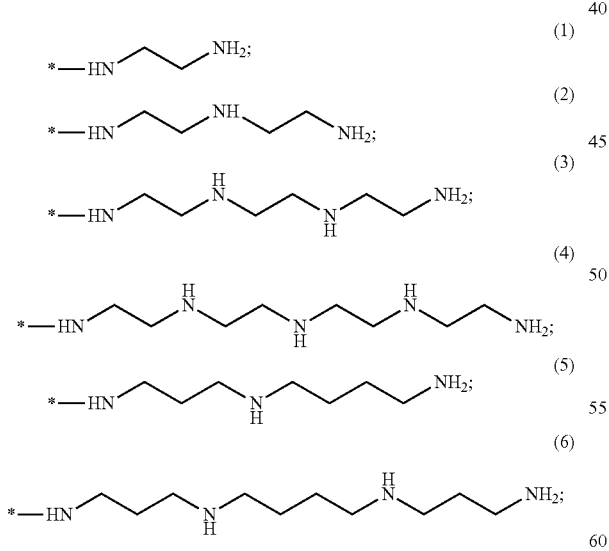

(7) a linear polyethylenimine having a molecular weight of about 500 to about 25000 dalton; or about 500 to about 5000 dalton; or about 500 to 2500 dalton;

(8) a branched polyethylenimine having a molecular weight of about 500 to about 25000 dalton; or about 500 to about 1500 dalton; or about 500 to about 800 dalton;

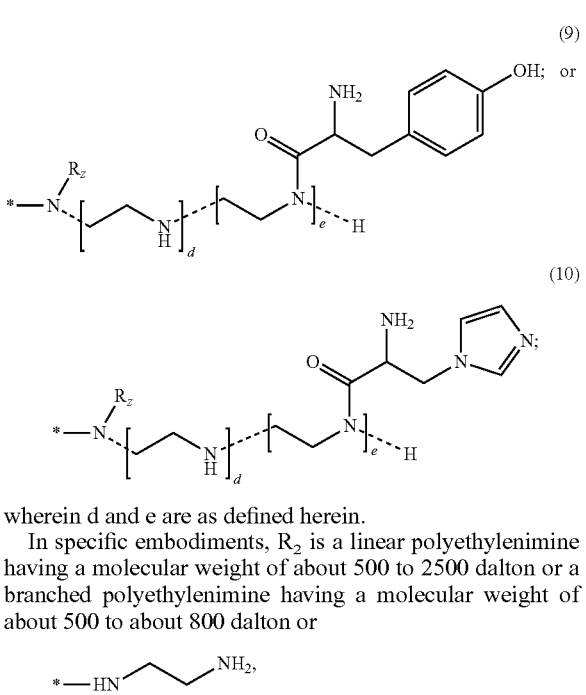

wherein d and e are as defined herein.

In specific embodiments, $R_2$ is a linear polyethylenimine having a molecular weight of about 500 to 2500 dalton or a branched polyethylenimine having a molecular weight of about 500 to about 800 dalton or In one embodiment, $R_2$ is ethylenediamine. In another embodiment the $R_2$ is a linear or branched polyethylenimine. In yet another embodiment the modified acetal units directly linked to ethylenediamine or a linear or branched polyethylenimine are represented by Formula (XII) and Formula (XIII) respectively:

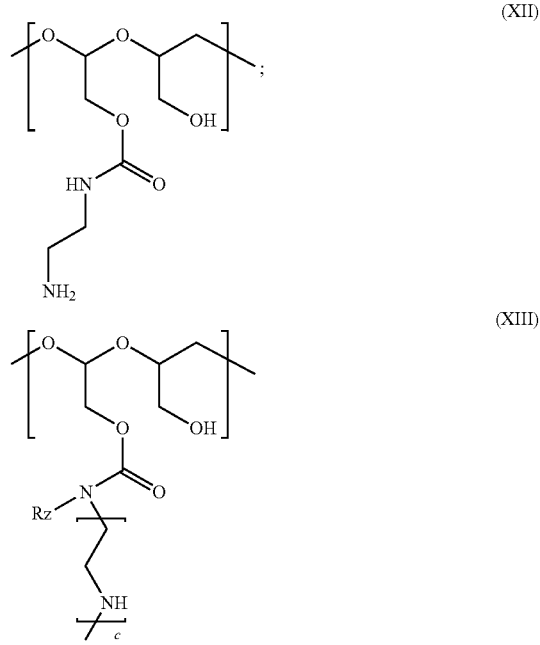

wherein:
$R_z$ and c are as defined herein; and
the ethylenediamine or polyethylenimine moiety is directly linked to the hydroxyl group of the acetal unit via a carbamate bond through a nitrogen atom of the ethylenediamine or polyethylenimine moiety.

In another embodiment the modified acetal units linked to ethylenediamine or a linear or branched polyethylenimine are represented by Formula (XIV) and Formula (XV) respectively:

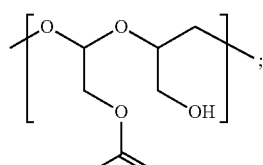

(XIV)

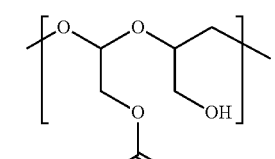

(XV)

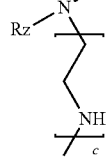

wherein:
Rz, Y and c are as defined herein; and
the ethylenediamine, linear or branched polyethylenimine is indirectly linked to the hydroxyl group of the acetal unit via a dicarboxylic acid compound in which one carboxylic group is linked to the nitrogen atom of the ethylenediamine, linear or branched polyethylenimine via an amide bond and the other carboxylic group is linked to the hydroxyl group of the acetal unit via an ester bond.

In one embodiment, $n_2$ can be 0, i.e. no charged group is incorporated.

In another embodiment, where $Z_9$ is $Z_6$-$T_1$, $n_2$ can be between about 0.02 and about 0.90 inclusive; between about 0.02 and about 0.81 inclusive; between about 0.16 and about 0.49 inclusive; between about 0.16 and about 0.90 inclusive; or between about 0.55 and about 0.70 inclusive; each based on the molar fraction of $R_2$ in the modified polymer. For example, when $R_2$ is ethylenediamine, $n_2$ is between about 0.02 and about 0.90 inclusive; between about 0.02 and about 0.81 inclusive; between about 0.16 and about 0.49 inclusive; between about 0.16 and about 0.90 inclusive or between about 0.55 and about 0.70 inclusive; each based on the molar fraction of ethylenediamine in the modified polymer.

In yet another embodiment, where $Z_9$ is $Z_8$ and each of $Z_8$ and $R_2$ is a polyamino moiety (e.g., a linear or branched polyethylenimine), $n_2$+$n_6$ is between about 0.01 and about 0.30 inclusive; between about 0.010 and about 0.20 inclusive or between about 0.02 and about 0.08 inclusive. In this embodiment, each of $n_1$, $n_3$, $n_4$, and $n_5$ can be 0.

Charge Modifying Groups $R_3$

Charge modifying groups $R_3$ are groups used to effect charge modification of the modified polymer upon a change of condition of the polymer. For example charge modifying groups can be appended to reduce or enlarge the overall charge of the polymer upon a change of pH, or to change the charge of the modified polymer from one to another (i.e., change a negatively charged molecule to a positively charged molecule) upon transport across a membrane. The groups can also be used to introduce additional charge, or to neutralize charge already present. Charge modification can thus be used to form a polymer with a desired net charge or zeta potential as the polymer moves from one environment to another such as a transition from the extracellular space to the endosome/lysosome.

Charge modifiers can also be used to mask a particular functionality until the desired environment is reached.

The charge modifier can neutralize a charged group on a polymer or reverse the charge, from positive to negative or negative to positive, of a polymer ion. Charge modification of a polyion can reduce the charge of the polyion, form a polyion of opposite charge, or form a polyampholyte. Charge modification can also be used to form a polymer with a desired net charge density For example the charge modifying group can alter the charge of the polymeric species by forming a reversible, covalent bond between a moiety, such as an amine, on the polymer and one of the carbonyl groups of the compound as shown below:

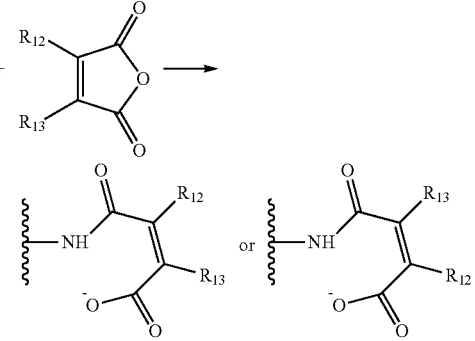

In this example, the polymeric species undergoes a change in charge from positive to negative as a consequence of the reaction of the amine functionality with the charge modifying agent to generate a neutral amide and a negatively charged carboxylate.

Examples of charge modifying group $R_3$, include but are not limited to, those of Formula (XVI):

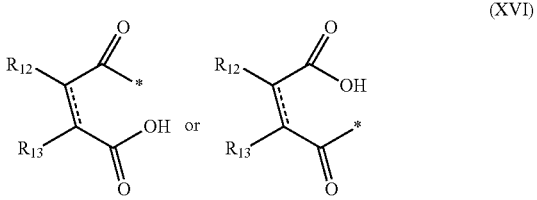

(XVI)

wherein:
$R_{12}$ is hydrogen, $C_{1-5}$ alkyl or $C_{6-10}$ aryl;
$R_{13}$ hydrogen, $C_{1-10}$ alkyl, $C_{6-10}$ aryl, —$(CH_2)_g$—$CO_2R_{14}$, —$(CH_2)_g$—$C(O)SR_{14}$, —$(CH_2)_q C(O)S(CH_2)_g CO_2R_{14}$ or —$(CH_2)_q CONHR_{15}$;
$R_{14}$ is hydrogen or $C_{1-5}$ alkyl;

$R_{15}$ is hydrogen, $C_{1-5}$ alkyl, $C_{6-10}$ aryl, aralkyl, alkyldithioaryl, aryldithioalkyl, alkyldithioalkyl, aryldithioaryl, —$(CH_2)_g$CHO or $R_j$;

g is an integer between 1 and 5 inclusive;

q is an integer between 0 and 5 inclusive; and

╌╌ is a single or a double bond.

In some embodiments, the charge modifying group of Formula (XVI) is

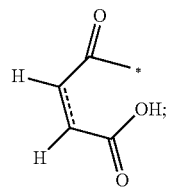
(1)

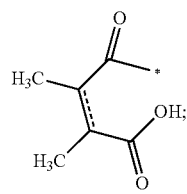
(2)

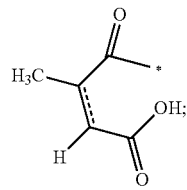
(3)

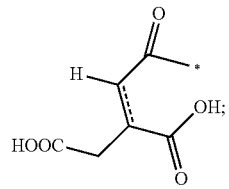
(4)

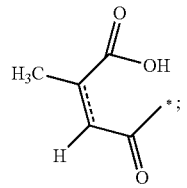
(5)

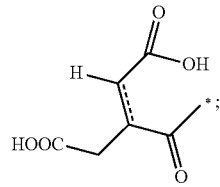
(6)

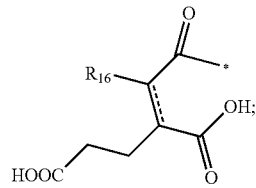
(7)

-continued

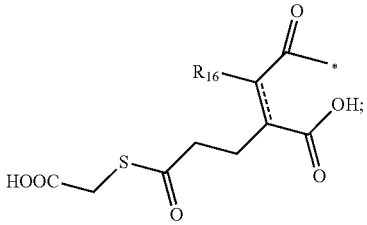
(8)

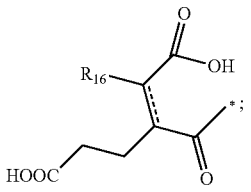
(9)

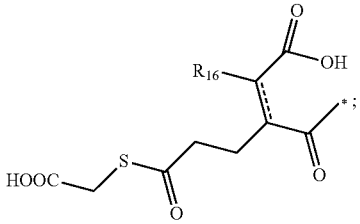
(10)

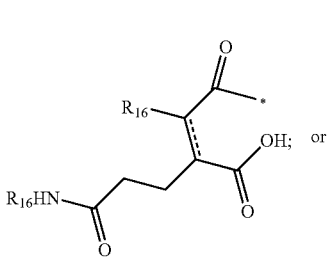
(11) or

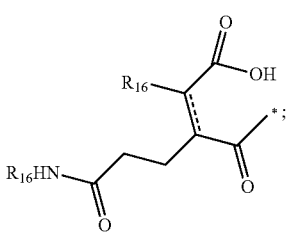
(12)

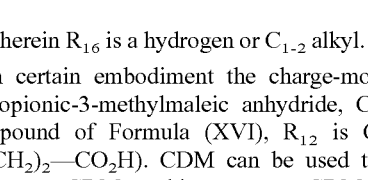

wherein $R_{16}$ is a hydrogen or $C_{1-2}$ alkyl.

In certain embodiment the charge-modifying agent is 2-propionic-3-methylmaleic anhydride, CDM (i.e. in the compound of Formula (XVI), $R_{12}$ is $CH_3$ and $R_{13}$ is —$(CH_2)_2$—$CO_2H$). CDM can be used to form a CDM-thioester, CDM-masking agent, CDM-steric stabilizer, CDM-ligand, CDM-PEG, or CDM-galactose, for example. Thus, a charge-modifying agent can be employed to alter the charge of the polymeric species while also serving as a linking moiety through which another moiety, such as a targeting moiety or a hydrophobic moiety can be linked to the polymer. For example, a charge-modifying group which incorporates a PEG moiety can be used to alter the charge of the polymeric species and also reversibly incorporate a PEG moiety:

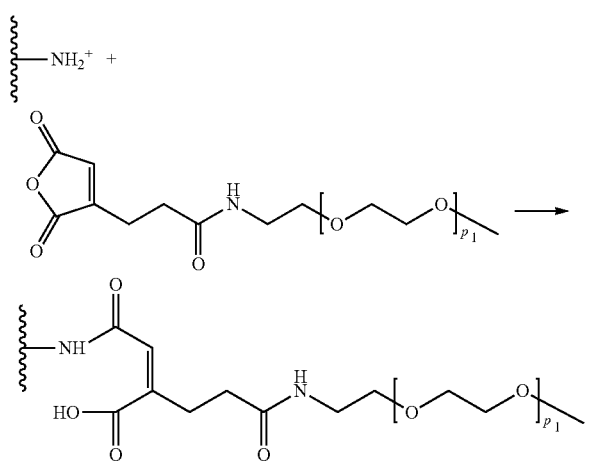

wherein $p_1$ is an integer between about 1 and about 1000 inclusive.

In a specific embodiment, the charge modifying group $R_3$ has the formula:

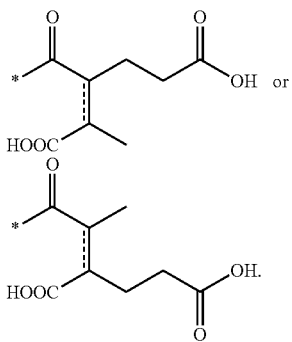

In embodiments, more than one type of charged modifying group $R_3$ can be used in one modified polymer. In this embodiment each type of charged modifying group $R_3$ is individually attached to the polymer backbone via a linker group $L_3$ of the same or different composition. The type and amount of each of the charge modifying groups is selected so as to provide the desired functionality to the polymer, which will depend on the type and purpose of the group and the charge being modified. In embodiments when the polymer contains more than one charged group per monomer, the charge modifying group will be statistically distributed along the polymer chain.

In one embodiment, the charged modifying group $R_3$ is attached to a N atom of $Z_3$, $Z_8$, or $R_2$.

In one embodiment, $n_3$ can be 0, i.e. no charge modifying group is linked to the polymer backbone via the —$W_3$—C(O)—$Z_3$— linker.

In embodiments where $Z_9$ is $Z_6$-$T_1$, $n_3$ is between about 0.02 and about 0.81 inclusive or between about 0.16 and about 0.49 inclusive.

In yet another embodiment, where $Z_9$ is $Z_8$ and each of $Z_8$ and $R_2$ is a polyamino moiety (e.g., a linear or branched polyethylenimine), $R_3$ can be linked to the polymer backbone via the —$W_3$—C(O)—$Z_3$— linker, $Z_8$ and/or $R_2$ and $m_3$ is 0.002-100. In this embodiment, each of $n_1$, $n_3$, $n_4$, and $n_5$ can be 0 or a non-zero value.

Hydrophobic Groups $R_4$

Hydrophobic groups $R_4$ are not water-soluble, and tend not to form hydrogen bonds. Hydrophobic groups can function to modify the HLB (hydrophilic-lipophilic balance) of the polymer. Certain hydrophobic groups interact with the cell membrane, thus improving uptake of the modified polymers and/or altering biodistribution of the modified polymer. Hydrophobic groups can be used to modify penetration and/or uptake of water by the modified polymer, thereby modifying the rate of release of the therapeutic agent from the modified polymer. Preferred hydrophobic groups have a non-negative octanol-water partition coefficient, more preferred hydrophobic groups have an octanol-water partition coefficient greater than 1, greater than 2, or more preferably greater than 3.

Hydrophobic groups include saturated, unsaturated, and aromatic hydrocarbons. In one embodiment, the hydrophobic group is an alkyl group having 3-30 carbons that can contain unsaturated carbons, optionally amide and ester groups, and can be branched. In one embodiment, the hydrocarbon groups are 3-30 carbons in length, can contain unsaturated carbons, amide groups, and esters, and can include branching.

Additional hydrophobic groups include lipids. Lipids which may be used include, but are not limited to, the following classes of lipids: fatty acids and derivatives, mono-, di and triglycerides, phospholipids, sphingolipids, cholesterol and steroid derivatives, terpenes and vitamins. Fatty acids and derivatives thereof may include, but are not limited to, saturated and unsaturated fatty acids, odd and even number fatty acids, cis and trans isomers, and fatty acid derivatives including alcohols, esters, anhydrides, hydroxy fatty acids and prostaglandins. Saturated and unsaturated fatty acids that may be used include, but are not limited to, molecules that have between about 12 carbon atoms and about 22 carbon atoms in either linear or branched form. Examples of saturated fatty acids that may be used include, but are not limited to, lauric, myristic, palmitic, and stearic acids. Examples of unsaturated fatty acids that may be used include, but are not limited to, lauric, physeteric, myristoleic, palmitoleic, petroselinic, and oleic acids. Examples of branched fatty acids that may be used include, but are not limited to, isolauric, isomyristic, isopalmitic, and isostearic acids and isoprenoids. Fatty acid derivatives include 12-(((T-diethylaminocoumarin-3 yl)carbonyl)methylamino)-octadecanoic acid; N-[12-(((7' diethylaminocoumarin-3-yl)carbonyl)methyl-amino)octade-canoyl]-2-aminopalmitic acid; N succinyl-dioleoylphosphatidylethanol amine and palmitoyl-homocysteine; and/or combinations thereof. Mono, di and triglycerides or derivatives thereof that may be used include, but are not limited to, molecules that have fatty acids or mixtures of fatty acids between 6 and 24 carbon atoms, digalactosyldiglyceride, 1,2-dioleoyl-glycerol; 1,2-cdipalmitoyl-3 succinylglycerol; and 1,3-dipalmitoyl-2-succinylglycerol.

Phospholipids which may be used include, but are not limited to, phosphatidic acids, phosphatidyl cholines with both saturated and unsaturated lipids, phosphatidyl ethanolamines, phosphatidylglycerols, phosphatidylserines, phosphatidylinositols, lysophosphatidyl derivatives, cardiolipin, and β-acyl-y-alkyl phospholipids. Examples of phospholipids include, but are not limited to, phosphatidylcholines such as dioleoylphosphatidylcholine, dimyristoylphosphatidylcholine, dipentadecanoylphosphatidylcholine dilauroylphosphatidylcholine, dipalmitoylphosphatidylcholine (DPPC), distearoylphosphatidylcholine (DSPC), diarachidoylphosphatidylcholine (DAPC), dibehenoylphosphatidylcholine (DBPC), ditricosanoylphosphatidylcholine (DTPC), dilignoceroylphatidylcholine (DLPC); and phosphatidylethanolamines such as dioleoylphosphatidylethanolamine or 1-hexadecyl-2-palmitoylglycerophosphoethanolamine. Synthetic phospholipids with asymmetric acyl chains (e.g., with one acyl chain of 6 carbons and another acyl chain of 12 carbons) may also be used.

Sphingolipids which may be used as hydrophobic groups include ceramides, sphingomyelins, cerebrosides, gangliosides, sulfatides and lysosulfatides. Examples of Sphinglolipids include, but are not limited to, the gangliosides GM1 and GM2.

Steroids which may be used as hydrophobic groups include, but are not limited to, cholesterol, cholesterol sulfate, cholesterol hemisuccinate, 6-(5-cholesterol 3β-yloxy)hexyl-6-amino-6-deoxy-1-thio-α-D-galactopyranoside, 6-(5-cholesten-3,3-yloxy)hexyl-6-amino-6-deoxyl-1-thio-α-D mannopyranoside and cholesteryl)4'-trimethyl 35 ammonio) butanoate.

Additional lipid compounds which may be used include tocopherol and derivatives, and oils and derivatized oils such as stearylamine.

A variety of cationic lipids such as DOTMA, N-[1-(2,3-dioleoyloxy)propyl-N,N,N-trimethylammonium chloride; DOTAP, 1,2-dioleoyloxy-3-(trimethylammonio)propane; and DOTB, 1,2-dioleoyl-3-(4'-trimethyl-ammonio)butanoyl-glycerol may be used.

Other hydrophobic groups include hydrophobic amino acids such as tryptophan, tyrosine, isoleucine, leucine, and valine, and aromatic groups such as an alkyl paraben, for example, methyl paraben, and benzoic acid.

Other types of hydrophobic groups include molecules that interact with membranes such as fatty acids, cholesterol, dansyl compounds, and amphotericin derivatives. In one embodiment, the hydrophobic group is a lipophilic group that includes groups comprising lipids, cholesterol, cholic acid, adamantane acetic acid, 1-pyrene butyric acid, dihydrotestosterone, 1,3-bis-O(hexadecyl)glycerol, borneol, menthol, 1,3-propanediol, hexadecylglycerol, palmitic acid, myristic acid, O3-(oleoyl)lithocholic acid, O3-(oleoyl)cholenic acid, and phenoxazine; and groups such as dimethoxytrityl groups, oleyl, retinyl, and steroids, such as cholesteryl, geranyloxyhexyl groups, and heptadecyl groups.

In another embodiment, each hydrophobic group $R_4$ is independently a $C_4$-$C_{18}$alkanoyl, a hydrophobic amino acid selected from tryptophan, isoleucine, and valine, an alkyl paraben, and a phospholipid.

In one embodiment each hydrophobic group $R_4$ is attached to the polymer backbone via a linker group $L_4$. In another embodiment more than one type of hydrophobic group $R_4$ is used in one modified polymer.

In one embodiment the hydrophobic group $R_4$ comprises $C_{5-20}$ saturated or unsaturated fatty acids, such as, hexanoic acid, heptanoic acid, 6-methylhetanoic acid palmitic acid, myristic acid and oleic acid; $C_{6-22}$ alkylamines such as octylamine, decylamine, dodecylamine, octadecylamine; cholesterol, cholesterol derivatives such as cholic acid; or amino containing lipids, such as, phosphatidylethanolamine and phosphatidylserine.

In one embodiment, each of $R_4$, independently, is:

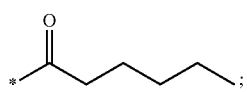

(1)

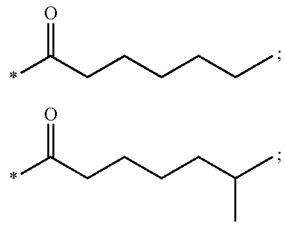

(2)

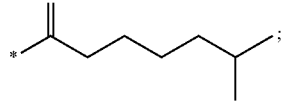

(3)

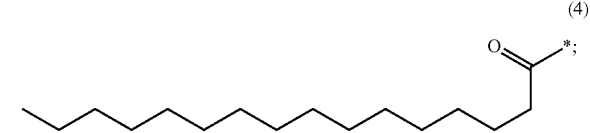

(4)

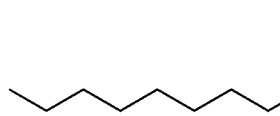

(5)

*—NH(CH$_2$)$_{17}$CH$_3$;

(6)

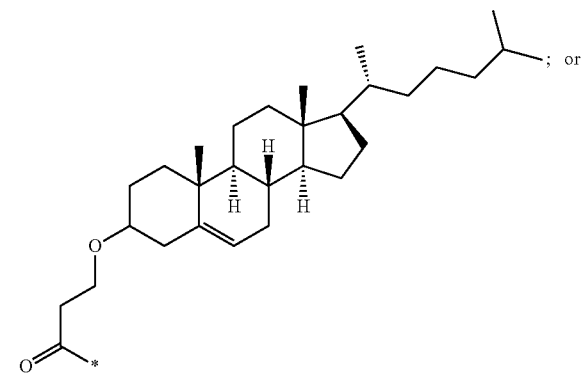

(7); or

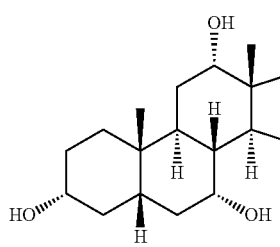

(8)

In one embodiment, more than one type of hydrophobic group $R_4$ can be used in one modified polymer. In this embodiment, each type of hydrophobic group $R_4$ is individually attached to the polymer backbone via a linker group $L_4$ of the same or different composition. The type and amount of each of the hydrophobic groups in the modified polymer is selected so as to provide the desired properties and functionality to the polymer, which will depend on the type and purpose of the group.

In one embodiment, $n_4$ can be 0, i.e. no hydrophobic group is linked to the polymer backbone via the —W$_4$—C(O)—Z$_4$— linker.

In embodiments where $Z_9$ is $Z_6$-$T_1$, $n_4$ is between about 0.03 and about 0.30 inclusive; or between about 0.05 and about 0.15 inclusive.

In yet another embodiment, where $Z_9$ is $Z_8$ and each of $Z_8$ and $R_2$ is a polyamino moiety (e.g., a linear or branched polyethylenimine), $R_4$ can be linked to the polymer backbone via the —$W_4$—C(O)—$Z_4$— linker, $Z_8$ and/or $R_2$ and $m_4$ is 0.03-0.30 or 0.05-0.15. In this embodiment, each of $n_1$, $n_3$, $n_4$, and $n_5$ can be 0 or a non-zero value.

In one embodiment, the hydrophobic group $R_4$ is attached to a N atom of $Z_4$, $Z_8$, or $R_2$.

Protective Groups $R_5$

In one embodiment, each $R_5$ is independently the same or different. In this embodiment each type of group $R_5$ is individually attached to the polymer backbone via a linker group $L_5$ of the same or different composition. The type and amount of each $R_5$ group in the modified polymer is selected so as to provide the desired properties and functionality to the polymer, which will depend on the type and purpose of the group.

In one embodiment, $n_5$ can be 0, i.e. no protective group is linked to the polymer backbone via the —$W_5$—C(O)—$Z_5$— linker.

In embodiments where $Z_9$ is $Z_6$-$T_1$, $n_5$ is between about 0.01 and about 0.03 inclusive or $n_5$ is about 0.02.

In yet another embodiment, where $Z_9$ is $Z_8$ and each of $Z_8$ and $R_2$ is a polyamino moiety (e.g., a linear or branched polyethylenimine), $R_5$ can be linked to the polymer backbone via the —$W_5$—C(O)—$Z_5$— linker, $Z_8$ and/or $R_2$ and $m_5$ is 0.01 and about 0.03 inclusive or $n_5$ is about 0.02. In this embodiment, each of $n_1$, $n_3$, $n_4$, and $n_5$ can be 0 or a non-zero value.

In one embodiment, the protective group $R_5$ is attached to a N atom of $Z_5$, $Z_8$, or $R_2$.

Polynucleotides $R_6$

A wide variety of polynucleotides can be appended to the polymer backbone as $R_6$. The function of the polynucleotide is not particularly limited, and can be, for example, a therapeutic agent, a biomarker, an assaying agent, or a diagnostic agent. In other embodiments, a polynucleotide is delivered to a cell to express an exogenous nucleotide sequence, to inhibit, eliminate, augment, or alter expression of an endogenous nucleotide sequence, or to affect a specific physiological characteristic not naturally associated with the cell.

In another embodiment, polynucleotides are natural, synthetic, or semi-synthetic. Natural polynucleotides have a ribose-phosphate backbone. An artificial or synthetic polynucleotide is a polynucleotide that is polymerized in vitro or in a cell free system such as by chemical synthesis and contains the same or similar bases but can contain a backbone of a type other than the natural ribose-phosphate backbone. These backbones include, for example, PNAs (peptide nucleic acids), phosphorothioates, phosphorodithioates, phosphorodiamidates, morpholinos, and other variants of the phosphate backbone of native polynucleotides. Bases include purines and pyrimidines, which further include the natural compounds adenine, thymine, guanine, cytosine, uracil, inosine, and natural analogs. Synthetic derivatives of purines and pyrimidines include, but are not limited to, modifications that place new reactive groups such as, but not limited to, amines, alcohols, thiols, carboxylates, and alkylhalides. The term base encompasses any of the known base analogs of DNA and RNA including, but not limited to, 4-acetylcytosine, 8-hydroxy-N-6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudo-uracil, 1-methylguanine, 1-methylinosine, 2,2-dimethyl-guanine, 2-methyladenine, 2-methylguanine, 3-methyl-cytosine, 5-methylcytosine, N6-methyladenine, 7-methylguanine, 5-methylaminomethyluracil, 5-methoxy-amino-methyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine. The term polynucleotide includes deoxyribonucleic acid (DNA) and ribonucleic acid (RNA).

The polynucleotide can be DNA or RNA. DNA can be in form of cDNA, in vitro polymerized DNA, plasmid DNA, parts of a plasmid DNA, genetic material derived from a virus, linear DNA, vectors (P1, PAC, BAC, YAC, artificial chromosomes), expression cassettes, chimeric sequences, recombinant DNA, chromosomal DNA, an oligonucleotide, anti-sense DNA, nicked DNA or derivatives of these groups. RNA can be in the form of mRNA (messenger RNA), in vitro polymerized RNA, recombinant RNA, oligonucleotide RNA, tRNA (transfer RNA), snRNA (small nuclear RNA), rRNA (ribosomal RNA), chimeric sequences, anti-sense RNA, interfering RNA, siRNA (small interfering RNA), dicer substrate siRNA, miRNA (microRNA), external guide sequences, smRNA (small non-messenger RNAs), utRNA (untranslatedRNA), snoRNAs (24-mers, modified smRNA that act by an anti-sense mechanism), tiny non-coding RNAs (tncRNAs), small hairpin RNA (shRNA), locked nucleic acid (LNA), unlocked nucleic acid (UNA) and other RNA function inhibitors and activators, ribozymes, and the like, and derivatives of these groups. In one embodiment, the polynucleotide is an anti-sense polynucleotide that is a polynucleotide that interferes with the function of DNA and/or RNA. The polynucleotide can also be a sequence whose presence or expression in a cell alters the expression or function of cellular genes or RNA. In addition, DNA and RNA can be single, double, triple, or quadruple stranded.

In one embodiment, the polynucleotide contains an expression cassette coded to express a whole or partial protein, or RNA (including shRNA). An expression cassette refers to a natural polynucleotide or polynucleotide produced by recombinant that is capable of expressing one or more RNA transcripts. The term recombinant as used herein refers to a polynucleotide that is comprised of segments of polynucleotide joined together by means of molecular biological techniques. The cassette contains the coding region of the gene of interest along with any other sequences that affect expression of the gene. A DNA expression cassette typically includes a promoter (allowing transcription initiation), and a sequence encoding one or more proteins. Optionally, the expression cassette can include, but is not limited to, transcriptional enhancers, non-coding sequences, splicing signals, transcription termination signals, and polyadenylation signals. An RNA expression cassette typically includes a translation initiation codon (allowing translation initiation), and a sequence encoding one or more proteins. Optionally, the expression cassette can include, but is not limited to, translation termination signals, a polyadenosine sequence, internal ribosome entry sites (IRES), and non-coding sequences, as well as sh, siRNA, or micro RNAs.

In another embodiment, at least a portion of the polynucleotide is self-complementary, that is, at least a portion of the nucleotides in both strands are involved in nucleotide pairs, or they can form single-stranded regions, such as one or more of overhangs, bulges, loops, etc. Overhangs, if present, they are specifically of a length of 1 to 4, and more specifically 2 or 3 nucleotides in length. In one embodiment, the length of the overhang(s) does not exceed 100, or 50, or 20, or 10, or 5 nucleotides. They can be located at the 3'- or the 5'-end of either strand, but specific embodiments comprise at least one overhang on the 3'-ends of the antisense strand, or of both strands.

In the embodiment wherein at least a portion of the polynucleotide is self-complementary, the two strands forming the duplex structure can be different portions of one larger RNA molecule, or they can be separate RNA molecules. Wherein the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop". Wherein the two strands are connected covalently by means other than an uninterrupted chain of nucleotides between the 3'-end of one strand and the 5'-end of the respective other strand forming the duplex structure, the connecting structure is referred to as a strand linkage. Wherein the two strands are connected by a hairpin loop, and the duplex structure consists of not more than 30 nucleotide pairs, the RNAi agent can be referred to herein as a short hairpin RNA (shRNA). Wherein the two strands are not connected, or connected by a strand linkage, and the duplex structure consists of not more than 30 nucleotide pairs, the RNAi agent can be referred to herein as a short interfering RNA (siRNA).

As used herein, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, wherein stringent conditions include: 400 mM NaCl, 40 mM PIPES pH 6.4, 1 mM EDTA, 50° C. or 70° C. for 12-16 hours followed by washing. "Complementary" sequences can be fully complementary, or they can include mismatches, as long as they are still able to hybridize under the chosen conditions. In one embodiment, complementary sequences include not more than 1, not more than 2, not more than 3, not more than 4, or not more than 5 mismatches, if any. The degree of complementarity will be such that stable and specific binding occurs between the two oligonucleotides comprising the sequences referred to as complementary. Specific binding requires a sufficient lack of complementarity to non-target sequences under conditions in which specific binding is desired, i.e., under physiological conditions in the case of in vivo assays or therapeutic treatment, or in the case of in vitro assays, under conditions in which the assays are performed. It has been shown that a single mismatch between targeted and non-targeted sequences can be sufficient to provide discrimination for siRNA targeting of an mRNA.

In one embodiment, the polynucleotide is an RNA function inhibitor. An RNA function inhibitor ("inhibitor") comprises a polynucleotide or polynucleotide analog containing a sequence ("inhibiting sequence") whose presence or expression in a cell alters the stability or trafficking of, or inhibits the function or translation of a specific cellular RNA, usually an mRNA, in a sequence-specific manner. In the case of mRNA, inhibition of RNA can thus effectively inhibit expression of a gene from which the RNA is transcribed. "Inhibit" or "down regulate" means that the activity of a gene expression product or level of RNAs or equivalent RNAs is reduced below that observed in the absence of the polynucleotide. In one embodiment, inhibition with a polynucleotide is below that level observed in the presence of an inactive or attenuated molecule that is unable to mediate a response. In another embodiment, inhibition of gene expression with the polynucleotide is greater in the presence of the polynucleotide than in its absence.

Exemplary RNA function inhibitors include siRNA, interfering RNA or RNAi, shRNA, dsRNA, RNA polymerase transcribed DNAs, ribozymes, and antisense polynucleotide, which can be RNA, DNA, or artificial polynucleotide. In one embodiment, siRNA comprises a double stranded structure typically containing 15 to 50 base pairs and preferably 21 to 25 base pairs and having a nucleotide sequence identical or nearly identical to an expressed target gene or RNA within the cell. siRNA also includes modified siRNAs such as 27-nucleotide dicer substrates, meroduplex siRNAs (siRNAs with a nick or gap in the sense strand), and usiRNAs (siRNAs modified with non-nucleotide acyclic monomers known as unlocked nucleobase analogs), and other modified siRNAs. Antisense polynucleotides include, but are not limited to: morpholinos, 2'-O-methyl or 2'F polynucleotides, DNA, RNA, locked nucleic acids, and the like. RNA polymerase transcribed DNAs can be transcribed to produce small hairpin RNAs in the cell that can function as siRNA or linear RNAs that can function as antisense RNA. The inhibitor can be polymerized in vitro, can be delivered as a recombinant construct to produce the RNA in a cell, contain chimeric sequences, or derivatives of these groups. The inhibitor can contain ribonucleotides, deoxyribonucleotides, synthetic nucleotides, or any suitable combination such that the target RNA and/or gene is inhibited. In addition, these forms of polynucleotide can be single, double, triple, or quadruple stranded.

In one embodiment, the polynucleotide is a siRNA, a short polynucleotide molecule that can be unmodified or modified chemically. In other embodiments the siRNA is a 15 to 30 mer, specifically 15, 16, 17, 18, 19, 20, 21, 22, 23, 24, 25, 26, 27, 28, 29 or 30-mer siRNA. The efficiency of siRNA can be determined by the ability to reduce the quantity of the target transcript or protein so that the functional properties associated with that transcript or protein is impaired. The siRNA can be synthesized either chemically or enzymatically or expressed from a vector. In other embodiments, there are provided chemically synthesized siRNAs which can be used to reduce expression levels of micro or other intracellular RNA species.

In one embodiment, an RNAi agent's antisense strand is "sufficiently complementary" to a target RNA, such that the RNAi agent inhibits production of protein encoded by the target mRNA. The target RNA can be, e.g., a pre-mRNA or mRNA endogenous to a subject or organism. In another embodiment, the RNAi agent is "fully complementary" to a target RNA, e.g., the target RNA and the RNAi agent anneals to form a hybrid made exclusively of Watson-Crick base pairs in the region of exact complementarity. A "sufficiently complementary" RNAi agent antisense strand can include a region (e.g., of at least 7 nucleotides) that is exactly complementary to the target RNA. Moreover, in some embodiments, the RNAi agent specifically discriminates a single-nucleotide difference. In this case, the RNAi agent only down-regulates gene expression from an mRNA if exact complementarity is found in the region of the single-nucleotide difference.

While some embodiments focus on siRNA, the disclosure is not to be construed as limited to siRNA, but also encompasses related compositions and methods practiced with short polynucleotides, double stranded RNA (dsRNA), meroduplex siRNAs, usiRNAs, microRNA (mRNA), deoxyribose polynucleotide interference (DNAi) and short hairpin RNA (shRNA), enzymatic polynucleotide molecules or antisense polynucleotide molecules.

In any of the embodiments herein, $n_6$ or $m_6$ can be between about 0.0004 and about 0.10 inclusive, between about 0.0004 and about 0.077 inclusive or between about 0.0006 and about 0.002 inclusive.

In one embodiment the polynucleotide is a double stranded oligonucleotide having between about 12 and about 30 nucleotides. In another embodiment the polynucleotide is a single stranded oligonucleotide having between about 8 and about 64 nucleotides.

In one embodiment more than one type of polynucleotide can be appended to one modified polymer. In this embodiment each type of polynucleotide $R_6$ is individually attached to the polymer backbone via a linker group $L_6$ of the same or different composition.

In one embodiment the polynucleotide is siRNA. In another embodiment the siRNA is linked to the modified polymer via a linker group $L_6$ through the 3' end of the anti-sense strand of the siRNA.

Evaluation of Candidate Modified Polymers

A candidate modified polymer is evaluated for a selected property by exposing the candidate agent and a control molecule to the appropriate conditions and evaluating for the presence of the selected property. For example, resistance to a degradant can be evaluated as follows. A candidate modified polymer is exposed to degradative conditions, e.g., exposed to a milieu that includes a degradative agent such as a nuclease, a biological sample that is similar to a milieu that might be encountered in therapeutic use such as blood or serum, or a cellular fraction, such as a cell-free homogenate or disrupted cells. The candidate and control is then evaluated for resistance to degradation by any of a number of approaches. For example, the candidate and control could be labeled, preferably prior to exposure, with, for example, a radioactive, enzymatic, or a fluorescent label, such as Cy3 or Cy5. Control and candidate RNAs can be incubated with the degradative agent, and optionally a control, that is, an inactivated such as a heat inactivated, degradative agent. A physical parameter, e.g., size, of the test and control molecules is then determined. Determination can be by a physical method, for example, by polyacrylamide gel electrophoresis, sizing column, or analytical HPLC/mass spectrometry to assess whether the molecule has maintained its original length, or assessed functionally. Alternatively, Northern blot analysis or can be used to assay the length of an unlabeled molecule. qRT-PCR may also be used to determine the amount of intact RNA.

A functional assay can also be used to evaluate the candidate modified polymer. A functional assay can be applied initially or after an earlier non-functional assay, (e.g., assay for resistance to degradation) to determine if the modified polyacetal construct alters the ability of the molecule to inhibit gene expression. For example, a cell, such as a mouse or human cell, can be co-transfected with a plasmid expressing a reporter gene, the levels of which can be easily and quantitatively assessed. Such reporters can be enzymes, or in some embodiments, a fluorescent protein, such as GFP. In each case, a candidate polymer conjugated with an RNAi homologous to the transcript encoding the reporter transcript (see, e.g., WO 00/44914, incorporated herein by reference) is exposed to a cell expressing the reporter, and levels of the reporter quantitated as a function of time and/or concentration of the polymer-RNAi conjugate. For example, a candidate RNAi modified polymer homologous to the GFP mRNA can be assayed for the ability to inhibit GFP expression by monitoring for a decrease in cell fluorescence, as compared to a control cell, in which the transfection did not include the candidate RNAi modified polymer, e.g., controls with no modified polymer added and/or controls. Efficacy of the candidate modified polymer on gene expression can be assessed by comparing cell fluorescence in the presence of the modified and unmodified RNAi. In addition, GFP or any other suitable reporter transcript may be expressed as a fusion to a heterologous RNA sequence containing one or more regions homologous to an RNAi that is being tested as a polymer conjugate.

In an alternative functional assay, cells can be exposed to a candidate RNAi modified polymer homologous to an endogenous gene to assess the ability of the modified polymer to inhibit gene expression either in vitro or in vivo A phenotype can be monitored as an indicator that the modified polymer is inhibiting expression. Alternatively, the effect of the candidate modified polymer on target RNA levels can be verified by Northern blot, qRT-PCR, or bDNA assay to detect a decrease in the level of target RNA, or by Western blot or ELISA assay to assay for a decrease in the level of target protein, as compared to a negative control. Controls can include cells in which no modified polymer is added, cells (or an in vivo organism) in which a non-polyacetal RNA is added, in which an irrelevant RNA conjugated to a polyacetal was evaluated.

An RNAi modified polymer that targets a miRNA or pre-miRNA can be assayed either by directly measuring levels of the miRNA to which it binds (by qRT-PCR or Northern blot), or by monitoring expression of the transcript targeted. For example, an RNAi modified polymer designed to bind a miRNA that targets an endogenous enzyme can be assessed by monitoring for an increase mRNA transcript level or its encoded protein product, as compared to a control cell.

In each case, the RNAi modified polymer can be evaluated with respect to its ability to regulate gene expression. Levels of gene expression in vivo can be measured, for example, by in situ hybridization, or by the isolation of RNA from tissue prior to and following exposure to the RNAi modified polymer. Wherein the animal needs to be sacrificed in order to harvest the tissue, an untreated control animal will serve for comparison. Target mRNA can be detected by methods including but not limited to RT-PCR, Northern blot, branched-DNA assay, or RNAase protection assay. Moreover, the cleavage product generated by the action of the RNAi on the targeted RNA can be detected in a semi-quantitative fashion using the 5'-RACE assay. Alternatively, or additionally, gene expression can be monitored by performing Western blot analysis on tissue extracts treated with the RNAi modified polymer.

In a bDNA assay, branched DNA is mixed with a sample to be tested. The detection is encompassed by a non-radioactive method and does not require a reverse transcription step of the RNA polynucleotide to be detected. The assay entirely relies on hybridization as principle. Enzymes are used to indicate the extent of hybridization but are not used to manipulate the polynucleotides. Thus, small amounts of a polynucleotide can be detected and quantified without a reverse transcription step (in the case of RNA) and/or PCR. This assay allows evaluation of the effects on gene expression in multiple samples in parallel, making it suitable both for screening (i.e. evaluation of gene expression in multiple samples exposed to an RNAi modified polymer in vitro), as well as evaluation of gene expression in various organs or tissues from multiple animals to which and RNAi modified polymer has been administered.

Several different short single-stranded DNA molecules (oligonucleotides) are used in a branched DNA-assay. The capture and capture-extender oligonucleotides bind specifically to the target RNA and immobilize it on a solid support. The immobilization of the target on a solid support makes extensive washing easier, which reduces false positive results. The label oligonucleotide binds to the immobilized target polynucleotide and the branched DNA anneals to the label oligonucleotide. The branched DNA is coupled to an enzyme (e.g., alkaline phosphatase). The branching of the DNA allows for very dense decorating of the target-label complex with the enzyme which is important for the high sensitivity of the assay. In the case of alkaline phosphatase, the enzyme catalyzes a reaction of a substrate which generates light (detectable in a luminometer). The amount of light emitted is proportional with the amount of the specific RNA polynucleotide present in the sample.

In a typical bDNA assay, cells are lysed to release RNA. Probe Set oligonucleotides are designed to determine the specificity of the target RNA capture. Typical probe set oligonucleotides (capture extender (CE), label extender (LE), and blocking probe (BL)) bind a contiguous region of the target RNA and the CEs (capture extenders), by cooperative hybridization, selectively capture target RNA to the 96-well Capture Plate during an overnight incubation. Signal amplification is performed via sequential hybridization of ligation extenders. The number of LEs determines assay sensitivity. Addition of a chemilumigenic substrate generates a luminescent signal that is proportional to the amount of target mRNA present in the sample.

Levels of RNA can also be assessed using quantitative PCR.

Pharmaceutical Compositions

Also included are pharmaceutical compositions comprising one or more modified polymers as disclosed herein in an acceptable carrier, such as a stabilizer, buffer, and the like. The modified polymers can be administered and introduced into a subject by standard means, with or without stabilizers, buffers, and the like, to form a pharmaceutical composition. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal, oral or parenteral administration including intravenous, intraarterial, subcutaneous, intraperitoneal or intramuscular injection or infusion or intracranial, e.g., intrathecal or intraventricular, administration. The modified polymers can be formulated and used as sterile solutions and/or suspensions for injectable administration; lyophilized powders for reconstitution prior to injection/infusion; topical compositions; as tablets, capsules, or elixirs for oral administration; or suppositories for rectal administration, and the other compositions known in the art.

A pharmacological composition or formulation refers to a composition or formulation in a form suitable for administration, e.g., systemic administration, into a cell or subject, including for example a human. Suitable forms, in part, depend upon the use or the route of entry, for example oral, inhaled, transdermal, or by injection/infusion. Such forms should not prevent the composition or formulation from reaching a target cell (i.e., a cell to which the negatively charged polynucleotide is desirable for delivery). For example, pharmacological compositions injected into the blood stream should be soluble. Other factors are known in the art, and include considerations such as toxicity and forms that prevent the composition or formulation from exerting its effect.

By "systemic administration" is meant in vivo systemic absorption or accumulation of the modified polymer in the blood stream followed by distribution throughout the entire body. Administration routes that lead to systemic absorption include, without limitation: intravenous, subcutaneous, intraperitoneal, inhalation, oral, intrapulmonary, and intramuscular. Each of these administration routes exposes the modified polymers to an accessible diseased tissue. The rate of entry of an active agent into the circulation has been shown to be a function of molecular weight or size. The use of a modified polymer can potentially localize the polynucleotide in certain tissue types, such as the tissues of the reticular endothelial system (RES). This approach can provide enhanced delivery of the polynucleotide to target cells by taking advantage of the specificity of macrophage and lymphocyte immune recognition of abnormal cells, such as cancer cells.

A "pharmaceutically acceptable formulation" means a composition or formulation that allows for the effective distribution of the modified polymers in the physical location most suitable for their desired activity. In one embodiment, effective delivery occurs before clearance by the reticuloendothelial system or the production of off-target binding which can result in reduced efficacy or toxicity. Non-limiting examples of agents suitable for formulation with the modified polymers include: P-glycoprotein inhibitors (such as Pluronic P85), which can enhance entry of active agents into the CNS; biodegradable polymers, such as poly (DL-lactide-coglycolide) microspheres for sustained release delivery after intracerebral implantation; and loaded nanoparticles, such as those made of polybutylcyanoacrylate, which can deliver active agents across the blood brain barrier and can alter neuronal uptake mechanisms.

Also included herein are pharmaceutical compositions prepared for storage or administration, which include a pharmaceutically effective amount of the desired modified polymers in a pharmaceutically acceptable carrier or diluent. Acceptable carriers or diluents for therapeutic use are well known in the pharmaceutical art. For example, buffers, preservatives, bulking agents, dispersants, stabilizers, dyes, can be provided. In addition, antioxidants and suspending agents can be used.

The term "pharmaceutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Pharmaceutically effective amounts for a given situation can be determined by routine experimentation that is within the skill and judgment of the clinician. In a preferred aspect, the disease or condition to can be treated via gene silencing.

For any modified polymer, the pharmaceutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

In one embodiment, the modified polymers are formulated for parenteral administration by injection including using conventional catheterization techniques or infusion. Formulations for injection may be presented in unit dosage form, e.g., in ampules or in multi-dose containers, with an added preservative. The modified polymers can be administered parenterally in a sterile medium. The modified polymer, depending on the vehicle and concentration used, can either be suspended or dissolved in the vehicle. Advantageously, adjuvants such as local anesthetics, preservatives, and buffering agents can be dissolved in the vehicle. The term "parenteral" as used herein includes percutaneous, subcutaneous, intravascular (e.g., intravenous), intramuscular, or intrathecal injection or infusion techniques and the like. In addition, there is provided a pharmaceutical formulation comprising modified polymers and a pharmaceutically acceptable carrier. One or more of the modified polymers can be present in association with one or more non-toxic pharmaceutically acceptable carriers and/or diluents and/or adjuvants, and if desired other active ingredients.

The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose, a bland fixed oil can be employed including synthetic mono- or diglycerides. In addition, fatty acids such as oleic acid find use in the preparation of injectables.

Dosage levels of the order of from between about 0.01 mg and about 140 mg per kilogram of body weight per day are useful in the treatment of the above-indicated conditions (between about 0.05 mg and about 7 g per subject per day). The amount of modified polymer that can be combined with the carrier materials to produce a single dosage form varies depending upon the host treated and the particular mode of administration. Dosage unit forms can generally contain from between about 0.01 mg and about 100 mg inclusive; between about 0.01 mg and about 75 mg inclusive; or between about 0.01 mg and about 50 mg inclusive of a modified polymer.

It is understood that the specific dose level for a particular subject depends upon a variety of factors including the activity of the specific modified polymer used, the age, body weight, general health, sex, diet, time of administration, route of administration, and rate of excretion, combination with other active agents, and the severity of the particular disease undergoing therapy.

For administration to non-human animals, the modified polymer can also be added to the animal feed or drinking water. It can be convenient to formulate the animal feed and drinking water so that the animal takes in a therapeutically appropriate quantity of the modified polymers along with its diet. It can also be convenient to present the modified polymers as a premix for addition to the feed or drinking water.

The modified polymers can also be administered to a subject in combination with other therapeutic compounds to increase the overall therapeutic effect. The use of multiple compounds to treat an indication can increase the beneficial effects while reducing the presence of side effects.

Synthesis of Modified Polymers

Abbreviations

The following abbreviations are used in the reaction schemes and synthetic examples, which follow. This list is not meant to be an all-inclusive list of abbreviations used in the application as additional standard abbreviations, which are readily understood by those skilled in the art of organic synthesis, can also be used in the synthetic schemes and examples.

BSA bovine serum albumin
CDM carboxy dimethylmaleic acid
DMF dimethylformamide
EDA ethylenediamine
GA glutaric anhydride
GUA N-(4-aminobutyl)guanidine
HA-NHS hexanoic acid N-hydroxysuccinimide ester (N-hydroxysuccinimidyl hexanoate)
IMA 1-(3-Aminopropyl)imidazole
IMPA isopropyl methylphosphonic acid
NAG N-acetyl glucosamine
NHS N-hydroxysucinimidyl
PBS phosphate buffered saline
PEI polyethylenimine
PHF poly(1-hydroxymethylethylene hydroxylmethylformal), or FLEXIMER®
RP-HPLC reverse-phase high performance liquid chromatography
SPDP N-Succinimidyl 3-(2-pyridyldisulfanyl)-propionate
-SS- Indicates a covalently bound disulfide group
SSP 2-pyridyldisulfanyl
SSPy 3-(2-pyridyldisulfanyl)-propionate Scheme 1 shows the synthesis of a PHF polymer directly linked to an amino/polyamino moiety via a carbamate linker.

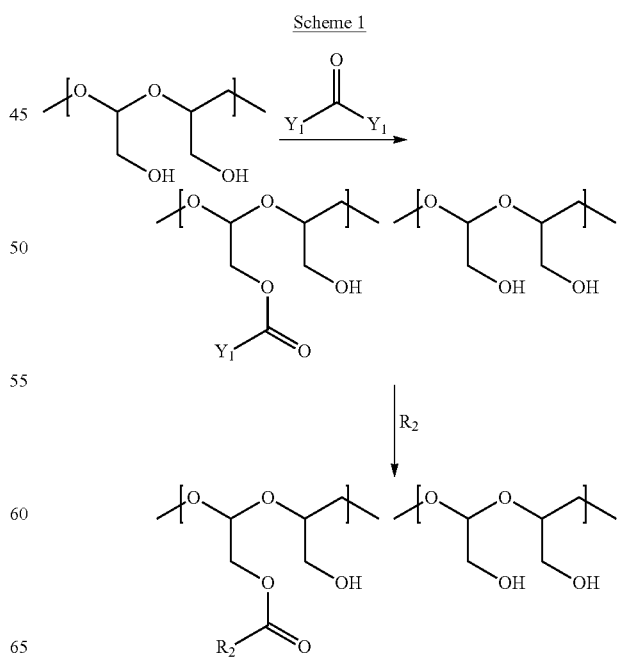

Scheme 1 wherein:

Y$_1$, independently, is:

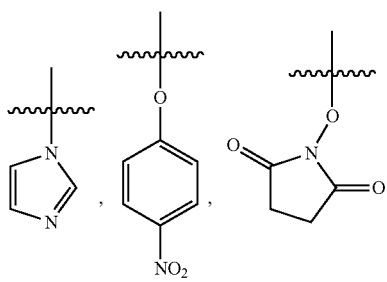

or a halogen; and

R$_2$ is as defined herein.

R$_2$ can be a single amino/polyamino moiety or a mixture of amino/polyamino moieties.

The synthesis is conducted without isolation of the product of the first reaction. The final product is purified by ultrafiltration or precipitation.

Scheme 2 shows the synthesis of a PHF polymer indirectly linked to an amino/polyamino moiety via a dicarboxylic acid compound in which one carboxylic group is linked to the nitrogen atom of the amino/polyamino moiety via an amide bond and the other carboxylic group is linked to the hydroxyl group of the acetal unit via an ester bond

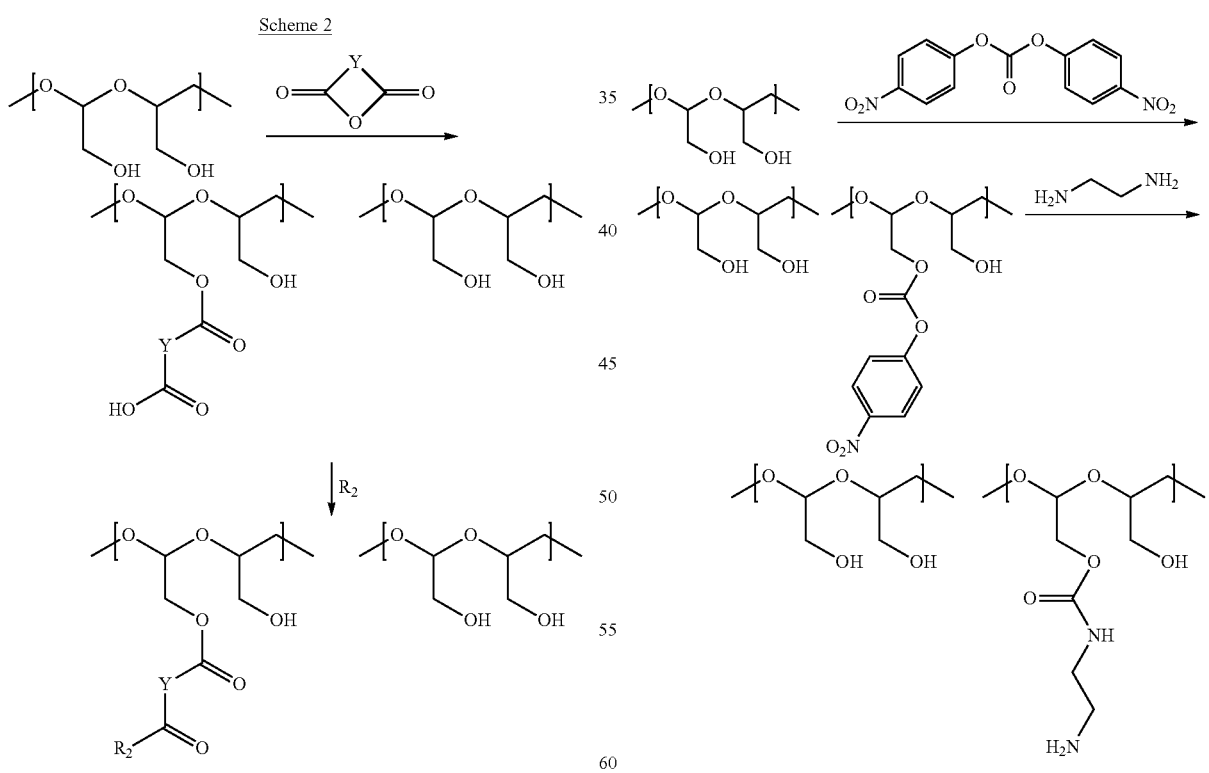

wherein:

Y, and R$_2$ are as defined herein

R$_2$ can be a single amino/polyamino moeity or a mixture of amino/polyamino moieties.

The polyacetal polymer is reacted with a cyclic anhydride such as, succinic anhydride, glutaric anhydride to form the intermediate polymer which is not isolated. The final product is purified by ultrafiltration, precipitation or dialysis.

EXAMPLES

Modified polymers described herein can be prepared by the method generally outlined below. Diafiltration was conducted using a Millipore Pelican tangential flow system equipped with 10,000 Da molecular weight cut-off membranes unless noted otherwise.

ApoB100 mRNA (mice) specific siRNA sequence (ApoB1) used herein is:

```
Antisense:
P-5'Aj₈AAGUUGCCACCCACAUUCj₈AQ₂G

Sense:
R₂₀-5'GAAj₈UGj₈UGGGj₈UGGj₈CAAj₈Cj₈Uj₈Uj₈Uj₈AQ₂G
``` wherein:
"P" is a phosphate group,
"j$_8$" before nucleotide represents a 2'-methoxy modified nucleotide,
"Q2" represents a phosphorothioate linker,
R$_{20}$ is —(CH$_2$)$_6$—SH linked to the 5' end Example 1

Synthesis of PHF-EDA

PHF (70,000 Da, 2 g, 14.81 mmol PHF monomer) was dissolved in 60 mL anhydrous DMF, followed by the addition of bis(nitrophenol) carbonate (2.93 g, 9.63 mmol). The solution was stirred at 40° C. for 4 hours, cooled to ambient temperature and then added slowly to a solution of ethylenediamine (8.9 g 148 mmol) in 30 mL anhydrous DMF. The resulting solution was stirred at ambient temperature for 18 hours then diluted with 900 mL deionized water. The pH of the solution was adjusted to 5.5 with 1N HCl. The product (PHF-EDA) was purified by diafiltration against 4 volumes of deionized water and the resulting PHF-EDA polymer was recovered by lyophilization (75% yield). The fraction of the total PHF monomer units substituted with EDA was 0.47, as determined by elemental analysis.

By varying the reaction conditions described above it is possible to obtain modified polymer with varying amounts (molar fraction between about 0.02 and about 0.90 inclusive) of ethylenediamine or other amino moieties ($Z_1$, $Z_2$, $Z_3$, $Z_4$, $Z_5$, and $Z_6$). Also using conditions similar to those described above, PHF polymers containing a mixture of at least two diamino moieties, such as, conjugates #46, 53, 59 and 60 in Table I, were synthesized.

It is also possible to append varying amounts of functional groups to the modified polyacetal polymer using the methods described below. For example, it is possible to vary the relative amounts of targeting group, charge group, charge modifying group, hydrophobic group, protective group, and polynucleotide. The analytical methods provided in Example 16, below, can be used to determine the relative amounts of each component.

Example 2

Synthesis of PHF-EDA-NAG

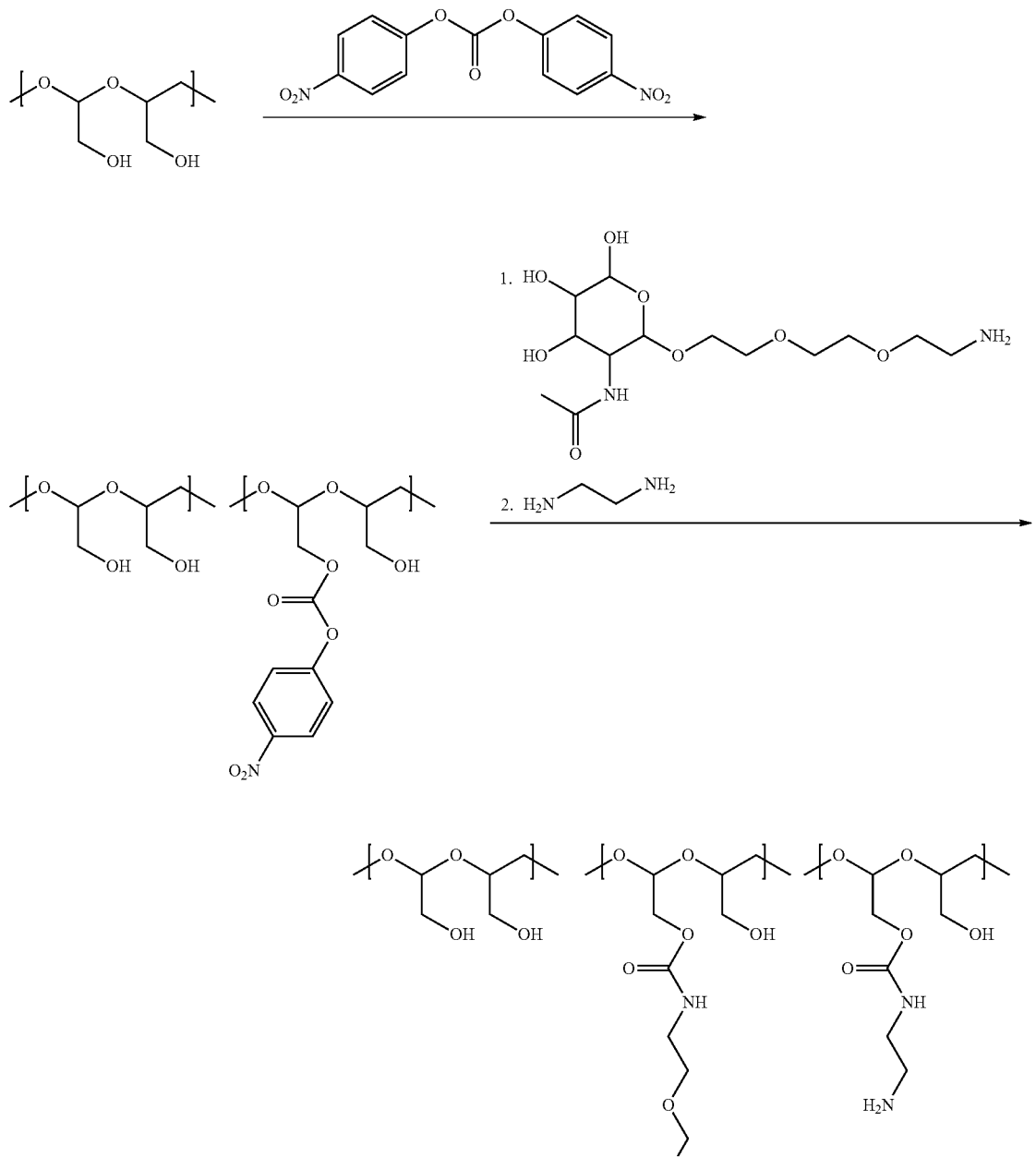

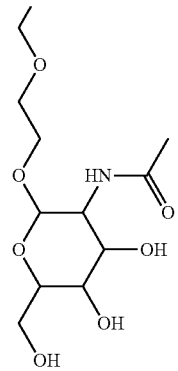

PHF (70,000 Da, 2 g, 14.81 mmol PHF monomer) was dissolved in 60 mL anhydrous DMF, followed by the addition of bis(nitrophenol) carbonate (2.93 g, 9.63 mmol). The solution was stirred at 40° C. for 4 hours, cooled to ambient temperature and then combined with N-(2-(2-(2-aminoethoxy)ethoxy) NAG ($R_I$ variable 2, 0.125 g, 0.444 mmol) dissolved in 2 mL anhydrous DMF. After one hour of agitation the reaction mixture was added slowly to ethylenediamine (8.9 g 148 mmol) in 30 mL anhydrous DMF. The resulting solution was stirred at ambient temperature for 18 hours then diluted with 900 mL deionized water. The pH was adjusted to 5.5 with 1N HCl. The product was purified by diafiltration against 4 volumes of deionized water and the resulting PHF-EDA-NAG was recovered by lyophilization.

By varying the reaction conditions described above it is possible to obtain modified polymer with varying amounts of NAG or other targeting groups ($R_I$).

Example 3

Synthesis of PHF-EDA-SSPy

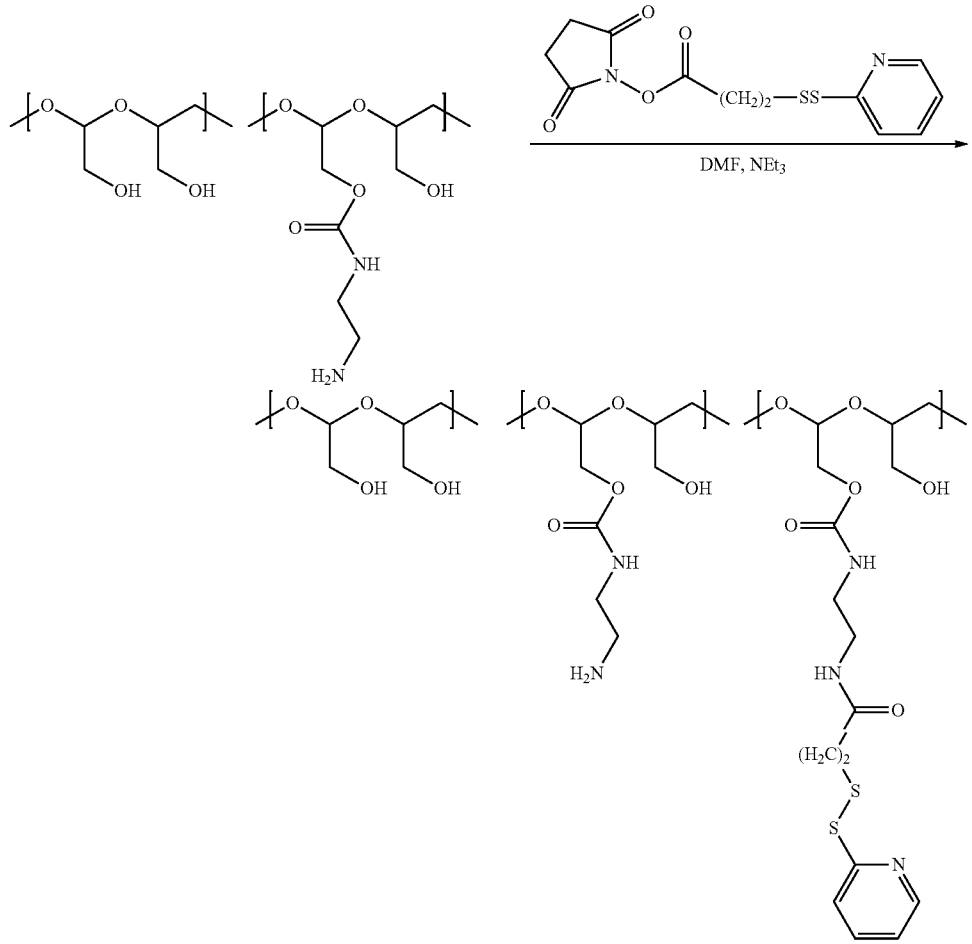

PHF-EDA (100 mg) prepared as described in Example 1, was dissolved in 10 mL anhydrous DMF and combined with SPDP (5 mg, 3% (mol) per PHF monomer) dissolved in 1 mL anhydrous DMF, following by the addition of 1 mL triethylamine. The resulting solution was stirred at ambient temperature for 2 hours, followed by the addition of 0.1 M phosphate buffer, pH 6.0, 100 mL. The resulting product was recovered by diafiltration against 4 volumes of deionized water. Purified PHF-EDA-SSPy solution was stored frozen at −40° C. until further use. The fraction of the total PHF monomer units substituted with SSPy was 0.02, as estimated by pyridinethione spectrophotometric analysis.

Example 4

Synthesis of PHF-EDA-SS-siRNA

PHF-EDA-SSPy (10.6 mg in 1 mL water, prepared as described in Example 3) was combined with ApoB1 siRNA-hexylene-SH (0.82 mg, siRNA/PHF monomer mol=0.5) dissolved in 1M triethylammonium acetate buffer, pH 8.5, 1 mL. The solution was stirred at room temperature for 2 hours. The resulting PHF-EDA-SS-siRNA was used as is or after dialysis against PBS (50 mM phosphate, pH 7.0, 0.9% NaCl). Analysis of the purified PHF-EDA-SS-siRNA by AEX HPLC showed conjugated siRNA content >95%.

By varying the reaction conditions described above it is possible to obtain modified polymer with varying amounts of siRNA (ApoB1) or other polynucleotides ($R_6$).

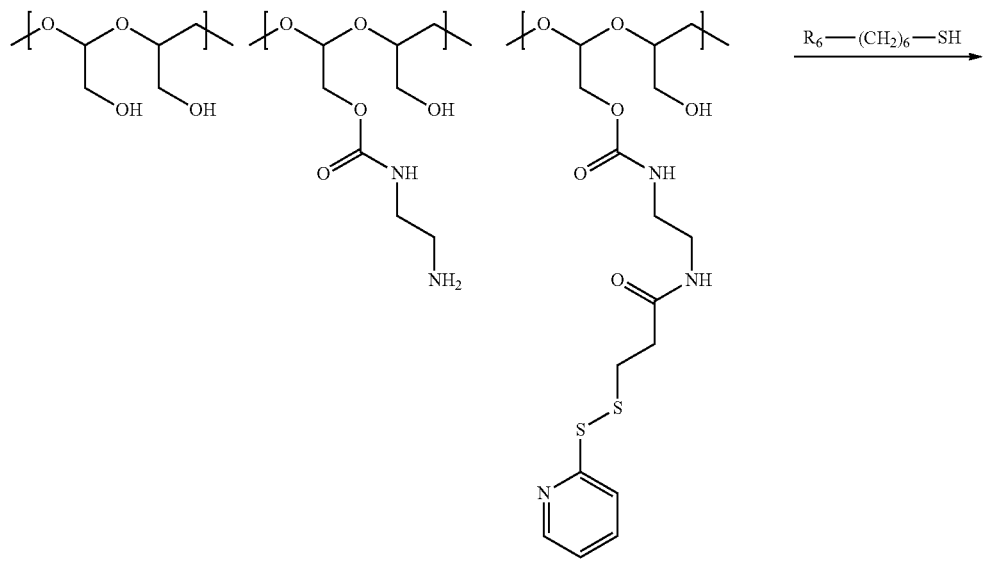

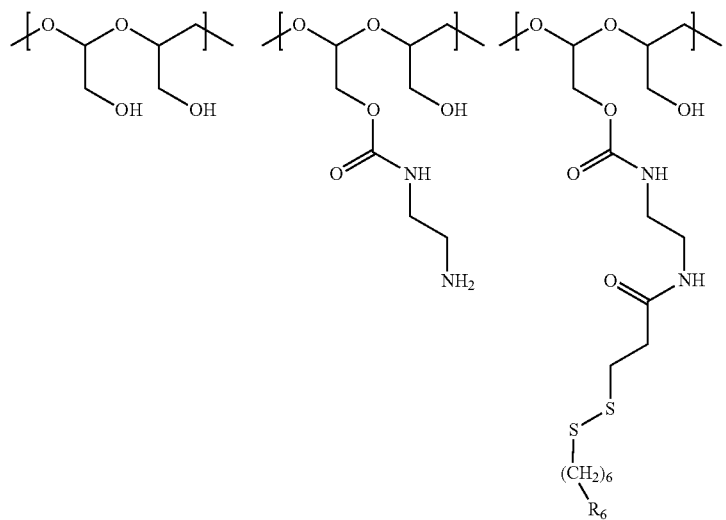

Example 5

Synthesis of PHF-EDA-SS-siRNA-Hexanoate

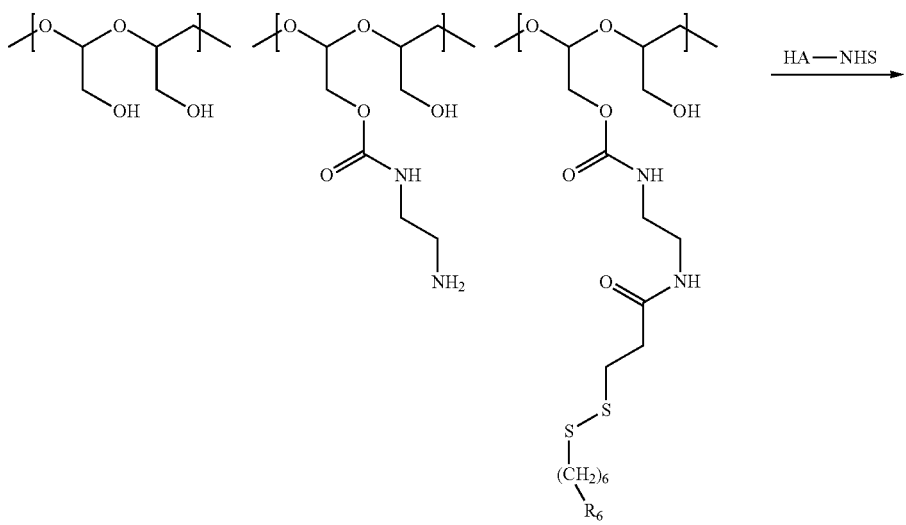

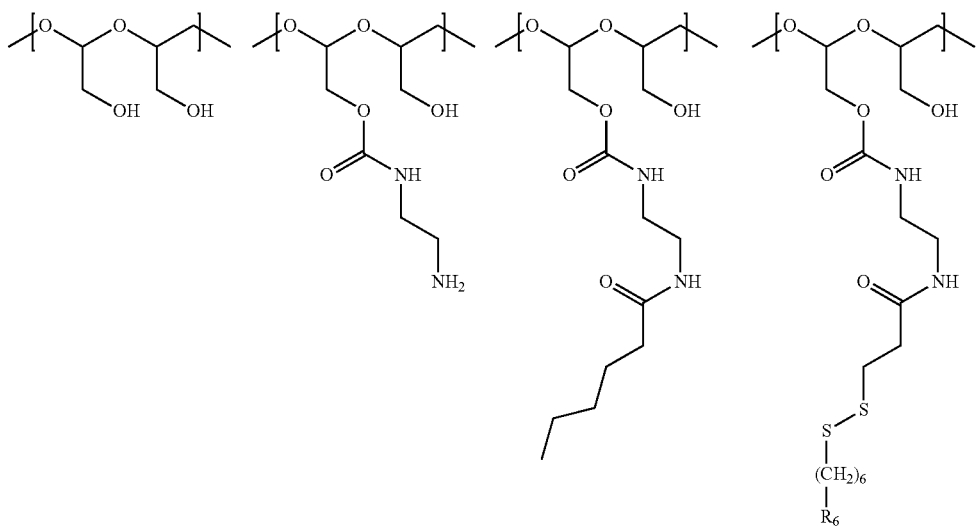

The pH of PHF-EDA-SS-siRNA solution (prepared as described in Example 4) was adjusted to pH 7.5-8.0 using 5% NaHCO$_3$, then 0.6 mL DMF was added followed by the addition of HA-NHS (0.39 mg) dissolved in 0.4 mL anhydrous DMF. The resulting solution was stirred for 2 hours. The product (68% hexanoic acid incorporated by HPLC), was diluted with 5 mL PBS (50 mM phosphate pH 7.0, 0.9% NaCl) and purified by diafiltration against 4 volumes of PBS. Analysis of the purified PHF-EDA-SS-siRNA-hexanoate by AEX HPLC showed conjugated siRNA content >95%.

By varying the reaction conditions described above it is possible to obtain modified polymer with varying amounts of hexanoate or other hydrophobic groups ($R_5$).

Example 6
Synthesis of PHF-EDA-SS-siRNA-Hexanoate-NAG₃
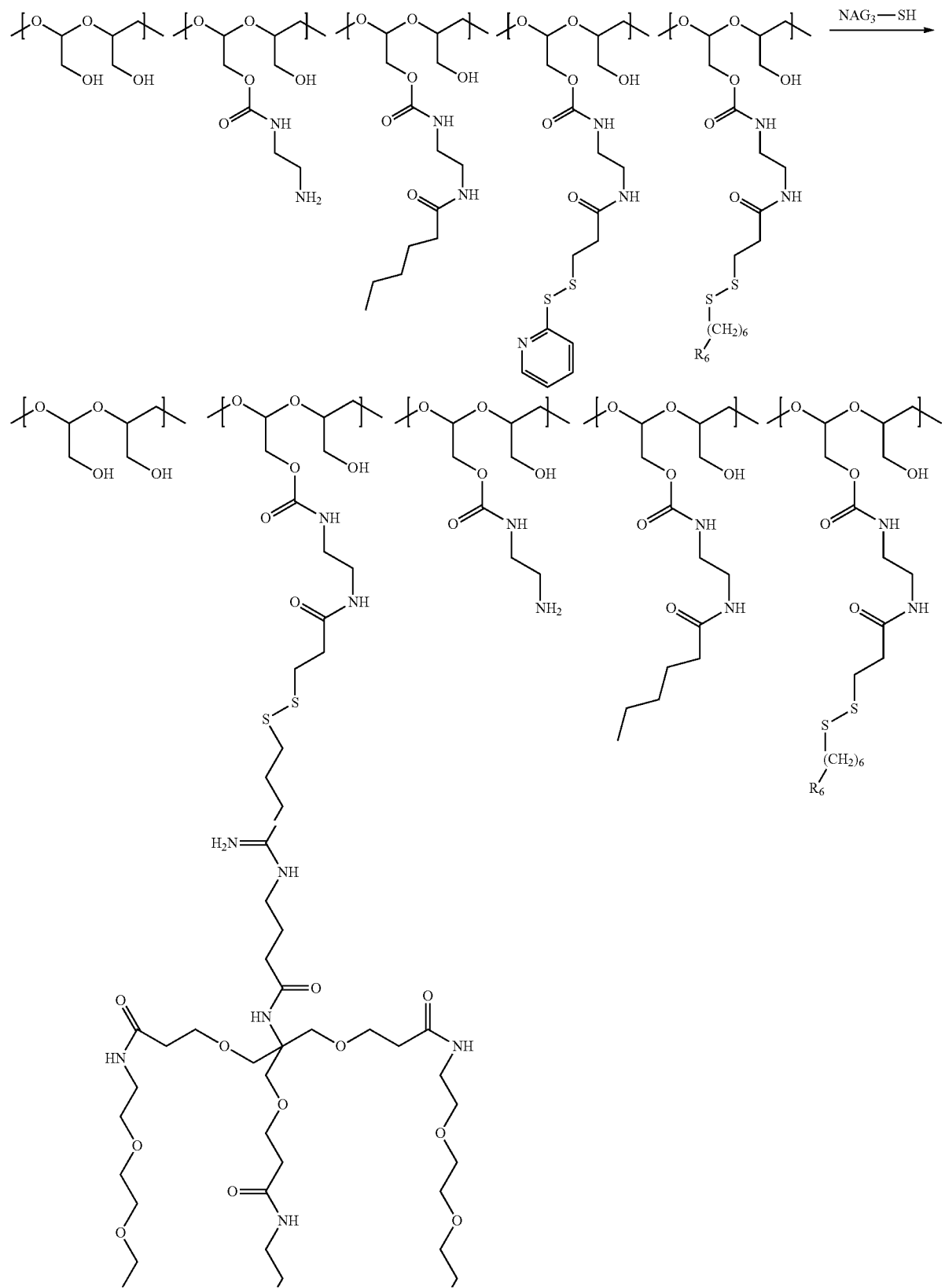

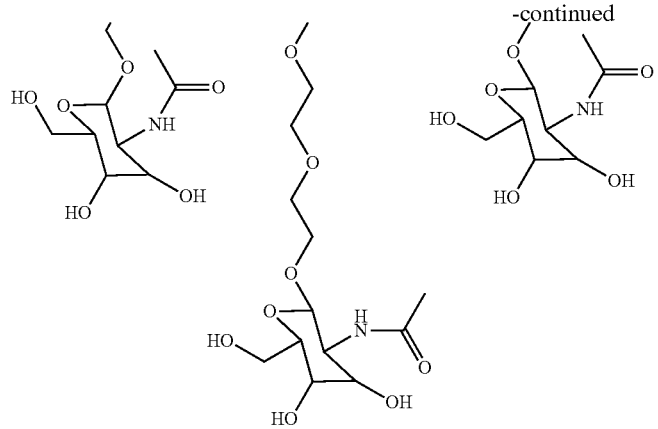

To PHF-EDA-SS-siRNA-hexanoate, prepared as described in Example 5, was added NAG$_3$-SH (1.8 mg, NAG$_3$-SH, prepared in situ by reaction of compound of Formula XI, variable 2, with iminothiolane (0.12 mg) in 0.2 mL DMF). The resulting solution was stirred for 2 hours. The product (PHF-EDA-SS-siRNA-hexanoate-NAG$_3$, by HPLC analysis showed quantitative incorporation of NAG$_3$) was diluted with 5 mL PBS (50 mM phosphate pH 7.0, 0.9% NaCl) and purified by diafiltration against 4 volumes of PBS. Analysis of the purified PHF-EDA-SS-siRNA-hexanoate-NAG$_3$ by AEX HPLC showed conjugated siRNA content >95%.

By varying the reaction conditions described above it is possible to obtain modified polymer with varying amounts of NAG$_3$ or other targeting groups (R$_T$).

Example 7

Synthesis of PHF-PEI

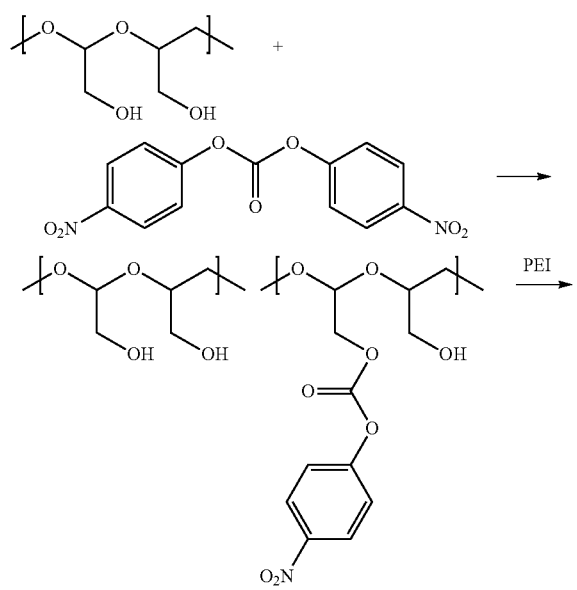

-continued

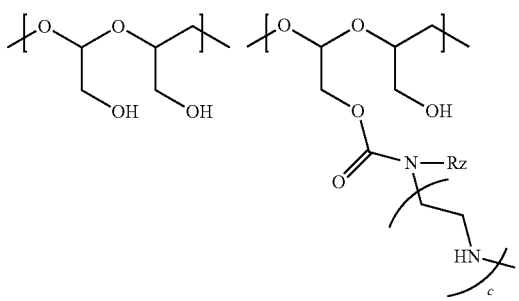

PHF (70,000 Da, 2 g, 14.81 mmol PHF monomer) was dissolved in 30 mL anhydrous DMF, followed by the addition of bis(nitrophenol) carbonate (0.137 g, 0.45 mmol) and the resulting solution was stirred at 40° C. for 4 hours. Separately linear PEI (PEI-linear MW 2500 Da, 1.35 mmol, 3.375 g) was dissolved in 100 mL water, after pH adjustment to 5.5 with 1N HCl, chilled on ice, then to it was added slowly the PHF-nitrophenol carbonate solution and the pH of the resulting mixture was adjusted to 7.5-8.0 with triethylamine. The solution was stirred overnight then the pH was adjusted to 5.5 with 1N HCl. The product was purified by diafiltration against 4 volumes of deionized water and the resulting PHF-PEI polymer was recovered by lyophilization (65% yield). The fraction of the total PHF monomer units substituted with PEI was 0.03, as estimated by elemental analysis.

By varying the reaction conditions described above it is possible to obtain modified polymer with varying amounts of PEI or other polyamino moieties (R$_2$ and Z$_8$). It is also possible to append varying amounts of functional groups to the modified polyacetal polymer as described below. For example, it is possible to vary the relative amounts of targeting group, charge group, charge modifying group, hydrophobic group, protective group, and polynucleotide. The analytical methods provided in Example 16, below, can be used to determine the relative amounts of each component.

Example 8

Synthesis of PHF-PEI-SSPy

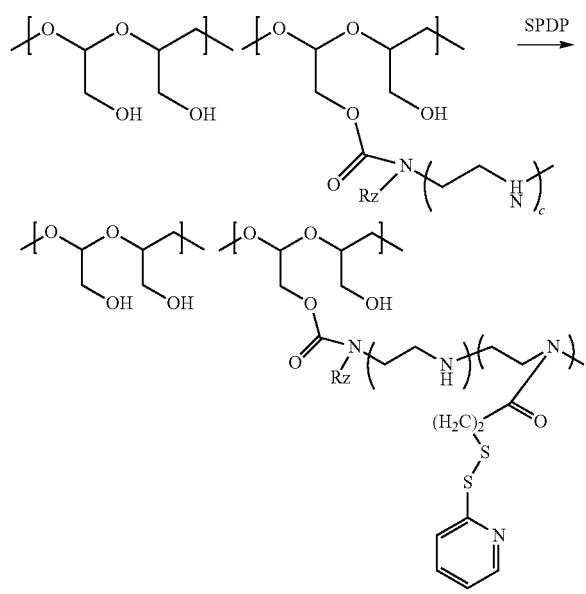

PHF-PEI (prepared as described in the Example 7, 519 mg) was dissolved in 20 mL DMF and 10 mL deionized water. The pH of the solution was adjusted to pH 8.0-8.1 with 1N NaOH. To the mixture on ice was added SPDP (66 mg) dissolved in 3 mL DMSO. The reaction mixture was kept on ice for 2 hours then the pH adjusted to pH 5.5-6.0 followed by dilution to 150 mL with deionized water. The resulting PHF-PEI-SSPy polymer was purified by diafiltration against 4 volumes of deionized water and concentrated to approximately 20 mg/mL using Millipore Pelican system equipped with 30,000 Da MW cut-off membrane. The purified polymer was lyophilized. Analysis by $^1$H NMR and UV spectroscopy showed that the fraction of the total PHF monomer units substituted with SSPy was 0.02.

Example 9

Synthesis of PHF-PEI-SS-siRNA

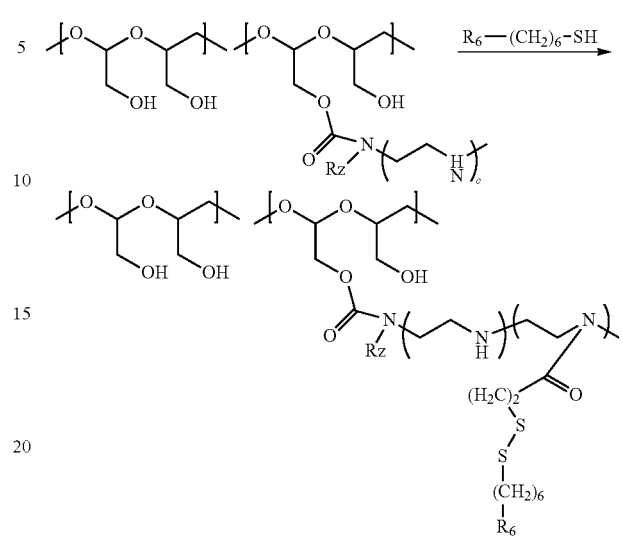

PHF-PEI-SSPy (prepared as described in the Example 8, 78 mg polymer in 4 mL deionized water) was combined with 3 mL 1M triethylammonium acetate buffer pH 8.5. Then ApoB 1 siRNA-hexylene-SH (5 mg, siRNA/PHF-PEI=0.6) was added. The resulting PHF-PEI-SS-siRNA was used as is or after dialysis against PBS (50 mM phosphate, pH 7.0, 0.9% NaCl). Analysis of the purified PHF-EDA-SS-siRNA by AEX HPLC showed conjugated siRNA content >95%.

By varying the reaction conditions described above it is possible to obtain modified polymer with varying amounts of siRNA (ApoB1) or other polynucleotides ($R_6$).

Example 10

Synthesis of PHF-PEI-SS-siRNA-Cholesterol

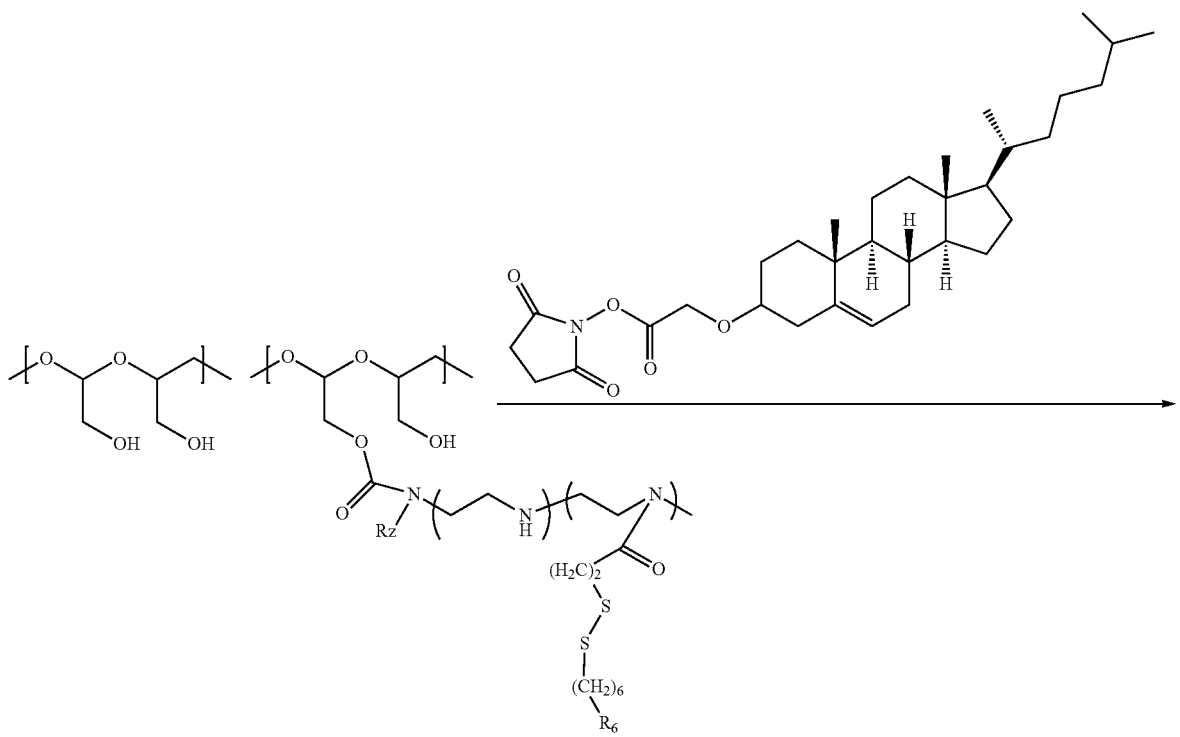

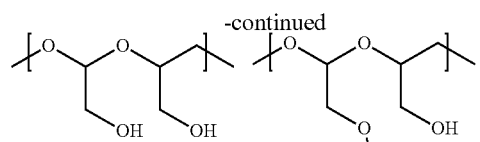
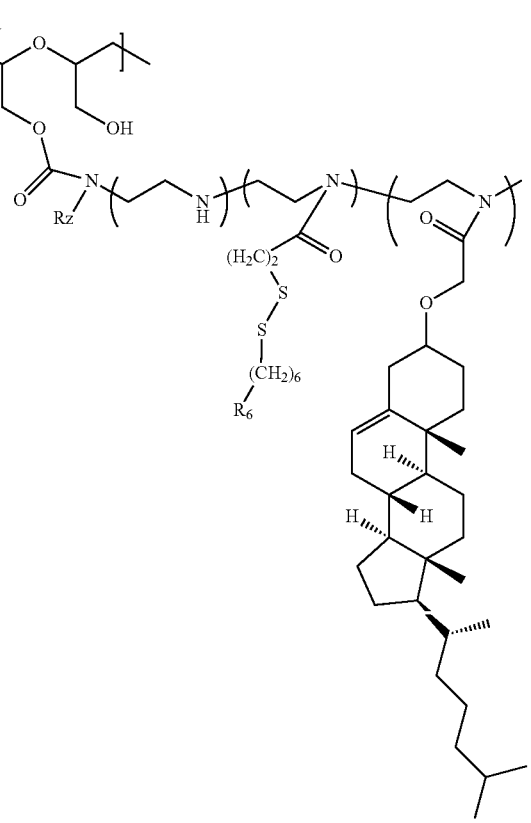

PHF-PEI-SS-siRNA, (prepared as described in Example 9, 4 mg, siRNA/PHF-PEI=0.5) was mixed with 3 mL of DMF and pH of the solution was adjusted to pH 7.5-8.0 using 5% NaHCO$_3$ solution. The resulting solution was combined with NHS derivative of cholesterol (R$_4$, variable 7, 4 mg) dissolved in anhydrous DMF. The solution was stirred for 2 hours. The resulting PHF-PEI-SS-siRNA-cholesterol conjugate was diluted with 50 mL PBS (50 mM phosphate pH 7.0, 0.9% NaCl) and purified by diafiltration against 4 volumes of PBS. HPLC analysis showed quantitative incorporation of the cholesterol compound. Analysis of the purified PHF-PEI-SS-siRNA-cholesterol conjugate by AEX HPLC showed conjugated siRNA content >95%.

By varying the reaction conditions described above it is possible to obtain modified polymer with varying amounts of cholesterol derivatives or other hydrophobic groups (R$_5$).

Example 11

Synthesis of PHF-PEI-SS-siRNA-cholesterol-NAG$_3$

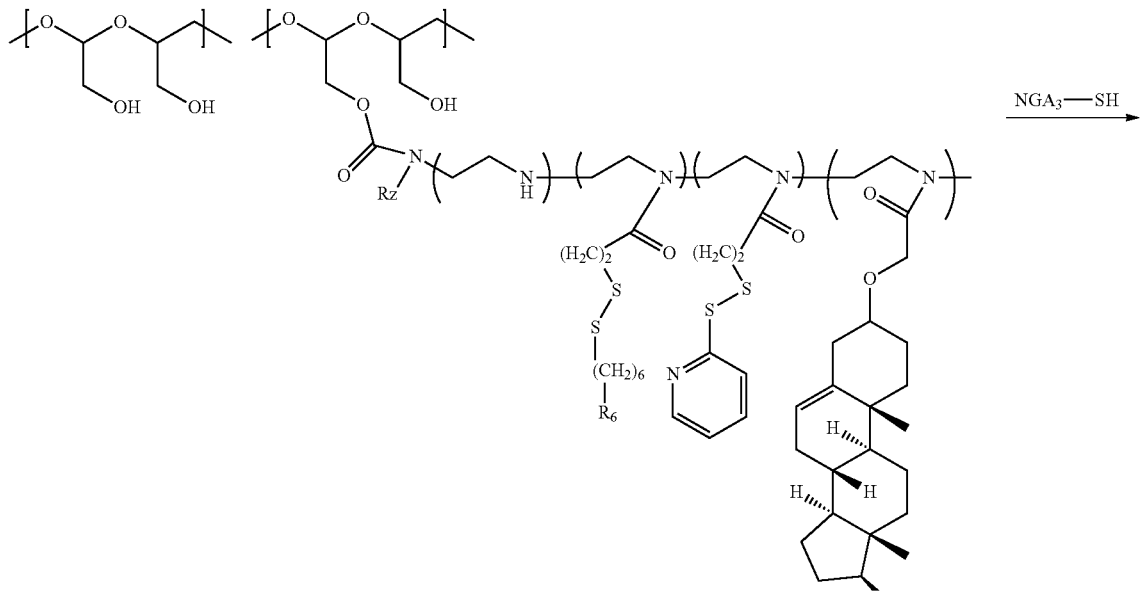

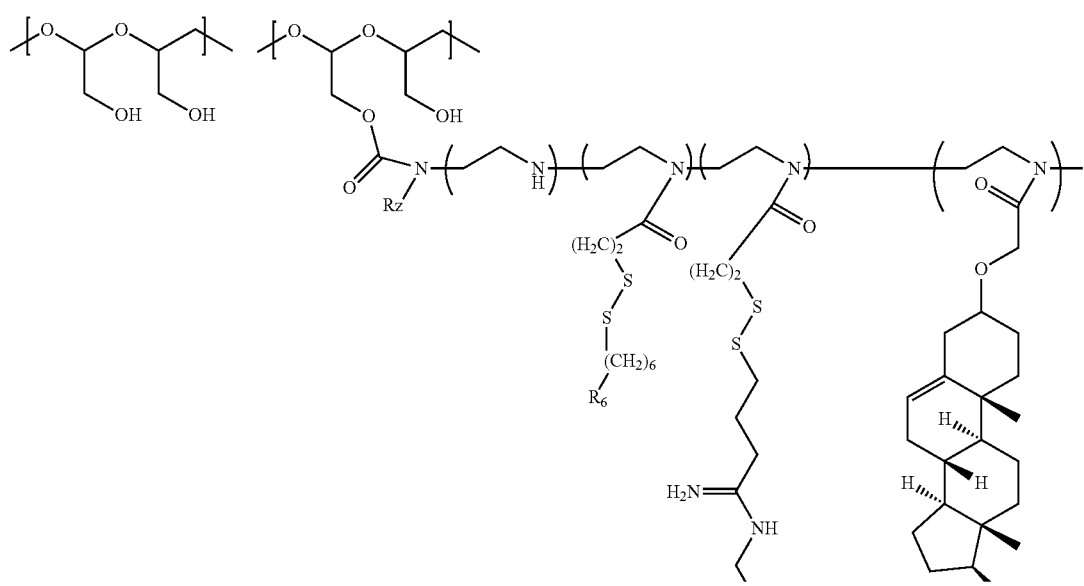
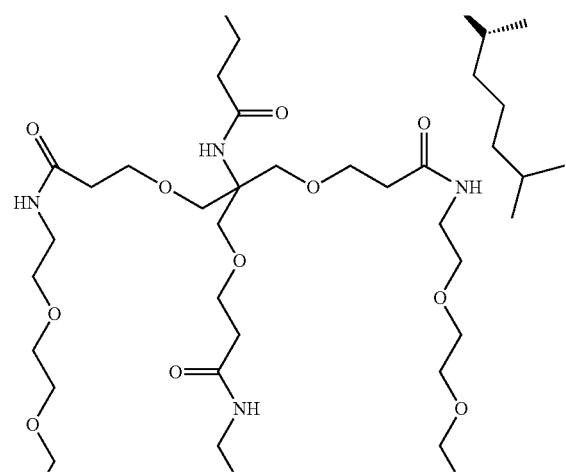

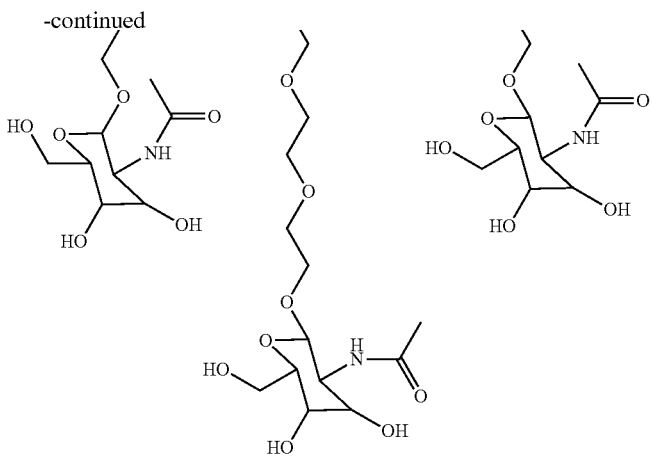

The PHF-PEI-SS-siRNA conjugate (prepared as described in Example 9 siRNA/PHF-PEI ratio of 0.5, 4 mg), was mixed with 3 mL of DMF and pH was adjusted to pH 7.5-8.0 using 5% NaHCO₃ solution. The resulting solution was combined with NHS derivative of cholesterol (R₄, variable 7, 1.3 mg) dissolved in anhydrous DMF. After 2 hours of agitation, NAG₃-SH (1.8 mg, NAG₃-SH, prepared in situ by reaction of compound of Formula XI, variable 2, with iminothiolane (0.12 mg) in 0.2 mL DMF) was added to the solution and agitation was continued for 2 hours. The resulting PHF-PEI-SS-siRNA-cholestrol-NAG₃ conjugate was diluted with 50 mL of PBS (50 mM phosphate pH 7.0, 0.9% NaCl) and purified by diafiltration against 4 volumes of PBS. Analysis of the purified PHF-PEI-SS-siRNA-cholesterol-NAG₃ conjugate by AEX HPLC showed conjugated siRNA content >95%.

By varying the reaction conditions described above it is possible to obtain modified polymer with varying amounts of NAG₃ or other targeting groups (R₁).

Example 12

Preparation of Phf-Ga-Butyldiamine

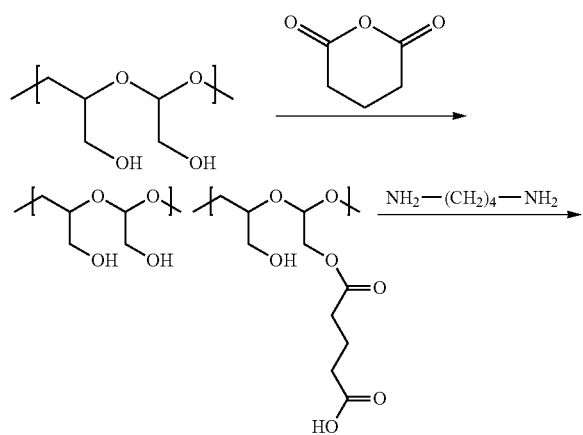

4-N,N-Dimethylamino pyridine (0.268 g, 2.91 mmol) and glutaric anhydride (1.375 g, 12.06 mmol) was added to a solution of PHF (30,000 Da, 1.48 g, 10.96 mmol PHF monomer) in 300 mL DMA and 33.3 mL anhydrous pyridine. The reaction mixture was stirred at 60° C. for 18 h. The solvents were removed under reduced pressure and the resulting thick oil was taken up in 100 mL water. The pH was adjusted to pH 6.0-6.5 with 5N NaOH. The resulting clear solution was diluted to 200 mL with water, filtered through a 0.2 micron filter, and purified by diafiltration using a membrane filter, 5000 molecular weight cut-off. The water was removed by lyophilization to give 1.28 g PHF-GA as a white solid (48% yield). The fraction of the total PHF monomer units substituted with glutaric acid as determined by ¹H NMR was 0.96%.

N-hydroxysuccinimide (0.579, 5.03 mmol) and butane-1,4-diamine (3.00 mL, 30.2 mmol) were added to PHF-GA in water (26.2 mL). The resulting solution was cooled to 0° C. and N-(3-dimethylaminopropyl)-N'-ethylcarbodiimide hydrochloride (1.93 g, 10.1 mmol) was added portion wise over 3 hours. The mixture was allowed to warm to ambient temperature, pH adjusted to pH 5.5-6.0 and agitation was continued for 18 h. The resulting polymer product was purified by diafiltration using a membrane filter, 5000 molecular weight cut-off. The volume was reduced to 10 mL and PHF-GA-Butyldiamine was washed on the membrane with water (3×50 mL). Purified polymer was recovered by lyophilization to give PHF-GA-Butyldiamine as a white solid (1.03 g, 62.1% yield). Amine analysis by pycrylsulfonic acid assay showed that the fraction of the total PHF monomer units substituted with the amines was 0.72.

Example 13

Preparation of Phf-Ga-Butyldiamine-Ha-Ssp

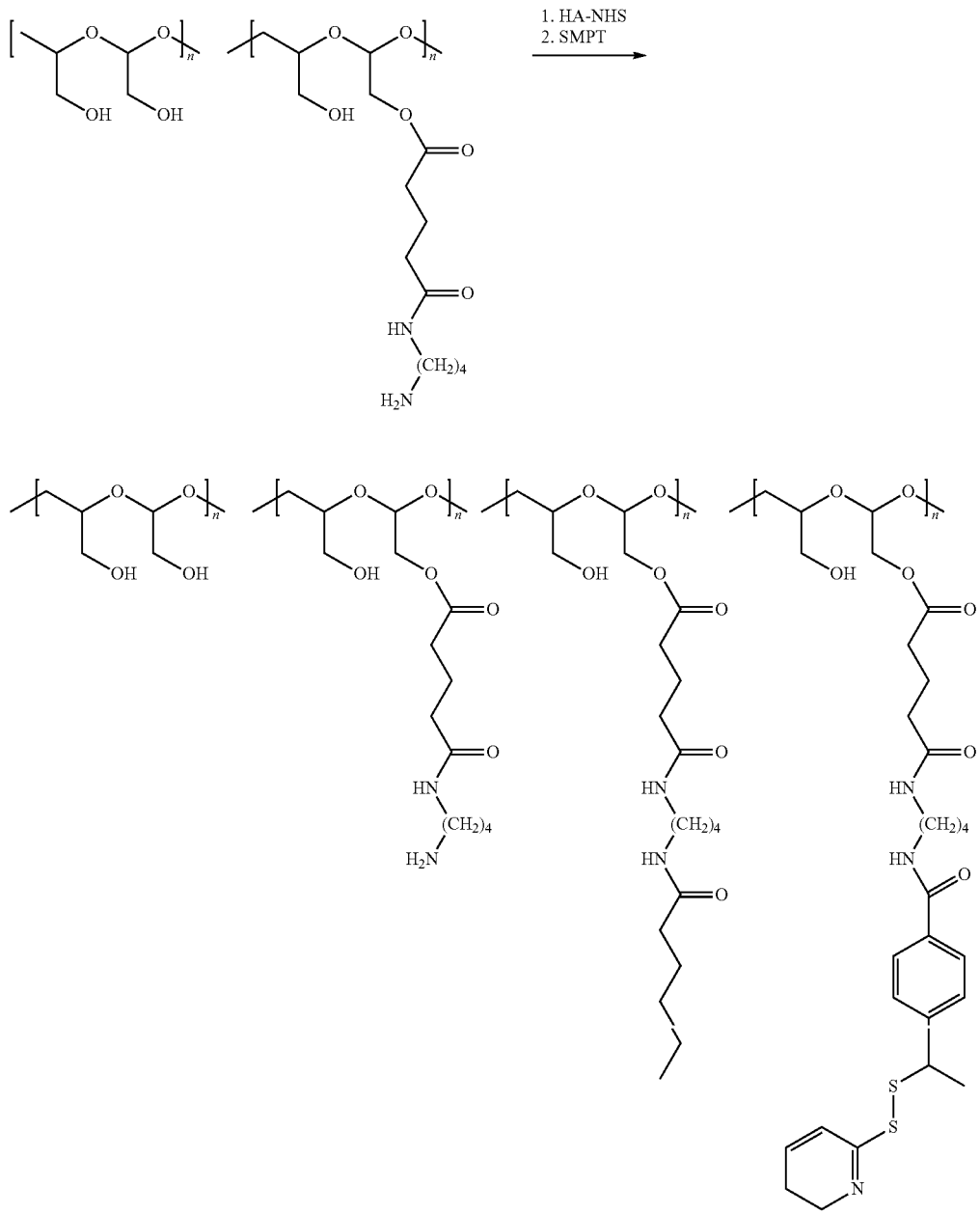

2,5-Dioxopyrrolidin-1-yl-4-(1-(pyridin-2-yldislufanyl) ethyl)benzoate (SMPT, 15.2 mg, 0.039 mmol) in 2 mL DMF was added to a solution of PHF-GA-Butyldiamine (prepared as described in Example 12, 211 mg, 0.677 mmol) in 2 mL DMF and 0.500 mL water. The pH of the mixture was adjusted to pH 7.5 and the reaction mixture stirred at 20-23° C. for 1 h. Then 2,5-dioxopyrrolidin-1-yl hexanoate (85.0 mg, 0.398 mmol) was added and the stirring continued at ambient temperature for 18 h. The pH of the resulting mixture was adjusted to pH 5.0-5.5 then the solution was filtered through a 0.2 micron filter. The resulting product was purified by diafiltration using a membrane filter, 5000 molecular weight cut-off. The volume was reduced to 2 mL and PHF-GA-Butyldiamine-HA-SSP was washed on the membrane with water (3×10 mL). The product, PHF-GA-butyldiamine-HA-SSP (151.2 mg, 57% yield) was diluted to concentration 10 mg/mL and stored at −40° C. until further use. $^1$H NMR analysis showed that the fraction of the total PHF monomer units substituted with hexanoate was 0.115. The fraction of the total PHF monomer units substituted with the disulfide was 0.011 as estimated by pyridinethione spectrophotometric analysis.

Example 14
Preparation of Phf-Ga-Butyldiamine-Ha-Ssp-siRNA
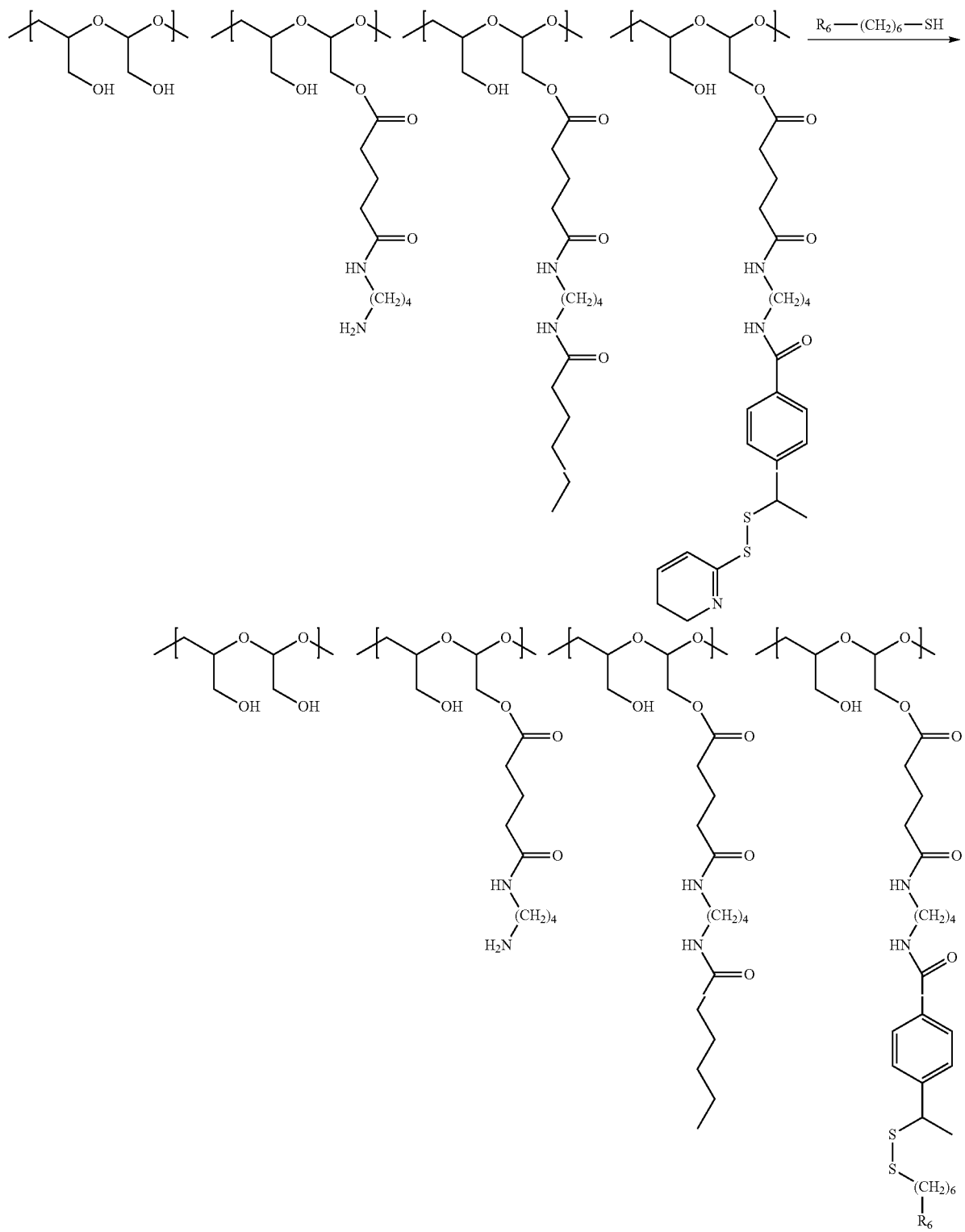
PHF-GA-Butyldiamine-HA-SSP (prepared as described in the Example 13, 5 mg) in 0.5 ml of deionized water was combined with 0.5 mL 1M triethylammonium acetate buffer pH 8.5. Then ApoB1 siRNA-hexylene-SH (0.41 mg, siRNA/PHF-PEI=0.5) was added. The resulting PHF-GA-Butyldiamine-HA-siRNA was used as is or after dialysis against PBS (50 mM phosphate, pH 7.0, 0.9% NaCl). Analysis of the purified PHF-EDA-SS-siRNA by AEX HPLC showed conjugated siRNA content >95%.

By varying the reaction conditions described above it is possible to obtain modified polymer with varying amounts of siRNA (ApoB1) or other polynucleotides ($R_6$).

Example 15

Conjugates Containing Charge Modifying Groups

Synthesis of polymers containing charge modifying groups can be prepared by the addition of the charge modifying compound $R_3$ (at a specific molar ratio or in excess of the reactive amines in the polymer), followed by adjustment of the pH of the resulting solution to pH 8.5-9.0 and diafiltration. The resulting polymer is stored at −40° C. until further use.

Example 16

Characterization and Analysis of Modified Polymers

High performance anion exchange chromatography (AEX HPLC) with UV detection were used for: i) determination of single and double stranded RNA concentration in preparations involving free or conjugated dsRNA; ii) determination of dsRNA in PBS, plasma and tissue extracts; iii) characterization of dsRNA stability.

Reverse-phase high performance liquid chromatography (RP HPLC) with UV detection or RP HPLC with mass spectrometry detection (RP-HPLC-MS) was used for: i) structural identification of single and double stranded RNA oligonucleotides; ii) identification of the products of RNA of degradation in vitro and in vivo samples, iii) quantitative determination of polymer content of hydrophobic modifiers and targeting groups.

A. Anion Exchange Chromatography (AEX HPLC)

AEX chromatography was carried using a DNAPac PA200 column (4×250 mm Dionex) at 40° C. The mobile phase system included i) mobile phase A (80% 25 mM dihydrogen phosphate pH 7/20% acetonitrile) and ii) mobile phase B (80% 0.4M sodium perchlorate in 25 mM phosphate pH 7/20% acetonitrile). Flow rate of 1.0 ml/min, 30 min linear gradient 15%-100% B was used for analytical determinations.

B. Reverse-Phase High Performance Liquid Chromatography with Mass Spectrometry Detection (RP-HPLC-MS)

RP-HPLC was conducted using a Xbridge OST $C_{18\ 2.5}$ m, 2.1×50 mm column (Waters), at 80° C. to dissociate the RNA duplexes. The mobile phase system consisted of i) mobile phase A (100 mM hexafluoroisopropanol and 1.7 mM triethlyamine, pH 7.5 and ii) mobile phase B (60% Phase A/40% Methanol). Flow rate 0.4 ml/minute, 12 min linear gradient 17%-50% B. Mass spectra collection and analysis was performed on an IonTrap Esquire 3000 (Bruker).

The quantitative analysis of charge modifying groups (i.e., CDM), both bound and free, was performed by RP LC MS/MS. Free charge modifying groups was recovered from the supernatant after precipitation of the polymer conjugate with acetonitrile (centrifugation at 16000 g for 2 min). The supernatant was analyzed by RP LC MS/MS using Acentis Express $C_{18}$ Column (3 cm×2.1 mm, 2.7 µm Supelco part #: 53802-U). The covalently bound charge modifying group content (after correction for free charge modifying groups) was determined using the same procedure after sample hydrolysis with 1M HCl (10 min, 37° C.). For instance, when CDM was used as the charge modifying group the mass transition monitored by the API 3200 Triple quadrupole mass spectrometer were 138.9 to 94.9 and 138.9 to 64.9 m/z.

Disulfide content in -SSPy or -SSP modified polymers was determined spectrophotometrically at 340 nm after pyridinethione release (10 mM DTT, 10 minutes, ambient temperature).

The amino content of the polymer conjugates was determined based on elemental analysis data. When more a mixture of amino moieties were used for the preparation of the conjugates, $^1$H NMR data was used to assign the fractional composition of the products.

The concentration of the modified polyacetal polymers in solutions was determined after lyophilization of the sample and correction for salt content (elemental analysis data) and residual water/VOC content (determination by drying to the constant weight).

Example 17

Stability of PHF siRNA Delivery System In Vitro

The polymers containing siRNA described herein have the particular The polymers containing siRNA described herein have the particular advantage of being stable over extended storage periods. Polymers described above and in Table I were assessed after 3, 6, or 9 months or longer in ambient storage conditions, and the stability of each functional side chain was determined. For example, analysis of conjugate #61, Table I, after 12 month storage at 2-8° C. showed >95% siRNA did not exhibit any duplex degradation Example 18

In Vitro Testing—Measurement of mRNA Knockdown with bDNA Assay

Many of the examples provided below utilize a siRNA directed against mouse ApoB. Accordingly, the methods describe in some detail the evaluation of such siRNA by quantitative RT-PCR, as well as evaluation of the mouse ApoB mRNA transcript by bDNA assay or quantitative RT-PCR. However, such methods can be used in the evaluation of active siRNAs directed against any transcript of interest, whether produced by an endogenous gene or by a reporter gene that has been introduced to a cell line, tissue, or animal of interest.

The purpose of the in vitro screening assay was to evaluate the ability of various formulations to deliver siRNA into tissue culture cells and carry out knockdown of the relevant mRNA transcript in those cells. Assay is done in a multiwell format, wherein multiple formulations can be evaluated in replicates and in parallel. Various cells can be used for this assay. In one example, Hepa 1-6 (mouse hepatoma) cells were used in the primary screening assay, and knockdown of the mouse ApoB mRNA transcript was measured, (alternatively, by stable introduction of reporter constructs containing relevant regions of the mouse ApoB sequence-regions overlapping and complementary to the siRNA being evaluated other non-liver or non-mouse cells can be used in such assays.)

Cells were plated at a density of 3,000-5,000 cells/well in a 96 well plate, 24 hrs later conjugates were added at the desired concentrations (range varies from 3.84 µM to 3.84 nM). Positive control siRNAs were transfected using Lipofectamine™ RNAiMax Transfection Reagent (Part No. 13778-075, Invitrogen) according to the manufacturer's instructions.

The bDNA assay was used to examine levels of specific mRNA transcripts, thereby serving as readout of siRNA knockdown both in vitro and in vivo. The bDNA assay is an extremely sensitive, homogeneous sandwich polynucleotide hybridization method assay in a plate format, allowing analysis of small amounts of sample in tissue culture cells or tissues harvested from animals. Samples were lysed and hybridized overnight to sequence-specific plate-immobilized probes, which capture the mRNA transcripts. Hybridized transcripts were detected by addition of specific probes with conjugated horseradish peroxidase, allowing quantitative detection upon substrate addition and measurement in a luminometer plate reader. The assay system is designed to amplify primary signal, making it very sensitive and quantitative. Analogous results can be obtained using quantitative RT-PCR.

For the example of screening ApoB siRNAs conjugates described herein, hepatocarcinoma cells, e.g. Hepa 1-6 cells, in culture were used for the determination of ApoB mRNA in total mRNA isolated from cells incubated with ApoB-specific siRNAs by branched DNA assay. Hepatocarcinoma cells were exposed to the conjugated described herein for designated periods of time, usually 24-72 hours. Conjugates were added directly to cells at concentrations in a range including but not limited to 3.84 µM to 3.84 nM at 37° C. The bDNA assay was carried out on the cells at the designated time endpoint, and levels of ApoB mRNA were determined relative to various controls (e.g. mock treated cells, cells treated with PHF, siRNA alone, or cells treated with PHF conjugated to an irrelevant siRNA). In each case, levels of an endogenous "housekeeping" gene which is known or presumed to be unaffected by the siRNA or delivery agent was also evaluated in order to normalize for overall efficiency of RNA extraction (i.e. yield of total RNA), cell toxicity, or both. GAPDH or actins are widely used for this purpose.

ApoB100 protein levels in cell supernatants and blood samples may be also measured by ELISA assay. Although the details of such analysis may vary with the availability and properties of specific reagents, an example of this assay is as follows: Polyclonal antibody goat anti-human-apolipoprotein B is diluted 1:1000 in phosphate buffered saline (PBS) and 100 µL of this dilution is coated on 96-well plates at 4° C. overnight. After blocking with 300 µL of 1% BSA in PBS the plate is washed with PBS. Cell culture supernatant is thawed and diluted 1:1 with PBS containing 0.1% Tween 20 and 0.1% BSA. 100 µL of this dilution is added to each well. After an incubation time, the plate is washed with PBS containing 0.1% Tween 20 followed by three washes with PBS. 100 µL of a horseradish-peroxidase conjugated Goat Anti-Human Apolipoprotein B-100 polyclonal antibody diluted 1:1000 in PBS containing 0.1% Tween 20 and 3% BSA is added to each well. The plate is incubated for 60 min at room temperature. After washing the plate with PBS containing 0.1% Tween 20 and three times with PBS, wells are incubated with 0.9 mg/mL o-phenylenediamine in 24 mmol/L citric acid buffer, pH 5.0, containing 0.03% hydrogen peroxide. The enzyme reaction is halted by adding 0.5 mol/L $H_2SO_4$ (Merck KgaA, Darmstadt, Germany, Cat. No. 100731) and absorbance at 490 nm is measured on a spectrophotometer. As described below, an analogous method may be used to quantify ApoB protein levels in samples from in vivo studies in which animals have been dosed with siRNA conjugates.

Table I gives the composition of the modified polymer used for the measurement of mRNA knockdown. The polymer conjugates were synthesized using the procedures described in Examples 1 to 15. Analyses of the conjugates include the methods described in Example 16. Based on mRNA levels of an endogenous GAPDH the conjugates in Table I were not toxic at concentrations ≦76.8 nM. Columns 5 to 11 of Table I, named by "$R_6$", "PHF" (i.e., unmodified PHF), "$R_1$", "$R_2$", "$R_2+Z_8$", "$R_3$" and "$R_4$", respectively, lists fractions of the unmodified PHF and fractions of total PHF monomer units modified by $R_1$, $R_2$, $R_2$ together with $Z_8$, $R_3$, and $R_4$. For illustration purposes a value of 0.2 in column 8 of Table I means that 1 PHF monomer out of 5 PHF monomers is modified by $R_2$.

TABLE I

| ID # | $R_2$ or $Z_8 + R_2$ | PHF MW | Linkage | $R_6{}^a$ | PHF | $R_1$ | $R_2$ | $R_2 + Z_8$ | $R_3$ | $R_4$ |
|---|---|---|---|---|---|---|---|---|---|---|
| 7 | EDA | 70,000 | carbamate | 0.017 | 0.70 | 0.03[b] | 0.14 | n/a | n/a | 0.1[c] |
| 46 | Mixed amines (IMA:EDA: GUA 3:1:1) | 70,000 | carbamate | 0.0010 | 0.46 | n/a | 0.51 | n/a | n/a | n/a |
| 53 | Mixed amines (IMA:EDA 4:"1) | 70,000 | carbamate | 0.0019 | 0.62 | n/a | 0.35 | n/a | n/a | n/a |
| 59 | Mixed amines (GUA:EDA 1:4) | 70,000 | carbamate | 0.0038 | 0.58 | n/a | 0.39 | n/a | n/a | n/a |
| 60 | Mixed amines (GUA:EDA 1:4) | 70,000 | carbamate | 0.0077 | 0.58 | n/a | 0.39 | n/a | n/a | n/a |
| 61 | EDA | 70,000 | carbamate | 0.0010 | 0.53 | n/a | 0.44 | n/a | n/a | n/a |
| 63 | EDA | 70,000 | carbamate | 0.0019 | 0.53 | n/a | 0.44 | n/a | n/a | n/a |
| 64 | EDA | 70,000 | carbamate | 0.0038 | 0.53 | n/a | 0.44 | n/a | n/a | n/a |
| 67 | PEI branched (MW 1200) | 70,000 | carbamate | 0.0019 | 0.97 | n/a | n/a | 0.03 | n/a | n/a |
| 75 | PEI branched (MW 800) | 70,000 | carbamate | 0.0115 | 0.93 | n/a | n/a | 0.07 | n/a | n/a |
| 76 | PEI branched (MW 800) | 70,000 | carbamate | 0.0154 | 0.93 | n/a | n/a | 0.07 | n/a | n/a |
| 81 | PEI linear (MW 2500) | 70,000 | carbamate | 0.0014 | 0.97 | n/a | n/a | 0.03 | n/a | n/a |
| 82 | PEI linear (MW 2500) | 70,000 | carbamate | 0.0019 | 0.97 | n/a | n/a | 0.03 | n/a | n/a |
| 88 | PEI linear (MW 2500) | 70,000 | carbamate | 0.0231 | 0.97 | n/a | n/a | 0.03 | n/a | n/a |

TABLE I-continued

| ID # | R$_2$ or Z$_8$ + R$_2$ | PHF MW | Linkage | R$_6$$^a$ | PHF | R$_1$ | R$_2$ | R$_2$ + Z$_8$ | R$_3$ | R$_4$ |
|---|---|---|---|---|---|---|---|---|---|---|
| 91 | Tetraethylene-pentamine | 70,000 | carbamate | 0.0010 | 0.91 | n/a | n/a | 0.09 | n/a | n/a |
| 95 | Tetraethylene-pentamine | 70,000 | carbamate | 0.0077 | 0.91 | n/a | n/a | 0.09 | n/a | n/a |
| 96 | Spermine | 70,000 | carbamate | 0.0010 | 0.88 | n/a | n/a | 0.12 | n/a | n/a |
| 105 | Triethylen-tetramine | 70,000 | carbamate | 0.0077 | 0.94 | n/a | n/a | 0.06 | n/a | n/a |
| 126 | EDA | 30,000 | carbamate | 0.0077 | 0.29 | n/a | 0.68 | n/a | n/a | n/a |
| 127 | EDA | 30,000 | carbamate | 0.0019 | 0.53 | n/a | 0.44 | n/a | n/a | n/a |
| 128 | EDA | 70,000 | carbamate | 0.0038 | 0.53 | n/a | 0.44 | n/a | n/a | n/a |
| 133 | Spermidine | 70,000 | carbamate | 0.0010 | 0.76 | n/a | n/a | 0.24 | n/a | n/a |
| 298 | PEI linear 2500 | 70,000 | carbamate | 0.0014 | 0.97 | 0.05$^d$ | n/a | 0.03 | n/a | n/a |
| 299 | PEI linear 2500 | 70,000 | carbamate | 0.0014 | 0.97 | 0.05$^d$ | n/a | 0.03 | 0.85$^e$ | n/a |
| 331 | PEI linear 2500 | 70,000 | carbamate | 0.0014 | 0.97 | n/a | n/a | 0.03 | 0.85$^e$ | n/a |
| 334 | PEI linear 2500 | 70,000 | carbamate | 0.0014 | 0.97 | n/a | n/a | 0.03 | n/a | 0.1$^f$ |
| 443 | Butyldiamine | 30,000 | Glutaric acid | 0.0015 | 0.04 | n/a | 0.72 | n/a | n/a | 0.5$^c$ |

$^a$ = ApoB100 siRNA.
$^b$ = R$_1$ structure (2) at paragraph [00154], wherein f is the integer 2
$^c$ = hexanoic acid
$^d$ = Formula (XI), structure (2)
$^e$ = CDM
$^f$ = R$_4$ structure (7) at paragraph [00203]

Table II gives the results for mRNA knockdown using the conjugates described in Table I at concentrations from 3.84 nM to 384 nM. ApoB mRNA knockdown was evaluated using the bDNA assay 48 hours after exposure. Most conjugates were assayed in triplicate.

TABLE II

| ID # | 384 nM | 154 nM | 76.8 nM | 38.4 nM | 15.4 nM | 7.68 nM | 3.84 nM |
|---|---|---|---|---|---|---|---|
| 7 | ## | # | # | # | # | # | NT |
| 46 | ### | ## | ## | # | # | # | NT |
| 53 | ## | # | # | # | # | # | NT |
| 59 | #### | #### | #### | ### | # | # | NT |
| 60 | # | # | # | # | # | # | NT |
| 61 | #### | #### | #### | ### | ## | ## | NT |
| 63 | #### | #### | ## | ## | # | # | NT |
| 64 | ## | # | # | # | # | # | NT |
| 67 | # | # | # | # | # | # | NT |
| 75 | ## | ## | ## | ## | ## | ## | NT |
| 76 | ## | ## | ## | ## | ## | ## | NT |
| 81 | ## | ## | # | # | # | # | NT |
| 82 | ### | ## | ## | ## | ## | ## | NT |
| 88 | ## | ## | ## | ## | ## | ## | NT |
| 91 | ## | ## | ## | ## | ## | ## | NT |
| 95 | #### | #### | #### | #### | #### | #### | NT |
| 96 | #### | #### | #### | #### | #### | #### | NT |
| 105 | ### | ## | ### | ## | ### | ## | NT |
| 126 | ## | # | # | # | # | # | NT |
| 127 | ### | ### | ### | ### | ### | ### | NT |
| 128 | ### | ### | ### | ### | ### | ### | NT |
| 133 | ### | ### | # | # | # | # | NT |
| 298 | #### | #### | #### | ### | # | # | NT |
| 299 | #### | #### | #### | ### | # | # | NT |
| 331 | #### | NT | #### | ## | NT | # | # |
| 334 | #### | NT | #### | ### | NT | # | # |
| 443 | NT | NT | ## | # | NT | # | # |

# = 0-24% knockdown;
## = 25-49% knockdown;
### = 50-74% knockdown;
#### = 75-100% knockdown;
NT = not tested.

Example 19

In Vivo Studies in Mice

In order to evaluate the performance and pharmacokinetics of polymer conjugates, formulations, and gene-specific knockdown in vivo, the following methods were used. Test articles, along with appropriate negative controls were administered intravenously (IV) via tail-vein injection. At designated times; whole blood, liver, jejunum, kidney, and lung, (as well as other organs or tissues as necessary) were collected. Blood was collected via terminal, cardiac-puncture at the specified pharmacokinetic time points into pre-chilled (0-4° C.) blood collection tubes and immediately divided into (3) aliquots: about 150 µL it of serum for liver panel testing, about 50 µL of plasma for cytokine testing, with the remainder of plasma preserved for bioanalytical testing (e.g. evaluation of siRNA levels). Aliquots for serum samples were centrifuged at 0-4° C. and immediately frozen at −80° C. Aliquots for plasma samples were collected into pre-chilled potassium EDTA containing tubes, centrifuged at 0-4° C., and immediately frozen at −80° C.

Organs and tissues were harvested at each time point, with collection occurring within 2 minutes of the terminal blood collection for each animal. Each tissue was dissected into an appropriate number of samples according to the various analyses conducted, snap-frozen on dry ice, and stored frozen at −80° C. until analysis. Portion of the tissues was immediately transferred to tubes containing RNAlater® (Applied Biosystems) and processed and stored as recommended by the manufacturer. Tissue samples were stored at the appropriate temperature. Test tissue blotted to remove excess RNAlater®, was finely minced on ice and weighed. Tissue was then stored at −80° C. until ready for testing. Tissue samples were evaluated both for quantitative determination of the amount of siRNA in the tissue as well as the bDNA or quantitative RT-PCR assay to determine mRNA knockdown in comparison to negative controls. When siRNAs targeting the ApoB gene was evaluated, levels of the mouse ApoB1 transcript were tested in this assay, and normalized to endogenous "housekeeping" genes such as GAPDH or Actin.

Table III represents an example of ApoB target gene knockdown in vivo in liver and in tumor tissue in the nude mouse xenograft model. Test articles were administered intravenously via tail-vein injection at 0.3 mg/kg dose; dosing volume was 10 ml/kg (0.200 ml/20 g). Tissues were harvested 48 hrs after injection; 4 animals per group were used. The composition of conjugate ID# 61 and #81 are given in Table I.

TABLE III

| Test article | Vehicle (normal saline) | Unconjugated (ApoB1 siRNA in normal saline) | Conjugate #61 | Conjugate #81 |
| --- | --- | --- | --- | --- |
| Tumor | | | | |
| Mean RQ normalized by actin | 0.97 | 0.82 | 0.48 | 0.50 |
| Std. Deviation | 0.13 | 0.13 | 0.06 | 0.25 |
| Liver | | | | |
| Mean RQ normalized by actin | 1.06 | 0.91 | 0.58 | 0.46 |
| Std. Deviation | 0.09 | 0.13 | 0.06 | 0.26 |

RQ = relative quantification

The result above showed that, in tumors, conjugate #61 and conjugate #81 each showed about 50% knockdown of mRNA, as compared to 15% knockdown of mRNA by unconjugated siRNA; and in liver, conjugate #61 showed about 45% knockdown and conjugate #81 showed about 56% knockdown of mRNA, as compared to 14% knockdown of mRNA by unconjugated siRNA.

Alternatively, such assays can be carried out to evaluate gene specific knockdown of other mRNAs in vivo: knockdown of other endogenous transcripts, transcripts generated by reporter constructs, or transcripts within implanted tumors can be tested when siRNA sequences recognizing these transcripts are administered in a test article that is being evaluated. Typical negative controls for such studies include, but are not limited to equivalent amounts of unformulated siRNA, as well as siRNA conjugates that lack either siRNA or a targeting group or both. In addition, siRNA duplexes unrelated to any mouse gene are used as control.

In other examples, siRNA directed against a transgene expressed in the mouse may be used, and evaluation of the knockdown of that siRNA conjugate evaluated by quantitative measurement of the respective transgene. In many cases such a transgene may be a reporter gene such as luciferase or GFP, and may be expressed ubiquitously or in a tissue specific manner.

Tissue testing for siRNA mediated knockdown: For the bDNA Assay tissue samples from in vivo were first homogenized in Trizol reagent, using 1 ml of Trizol per 25 mg of tissue. The tissue was homogenized using a TissueLyser II (Qiagen) at 25 Hz for 3 min, repeating as necessary until all tissue is lysed. Chloroform was added at a concentration of 0.2 mL per 1 mL Trizol and shaken by hand. The samples were then centrifuged to separate the phases and the top aqueous layer was tested in the bDNA assay at a range of 1 µg to 200 µg. Typically, the concentration and amount of total RNA in a sample is quantified by measuring absorbance at 260 nM. Quality of the RNA can also be assessed qualitatively by gel electrophoresis. A gene specific probe is used for testing of the amount of mRNA of the target gene (as well as appropriate controls and normalization standards). In one specific example in which knockdown of ApoB mRNA in mouse liver is evaluated, QuantiGene 2.0 Assay Kit (Part No. QS0010), and QuantiGene 2.0 Probe Sets for mouse ApoB (Part No. SB-10032-$O_2$) and mouse GAPDH (Part No. SB-10001-02) are used (Affymetrix/Panomics). Assay results are read using a SpectraMax plate reader (Molecular Devices).

Knockdown can also be assessed using quantitative PCR methods. Tissue was homogenized as in the bDNA assay and RNA extracted using the PureLink™ RNA Micro Kit. Reverse transcription was performed using RNA at concentrations in a range of 0.01 µg to 1 µg with the TaqMan Reverse Transcription Reagents (Applied Biosystems, Part No., N808-0234). Using an ApoB specific TaqMan Gene Expression Assay and either GAPDH or Actin Gene Expression Assays as a control, qPCR was performed on 1-10 µl of the RT reaction with TaqMan Universal PCR Master Mix (Applied Biosystems, Part No. 4304437).

PK assay for quantitative evaluation of siRNA in plasma: Samples are thawed on ice and siRNA extracted using the mirVana™ Paris™ Kit (Part No. AM1556, Applied Biosystems). Extracted siRNA is then reverse transcribed using the TaqMan® MicroRNA Reverse Transcription Kit (Part No. 4366596, Applied Biosystems) and RT primers specific for the antisense strand of ApoB siRNA from the Custom TaqMan® Small RNA Assay ID CCJ9VOR (Part No. 450008, Applied Biosystems). Quantitative PCR is then performed using 2×TaqMan® Universal PCR Master Mix, No AmpErase® UNG (Part No. 4324018, Applied Biosystems) and qPCR Primers from the Custom TaqMan® Small RNA Assay ID CCJ9VOR (Part No. 450008, Applied Biosystems). Standard curves were generated by spiking known amounts of ApoB1 siRNA (500 ng to 32 pg) was added to untreated plasma samples and then treated the same way as the test samples from Paris Kit extraction to qPCR. The test samples were compared to the Standard curve to generate absolute amounts of siRNA present in the test samples.

For PK studies of siRNA in organs or tissues 10 mg to 50 mg tissue sample is weighed and the siRNA extracted using the mirVana™ Paris™ Kit (Part No. 4366596, Applied Biosystems) or Exiqon miRCURY RNA Isolation Kit—Tissue (Part No. 300111). RNA is then reverse transcribed using the TaqMan® MicroRNA Reverse Transcription Kit (Part No. 4366596, Applied Biosystems) and RT primers specific for the antisense strand of ApoB siRNA from the Custom TaqMan® Small RNA.

Assay ID CCJ9VOR (Part No. 450008, Applied Biosystems). Quantitative PCR is then performed using 2×TaqMan® Universal PCR Master Mix, No AmpErase® UNG (Part No. 4324018, Applied Biosystems) and qPCR Primers from the Custom TaqMan® Small RNA Assay ID CCJ9VOR (Part No. 450008, Applied Biosystems). qPCR Ct values are normalized to endogenous control mouse siRNA 202 (Part No. 4380914, Applied Biosystems), or an appropriate analogous endogenous miRNA, expression of which is known or believed not to be affected by the siRNA or delivery agent being evaluated. Standard curves are generated by spiking known amounts of ApoB1 siRNA (500 ng to 32 pg) into homogenized untreated tissue samples and then processed as per the test samples from Paris Kit extraction to qPCR. The test samples were compared to the Standard curve used to calculate absolute amounts of siRNA present in the test samples.

In one example, Nu/nu mice bearing Hepa 1-6 xenograft tumors were administered with conjugate #81 at 0.3 mg/kg, conjugate #61 at 1.0 mg/kg dose level and unconjugated ApoB1 siRNA at 3 mg/kg (all doses based on siRNA). Tissues from liver, jejunum, kidney, lung and tumor were harvested at pre dose and at 1 min, 5 min and 1 h post administration. For each of conjugates #61 and #81 accumulations in each of the different organs were 10-100 times higher relative to unconjugated siRNA controls. Conjugate #61 showed the highest tumor accumulation of siRNA, peaking at 5 min and was ~100 times higher than unconjugated siRNA.

In addition to determination of the dose-dependent knockdown activity of the siRNA conjugates, the toxicity associated with the conjugates was also evaluated. Liver panel testing included evaluation of the following parameters: albumin, alkaline phosphatase, ALT, AST, CK, GGT, total bilirubin, direct bilirubin, indirect bilirubin, and total protein. Significant article-related changes in these parameters were monitored for indications of toxicity or lack of tolerability associated with the test article being evaluated. In addition, IFNγ, TNFα, IL-6 and IL-12p70 in plasma were also assayed by standard ELISA methods, in order to determine whether the conjugated siRNAs have provoked interferon or other innate immune response, an undesirable occurrence often associated with other known systemic siRNA delivery technologies. Mice were also observed for other notable or adverse clinical signs throughout the in-life phase of these studies.

In one example, mice were administered conjugate #81 at 3 mg/kg (based on siRNA) and blood was collected at 48 hours post dose. Biochemical analysis shown no significant changes in blood biochemistry markers, including, alkaline phosphatase, ALT, AST, CK, GGT, total bilirubin, direct bilirubin, indirect bilirubin, and total protein, and no significant changes in cytokines IFNγ, TNFα, IL-6 and IL-12 relative to control mice (i.e. mice treated with vehicle only or unconjugated siRNA).

Other parameters associated with hemolysis or erythrocyte aggregation may also be evaluated. Such mechanisms of toxicity are known to be associated with certain delivery vehicles.

Preferred embodiments of this invention are described herein, including the best mode known to the inventors for carrying out the invention. Variations of those preferred embodiments can become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Equivalents

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A modified polyacetal of Formula (VI):

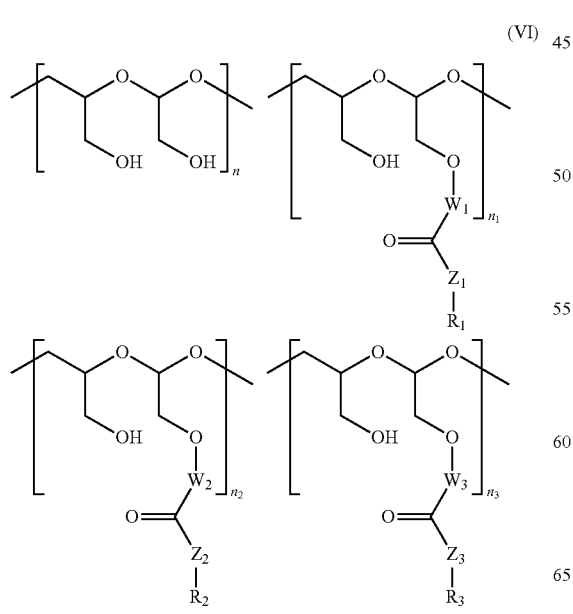

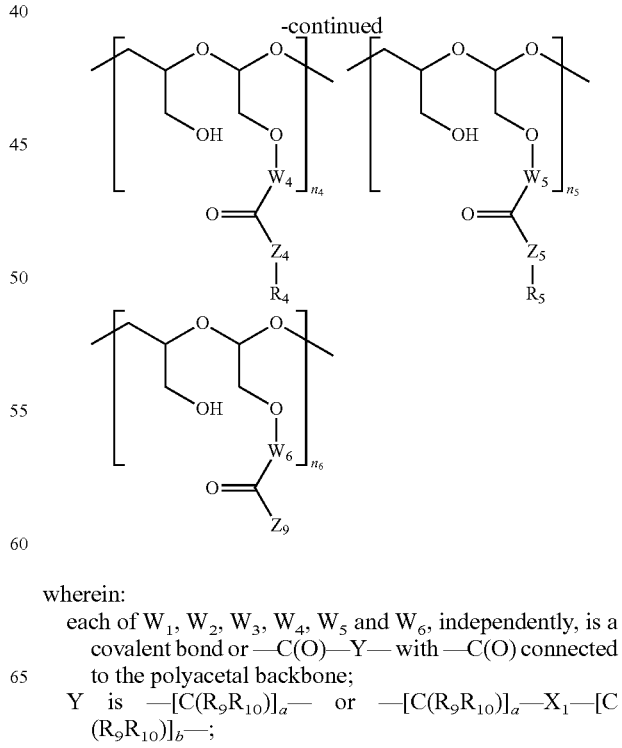

wherein:
each of $W_1$, $W_2$, $W_3$, $W_4$, $W_5$ and $W_6$, independently, is a covalent bond or —C(O)—Y— with —C(O) connected to the polyacetal backbone;

Y is —[C($R_9 R_{10}$)]$_a$— or —[C($R_9 R_{10}$)]$_a$—$X_1$—[C($R_9 R_{10}$)]$_b$—;

$X_1$ is an oxygen atom, a sulfur atom or —$NR_{11}$;

each of $R_9$ and $R_{10}$ independently is hydrogen, $C_{1-6}$ alkyl, $C_{6-10}$ aryl, 5 to 12-membered heteroaryl or $C_{3-8}$ cycloalkyl;

$R_{11}$ is hydrogen, $C_{1-6}$ alkyl, $C_{6-10}$ aryl, 5 to 12-membered heteroaryl, $C_{3-8}$ cycloalkyl or —C(O)—$C_{1-3}$ alkyl;

$Z_9$ is $Z_6$-$T_1$ or $Z_8$;

$T_1$ is —$Z_7$—$R_6$;

$Z_8$ is a linear or branched polyamino moiety substituted with one or more —$Z_7$—$R_6$ and optionally substituted with one or more substituents selected from the group consisting of -Q-$R_1$, -Q-$R_3$, -Q-$R_4$, and -Q-$R_5$;

each Q independently is a covalent bond or —C(O)—;

each of $Z_1$, $Z_2$, $Z_3$, $Z_4$, $Z_5$, and $Z_6$, independently, is a covalent bond, —$NR_{17}$, or —$NR_{17}R_{18}$—, in which each of $R_{17}$ and $R_{18}$ independently is H, $C_{2-8}$ alkyl, or —$C_{2-10}$ alkyl-N($R_x$)—, $R_x$ being H or an amino acid attached to the nitrogen via the carbonyl group of the amino acid; or $R_{17}$ and $R_{18}$, together with the nitrogen atom to which they are attached form a 4 to 7-membered heterocycloalkyl ring containing 0 or 1 additional heteroatom selected from N, O, and S;

each $Z_7$ independently is —C(O)-$T_2$-$T_3$- or —N(R')-$T_2$-$T_3$- with $T_3$ connected to $R_6$, in which R' is H or $C_{1-6}$ alkyl, $T_2$ is selected from alkylthioaryl, arylthioalkyl, alkylthioalkyl, arylthioaryl, alkyldithioaryl, aryldithioalkyl, alkyldithioalkyl and aryldithioaryl, and $T_3$ is a covalent bond, —C(O)N(R'')—$C_{1-8}$ alkyl, —N(R'')C(O)—$C_{1-8}$ alkyl, or $C_{1-8}$ alkyl, in which R'' is H or $C_{1-6}$ alkyl;

each of a and b independently is an integer between 1 and 6 inclusive;

each of n, $n_1$, $n_2$, $n_3$, $n_4$, $n_5$, and $n_6$ is the molar fraction of the corresponding polyacetal unit ranging between 0 and 1; $n+n_1+n_2+n_3+n_4+n_5+n_6=1$; provided that neither n nor $n_6$ is 0;

$R_1$ is a targeting group for a selected tissue, pathogen, cell, or cellular location;

$R_2$ is a charge group optionally substituted with one or more substituents selected from the group consisting of -Q-$R_1$, -Q-$R_3$, -Q-$R_4$, and -Q-$R_5$;

$R_3$ is a charge-modifying group;

$R_4$ is a hydrophobic group;

$R_5$ is a protective group;

$R_6$ is a polynucleotide;

the ratio ($m_1$) of the number of $R_1$ to the total number of polyacetal units of the polyacetal is 0 to 0.25;

the ratio ($m_3$) of the number of $R_3$ to the total number of polyacetal units of the polyacetal is 0 to 100;

the ratio ($m_4$) of the number of $R_4$ to the total number of polyacetal units of the polyacetal is 0 to 30;

the ratio ($m_5$) of the number of $R_5$ to the total number of polyacetal units of the polyacetal is 0 to 0.03;

the ratio ($m_6$) of the number of $R_6$ to the total number of polyacetal units of the polyacetal is 0.0004 to 0.10; and the polyacetal backbone has a molecular weight of about 10 kDa to about 250 kDa.

2. The modified polyacetal of claim 1, wherein $m_1$ is 0.002 to 0.25;

$m_3$ is 0.002 to 100;

$m_4$ is 0.03 to 0.30; and $m_5$ is 0.01 to 0.03.

3. The modified polyacetal of claim 1, wherein when $Z_9$ is $Z_6$-$T_1$, (i) $n_1$ is not 0 and each of $n_2$, $n_3$, $n_4$, and $n_5$ is 0;
(ii) neither $n_1$ nor $n_2$ is 0 and each of $n_3$, $n_4$, and $n_5$ is 0;
(iii) none of $n_1$, $n_2$ and $n_3$ is 0 and each of $n_4$ and $n_5$ is 0;
(iv) none of $n_1$, $n_2$ and $n_4$ is 0 and each of $n_3$ and $n_5$ is 0;
(v) none of $n_1$, $n_2$, $n_3$ and $n_4$ is 0 and $n_5$ is 0;
(vi) neither $n_1$ nor $n_4$ is 0 and each of $n_2$, $n_3$ and $n_5$ is 0;
(vii) $n_2$ is not 0 and each of $n_1$, $n_3$, $n_4$, and $n_5$ is 0;
(viii) neither $n_2$ nor $n_3$ is 0 and each of $n_1$, $n_4$ and $n_5$ is 0;
(ix) neither $n_2$ nor $n_4$ is 0 and each of $n_1$, $n_3$ and $n_5$ is 0;
(x) none of $n_2$, $n_3$ and $n_4$ is 0 and each of $n_1$ and $n_5$ is 0;
(xi) none of $n_1$, $n_2$, $n_3$, $n_4$, and $n_5$ is 0; or
(xii) each of $n_1$, $n_2$, $n_3$, $n_4$, and $n_5$ is 0.

4. The modified polyacetal of claim 1, wherein when $Z_9$ is $Z_6$-$T_1$, n is between about 0.01 and about 0.9996 inclusive;

$n_1$ is between about 0.002 and about 0.25 inclusive;

$n_2$ is between about 0.02 and about 0.90 inclusive;

$n_3$ is between about 0.02 and about 0.81 inclusive;

$n_4$ is between about 0.03 and about 0.30 inclusive;

$n_5$ is between about 0.01 and about 0.03 inclusive; and $n_6$ is between about 0.0004 and about 0.10 inclusive.

5. The modified polyacetal of claim 1, wherein when $Z_9$ is $Z_8$, each of $n_1$, $n_3$, $n_4$, and $n_5$ is 0, and $R_2$ is a linear or branched polyamino moiety optionally substituted with one or more substituents selected from the group consisting of -Q-$R_1$, -Q-$R_3$, -Q-$R_4$, and -Q-$R_5$.

6. The modified polyacetal of claim 1, wherein when $Z_9$ is $Z_8$, (i) $m_1$ is not 0 and each of $m_3$, $m_4$ and $m_5$ is 0;
(ii) neither $m_1$ nor $m_4$ is 0 and each of $m_3$ and $m_5$ is 0;
(iii) none of $m_1$, $m_4$ and $m_5$ is 0 and $m_3$ is 0;
(iv) neither $m_1$ nor $m_3$ is 0 and each of $m_4$ and $m_5$ is 0;
(v) none of $m_1$, $m_3$ and $m_4$ is 0 and $m_5$ is 0; or
(vi) none of $m_1$, $m_3$, $m_4$ and $m_5$ is 0.

7. The modified polyacetal of claim 1, wherein when $Z_9$ is $Z_8$, n is between about 0.70 and about 0.99 inclusive;

each of $n_1$, $n_3$, $n_4$, and $n_5$ is 0;

$m_1$ is 0.002 to 0.25;

$m_3$ is 0.002 to 100;

$m_4$ is 0.03 to 0.30;

$m_5$ is 0.01 to 0.03; and $m_6$ is 0.0004 to 0.10.

8. The modified polyacetal of claim 1, wherein each of $Z_1$, $Z_2$, $Z_3$, $Z_4$, $Z_5$, and $Z_6$, independently, is ethylenediamine, piperazine, bis(piperidine), 1,3-diaminopropane, 1,4-diaminobutane, 1,5-diaminopentane, decamethylenediamine, hexamethylenediamine, lysine, histidine, arginine, tryptophan, agmatine or ornithine.

9. The modified polyacetal of claim 8, wherein each of $Z_1$, $Z_2$, $Z_3$, $Z_4$, $Z_5$, and $Z_6$ is

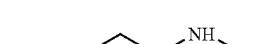

10. The modified polyacetal of claim 1, wherein $Z_7$ is:

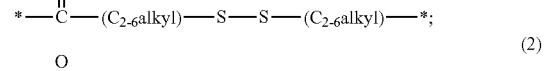

(3)

$$*-\overset{O}{\underset{}{C}}-Aryl-S-S-Aryl-\overset{O}{\underset{}{C}}-\underset{H}{N}-(C_{2\text{-}6}\text{alkyl})-*;$$

(4)

$$*-\underset{H}{N}-(C_{2\text{-}6}\text{alkyl})-S-S-(C_{2\text{-}6}\text{alkyl})-*; \text{ or}$$

(5)

$$*-\overset{O}{\underset{}{C}}-(C_{2\text{-}6}\text{Alkyl})-S-S-(C_{2\text{-}6}\text{Alkyl})-\overset{O}{\underset{}{C}}-\underset{H}{N}-(C_{2\text{-}6}\text{alkyl})-*;$$

wherein —C(O) or —NH is oriented towards the polyacetal backbone.

11. The modified polyacetal of claim 10, wherein $Z_7$ is:

(1)

[structure: aryl ketone with —S—S—(CH$_2$)$_6$—*]

(2)

[structure: alkyl ketone with —S—S—(CH$_2$)$_6$—*; or]

(3)

[structure: alkyl ketone with —S—S— and NH—(CH$_2$)$_6$—*]

wherein —C(O) is oriented towards the polyacetal backbone.

12. The modified polyacetal of claim 1, wherein $Z_8$, when otherwise unsubstituted, is:

(1)

[structure with $R_z$, subscript $c$, H]

(2)

[structure with $R_z$, $R_y$, subscripts $d$, $e$, H]

(3)

*—HN—(CH$_2$)—N(H)—(CH$_2$)—NH$_2$;

(4)

*—HN—(CH$_2$)—N(H)—C(=NH)—NH$_2$;

(5)

*—HN—(CH$_2$)—N(H)—(CH$_2$)—N(H)—(CH$_2$)—NH$_2$;

(6)

*—HN—(CH$_2$)$_3$—[imidazole];

(7)

*—[(L)-Lys]$_{d_3}$;

(8)

*—[(L)-Arg]$_{d_2}$;

or (9) a dendrimer of any of generations 2-10 selected from poly-L-lysine, poly(propyleneimine) and poly(amidoamine) dendrimers;

wherein:
$R_y$ is an amino acid attached to the nitrogen via the carbonyl group of the amino acid or a linear or branched polyamino moiety;
$R_z$ is H or a linear or branched polyamino moiety;
$c$ is an integer between 2 and 600 inclusive;
$d$ is an integer between 0 and 600 inclusive;
$e$ is an integer between 1 and 150 inclusive;
$d_2$ is an integer between 2 and 20 inclusive; and
$d_3$ is an integer between 2 and 200 inclusive.

13. The modified polyacetal of claim 12, wherein $Z_8$, when otherwise unsubstituted, is:
(1) a linear polyethylenimine having a molecular weight of about 500 to about 25000 dalton;
(2) a branched polyethylenimine having a molecular weight of about 500 to about 25000 dalton;

[structure with tyrosine group and OH] or;

[structure with histidine group]

14. The modified polyacetal of claim 13, wherein $Z_8$, when otherwise unsubstituted, is a linear polyethylenimine having a molecular weight of about 500 to about 2500 dalton or a branched polyethylenimine having a molecular weight of about 500 to about 1200 dalton.

15. The modified polyacetal of claim 12, wherein each of $R_y$ and $R_z$, independently, is a polyamino moiety comprising a monomer unit of —[C$_{2\text{-}6}$ alkyl-NH]—.

16. The modified polyacetal of claim 1, wherein $R_1$ comprises galactosamine, galactose, N-acetylgalactosamine, folic acid, RGD peptides, LHRH receptor targeting peptides, ErbB2 (HER2) receptor targeting peptides, prostate specific membrane bound antigen (PSMA) targeting peptides, lipoprotein receptor LRP1 targeting ligands, ApoE protein derived peptides or transferrin.

17. The modified polyacetal of claim 1, wherein $R_2$ is:

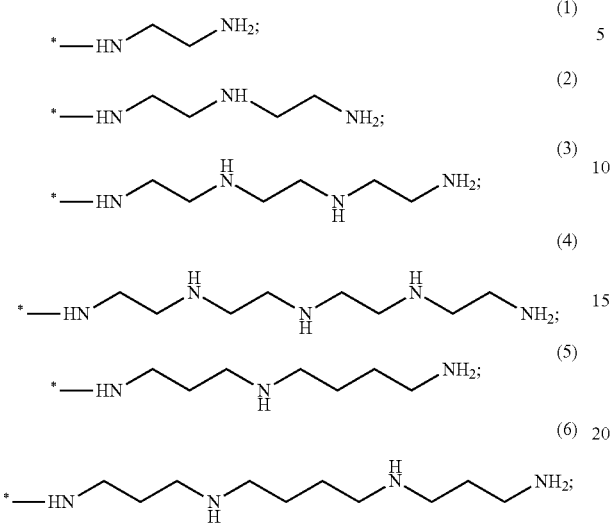

(7) a linear polyethylenimine having a molecular weight of about 500 to about 25000 dalton;

(8) a branched polyethylenimine having a molecular weight of about 500 to about 25000 dalton;

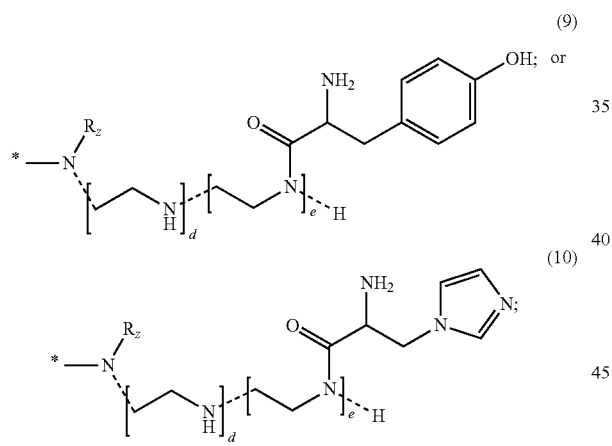

wherein $R_z$ is H or a linear or branched polyamino moiety;

d is an integer between 0 and 600 inclusive; and e is an integer between 1 and 150 inclusive.

18. The modified polyacetal of claim 1, wherein $R_3$ is of Formula (XVI):

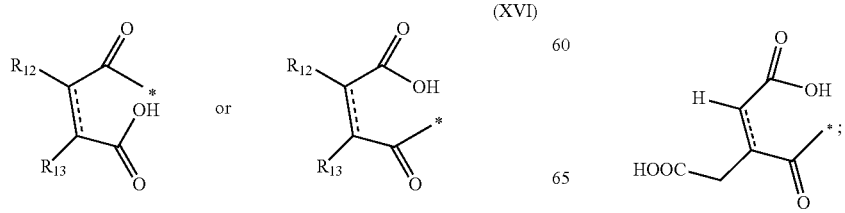

wherein:

$R_{12}$ is hydrogen, $C_{1-5}$ alkyl or $C_{6-10}$ aryl;

$R_{13}$ hydrogen, $C_{1-10}$ alkyl, $C_{6-10}$ aryl, $—(CH_2)_g—CO_2R_{14}$, $—(CH_2)_g—C(O)SR_{14}$, $—(CH_2)_qC(O)S(CH_2)_gCO_2R_{14}$ or $—(CH_2)_qCONHR_{15}$;

$R_{14}$ is hydrogen or $C_{1-5}$ alkyl;

$R_{15}$ is hydrogen, $C_{1-5}$ alkyl, $C_{6-10}$ aryl, aralkyl, alkyldithioaryl, aryldithioalkyl, alkyldithioalkyl, aryldithioaryl, $—(CH_2)_gCHO$ or $R_1$;

g is an integer between 1 and 5 inclusive; q is an integer between 0 and 5 inclusive; and ⁼ is a single or a double bond.

19. The modified polyacetal of claim 18, wherein $R_3$ is:

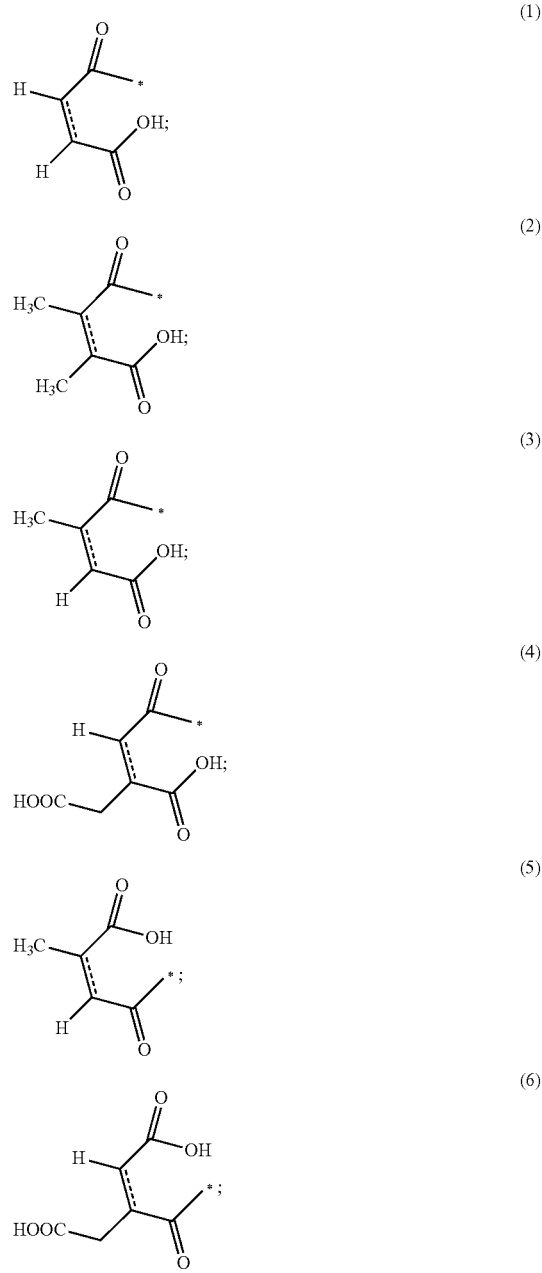

-continued

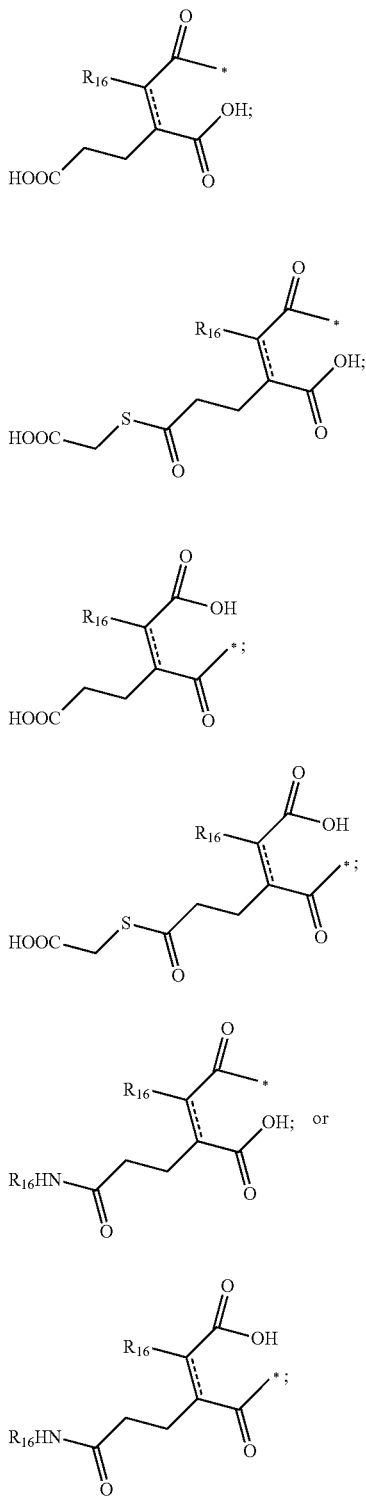

wherein $R_{16}$ is a hydrogen or $C_{1-2}$ alkyl.

20. The modified polyacetal of claim 1, wherein $R_4$ comprises $C_{5-20}$ saturated or unsaturated fatty acids, $C_{6-22}$ alkylamines, cholesterol, cholesterol derivatives or amino containing lipids.

21. The modified polyacetal of claim 20, wherein $R_4$ is:

22. The modified polyacetal of claim 1, wherein $R_6$ is a natural, synthetic, or semi-synthetic polynucleotide, DNA, RNA or an oligonucleotide.

23. The modified polyacetal of claim 22, wherein $R_6$ a double stranded oligonucleotide having about 12 to about 30 nucleotides or a single stranded oligonucleotide having about 8 to about 64 nucleotides.

24. The modified polyacetal of claim 1, wherein the polyacetal backbone has a molecular weight of about 100 kDa, about 70 kDa, about 60 kDa or about 40 kDa.

25. The modified polyacetal claim 1, wherein $R_2$ is

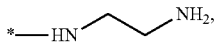

a linear polyethylenimine having a molecular weight of about 500 to about 2500 dalton or a branched polyethylenimine having a molecular weight of about 500 to about 1200 dalton.

26. The modified polyacetal claim 1, wherein $R_3$ is

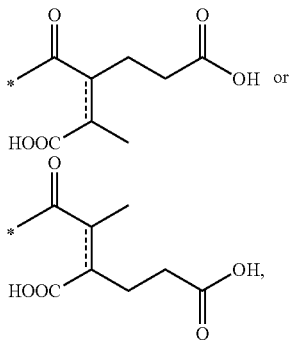

in which ----- is a single or a double bond.

27. The modified polyacetal of claim 1, wherein $R_4$ is

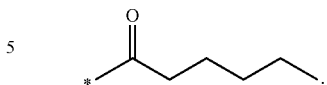

28. A method for delivering a polynucleotide to the cytoplasm of a selected tissue type or cell type, comprising contacting the modified polyacetal of claim 1 with the selected tissue type or cell type.

29. The method of claim 28, wherein the tissue type is a liver tissue or a kidney tissue and the cell type is a blood cell, an endothelial cell, a cancer cell, a pancreatic cell, or a neural cell.

30. A method of reducing expression of a gene in a cell, comprising:
    delivering to the cytoplasm of a cell an effective amount of the modified polyacetal of claim 1, wherein the modified polyacetal contains a polynucleotide that is complementary to at least a portion of the gene.

31. A method of reducing expression of a gene in a subject comprising:
    administering to a subject in need thereof an effective amount of the modified polyacetal of claim 1, wherein the modified polyacetal contains a polynucleotide that is complementary to at least a portion of the gene.

* * * * *